United States Patent
Henschke et al.

(10) Patent No.: US 9,670,234 B2
(45) Date of Patent: Jun. 6, 2017

(54) METAL-CATALYZED ASYMMETRIC 1,4-CONJUGATE ADDITION OF VINYLBORON COMPOUNDS TO 2-SUBSTITUTED-4-OXY-CYCLOPENT-2-EN-1-ONES YIELDING PROSTAGLANDINS AND PROSTAGLANDIN ANALOGS

(71) Applicant: ScinoPharm Taiwan, Ltd., Tainan (TW)

(72) Inventors: Julian Paul Henschke, Summertown (AU); Ping-Yu Wu, Tainan (TW); Hsyueh-Liang Wu, Taipei (TW); Wen-Hsien Wen, Kaohsiung (TW)

(73) Assignee: SCINOPHARM TAIWAN, LTD., Tainan (TW)

( * ) Notice: Subject to any disclaimer, the term of this patent is extended or adjusted under 35 U.S.C. 154(b) by 0 days.

(21) Appl. No.: 14/795,506

(22) Filed: Jul. 9, 2015

(65) Prior Publication Data
US 2016/0009740 A1    Jan. 14, 2016

Related U.S. Application Data

(60) Provisional application No. 62/022,797, filed on Jul. 10, 2014.

(51) Int. Cl.
| | | |
|---|---|---|
| C07F 7/04 | (2006.01) | |
| C07F 7/18 | (2006.01) | |
| C07F 5/02 | (2006.01) | |

(52) U.S. Cl.
CPC ............ *C07F 7/1892* (2013.01); *C07F 5/025* (2013.01); *C07F 7/1856* (2013.01)

(58) Field of Classification Search
CPC .................................................... C07F 7/1892
USPC ...................................................... 556/441
See application file for complete search history.

(56) References Cited

U.S. PATENT DOCUMENTS

2009/0259058 A1    10/2009    Henschke et al.

FOREIGN PATENT DOCUMENTS

| KR | WO 2010104344 A2 * | 9/2010 | ........... C07C 405/00 |
|---|---|---|---|
| WO | WO-2009/141718 A2 | 11/2009 | |
| WO | 2010/104344 A2 | 9/2010 | |
| WO | 2012/048447 A1 | 4/2012 | |

OTHER PUBLICATIONS

Evans et al., J. Org. Chem., 1976, vol. 41, pp. 3947-3953.*
International Search Report, PCT/IB2015/055212, (Aug. 27, 2015).*
Evans et al., J Org Chem, 1976, 41:3947-3953.*
Evans et al., "Stereospecific Olefin Synthesis Via Boronic Esters. Studies Related to Prostaglandin synthesis", Tetrahedron Letters, 1976, No. 18, pp. 1427-1430.
Evans et al., "Studies directed toward the Synthesis of Prostaglandins. Useful Boron-Mediated Olefin Syntheses", J. Org. Chem., 1976, vol. 41, No. 25, pp. 3947-3953.
PCT/IB2015/055212 , "International Search Report and Written Opinion", Aug. 27, 2015, 8 pages.
Babiak et al., "One-Pot Synthesis of Protected Prostaglandins from Alkynes and Cyclopentenones, In Situ Generation of Higher Order Cyanocuprates Derived from Alkenylzirconium Intermediates," *J. Am. Chem. Soc.*, 1990, 112, pp. 7441-7442.
Kluge et al., "Synthesis of Prostaglandin Models and Prostaglandins by Conjugate Addition of a Functionalized Organocopper Reagent," *J. Am. Chem. Soc.*, 94:22, 1972, pp. 7827-7832.
Behling, et al., "In Situ Cuprate Formation via Transmetalation between Vinylstannanes and Higher Order Cyanocuprates," *J. Am. Chem. Soc.*, 1988, 110, pp. 2641-2643.
Takaya et al., "Rhodium-Catalyzed Asymmetric 1,4-Addition of Aryl- and Alkenylboronic Acids to Enones," *J. Am. Chem. Soc.*, 1998, 120, pp. 5579-5580.
Hayashi, et al., "A Chiral Chelating Diene as a New Type of Chiral Ligand for Transition Metal Catalysts: Its Preparation and Use for the Rhodium-Catalyzed Asymmetric 1,4-Addition," *J. Am. Chem. Soc.*, 2003, 125, pp. 11508-11509.
Herran, et al., "Stereoselectivity Control in the Rh(I)-Catalyzed Conjugate Additions of Aryl and Alkenylboronic Acids to Unprotected Hydroxycyclopentenones," Organic Letters, 2005, vol. 7, No. 8, pp. 1669-1671.
Hijfe, et al., "Towards a Large Scale Preparation of Mexiprostil" *Tetrahedron*, vol. 48, No. 31, 1992, pp. 6393-6402.

* cited by examiner

*Primary Examiner* — Sudhakar Katakam
*Assistant Examiner* — Kofi Adzamli
(74) *Attorney, Agent, or Firm* — Mintz, Levin, Cohn, Ferris, Glovsky and Popeo, P.C.

(57) ABSTRACT

This invention provides a novel method for the preparation of 2,3-disubstituted -4-oxy-cyclopentan1-one compounds that are useful for the synthesis of prostaglandins and prostaglandin analogs of industrial relevance. The method comprises the metal-catalyzed asymmetric 1,4-conjugate addition of vinylboron compounds to 2-substituted -4-oxy-cyclopent-2-en-1-ones. This method relies on the use of less toxic, easily-handled reagents, and can be performed under milder conditions than offered by some conventional methods, affording 2,3-disubstituted-4-oxy-cyclopentan-1-one compounds enantio- and diastereoselectively, which are precursors to the said prostaglandin and prostaglandin analogs, in high yield.

22 Claims, 6 Drawing Sheets

METAL-CATALYZED ASYMMETRIC 1,4-CONJUGATE ADDITION OF VINYLBORON COMPOUNDS TO 2-SUBSTITUTED-4-OXY-CYCLOPENT-2-EN-1-ONES YIELDING PROSTAGLANDINS AND PROSTAGLANDIN ANALOGS

CROSS-REFERENCES TO RELATED APPLICATION

The present application claims priority to U.S. Provisional Pat. Appl. No. 62/022,797 filed on Jul. 10, 2014, which application is incorporated herein by reference in its entirety.

BACKGROUND OF THE INVENTION

Natural prostaglandins have a unique chemical structure based on prostanoic acid (7-[(1S,2S)-2-octylcyclopentyl]heptanoic acid) and exhibit a broad range of physiological activities even when present in extremely small amounts. A large number of prostaglandin and prostaglandin analog-based drugs have been developed for a variety of medical indications. For example, tafluprost (ZIOPTAN), travoprost (TRAVATAN) and bimatoprost (LUMIGAN) are used topically (as eye drops) to treat glaucoma and ocular hypertension. Lubiprostone (AMITIZA) is used in the management of chronic constipation. Dinoprostone is a naturally occurring prostaglandin ($PGE_2$) that is used in the clinic for the induction of labor in humans. Therefore, given the pharmaceutical importance of these compounds and their analogs, numerous methods have been developed and disclosed in both academia and industry for the manufacture of prostaglandins and structural analogs of prostaglandins.

An early approach useful for the synthesis of prostaglandin analog $F_{2\alpha}$ and prostaglandin $E_2$ was disclosed by E. J. Corey in 1969 (*J. Am. Chem. Soc.*, 1969, 91, 5675-5676). This approach is referred to as the Corey method, and the well-known Corey lactone—which itself requires about 10 synthetic steps and contains all of the three prostaglandin E (PGE) stereochemical centers already in place—is pivotal to the Corey method. The ω- and α-hydrocarbon-based side chains are added sequentially by Horner-Wadsworth-Emmons and Wittig reactions (see FIG. 1). The Corey method and its more recent modifications and permutations are probably the most used and reported synthetic approaches for the industrial manufacture of prostaglandins and prostaglandin analogs. Disadvantages of this approach include, however, the high cost of the Corey lactone and the burdensome column chromatographic purification that are often required to remove undesired isomers and/or impurities.

Another approach that can be used to prepare prostaglandins and their analogs is sometimes referred to as the two-component approach (*J. Am. Chem. Soc.*, 1972, 94, 3643-3644 and *J. Am. Chem. Soc.*, 1972, 94, 7827-7832). The key characteristic of this approach is the installation of the ω-side chain using a 1,4-conjugate addition reaction of a vinyl organocopper or organocuprate reagent to a cyclopentenone system in which the α-side chain is already present (see FIG. 2). This method, which utilizes organocopper reagents, is referred to herein as the conventional two-component approach. There are many known methods for making α-side chain-substituted cyclopentenones that are useful in the conventional two-component approach. The conventional two-component approach has been used for the synthesis of a variety of prostaglandins and their analogs. Fried. et. al. (*J. Am. Chem. Soc.* 1972, 94, 7827-7832), Lipshutz et al. (*J. Am. Chem. Soc.* 1988, 110, 2641-2643), Lipshutz, et. al. (*J. Am. Chem. Soc.* 1990, 112, 7440-7441) and Van Hijfte et al. (*Tetrahedron* 1992, 48, 6393-6402) have disclosed processes for preparing prostaglandin $E_1$ ($PGE_1$) using the two-component approach, in which various organocuprates, as vinylating agents, were coupled with cyclopentenones by 1,4-conjugate addition under cryogenic temperatures. Organotin reagents, orangolithium reagents, or organozirconium reagents are required as synthetic precursors to the above mentioned organocopper compounds used in the method.

U.S. Pat. No. 7,897,795 (the '795 patent) and U.S. Pat. No. 8,846,958 (the '958 patent) which were disclosed by the applicant, describe the utilization of the conventional two-component approach (see FIG. 2) for the syntheses of certain prostaglandin analogs (e.g., travoprost, bimatoprost, and lubiprostone). In certain processes disclosed in the '795 patent and the '958 patent, a 2-substituted-4-oxy-cyclopent-2-en-1-one intermediate II reacts with a higher order cuprate via 1,4-conjugate addition to give a 2,3-disubstituted-4-oxy-cyclopentan-1-one compound I. This compound, I, can be optionally modified and deprotected to provide various prostaglandin E and prostaglandin F analogs.

However, use of two-component approach is associated with a number of limitations and disadvantages including: the need for cryogenic temperatures (about −50 to −78° C.) in the 1,4-conjugate addition step; the use of organometallic compounds as precursors to the organocopper compounds such as organotin compounds, that are considered toxic and are difficult to purify, or organozirconium compounds, that are moisture sensitive and that can require cryogenic temperatures for their preparation; the use of reactive and difficult to handle organolithium compounds for the preparation of the organocopper compounds; and the need for multiple steps for conversion of the alkyne starting materials through to the requisite organocopper compounds. In addition, the cyanide in some of the cuprate reagents is toxic. The cuprates are not commercially available, due in part to their reactivity and instability under ambient conditions, including their sensitivity to air, which necessitates their immediate use upon synthesis. The reactivity of the cuprate is modulated, and can even be limited, by the electronic nature of substituents on the carbon skeleton adjacent to the copper atom. In fact, in some cases (e.g., tafluprost; see FIG. 4) the desired 1,4-conjugate addition reaction to α-side chain-substituted cyclopentenones does not work. Furthermore, the copper salt used to make the organocopper compounds is required in stoichiometric amounts.

Given the inefficient aspects and operational difficulties associated with the use of the conventional methods in the field to which the present invention pertains, there is a need for the development of a milder, less-toxic, cost-effective and user-friendly process for enantioselectively and diastereoselectively preparing prostaglandin analogs in good yields. Surprisingly, the present invention provides solutions to this and other problems in the relevant field to which the present invention pertains.

BRIEF SUMMARY OF THE INVENTION

In one aspect, the present invention provides a process for preparing a 2,3-disubstituted-4-oxy-cyclopentan-1-one compound of formula I

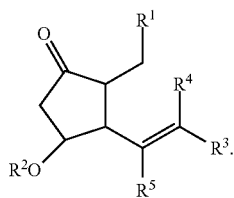

(I)

The process includes contacting a 2-substituted-4-oxy-cyclopent-2-en-1-one compound of formula II

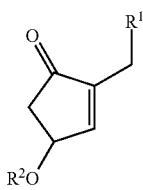

(II)

with a compound of formula III

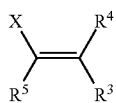

(III)

in a solvent in the presence of a metal additive, optionally in the presence of a basic additive, to give the compound of formula I;

wherein $R^1$, $R^3$, $R^4$ and $R^5$ independently represent hydrogen, aryl, heteroaryl, alkyl, arylalkyl, aryloxyalkyl, alkenyl, or alkynyl;

or $R^3$ and $R^5$ are taken together to form a 5- to 7-membered carbocyclic ring, optionally having one or two heteroatoms as ring vertices, wherein the heteroatoms are selected from the group consisting of O, N and S;

or $R^3$ and $R^4$ are taken together to form a 5- to 7-membered carbocyclic ring, optionally having one or two heteroatoms as ring vertices, wherein the heteroatoms are selected from the group consisting of O, N and S, and wherein each of $R^1$, $R^3$, $R^4$ and $R^5$ are optionally substituted with from one to three members selected from the group consisting of halogen, hydroxy, $C_{1-4}$ alkyl, $C_{1-4}$ haloalkyl, $C_{1-4}$ alkoxy, silyloxy, aryloxy, acyloxy, heterocyclic ring, oxo, COOH, $CONH_2$, $CONHC_{1-4}$alkyl, $C(O)OCH_2C_{6-10}$ aryl, $C(O)OC_{6-10}$ aryl and $C(O)OC_{1-4}$ alkyl;

$R^2$ represents hydrogen or a hydroxyl-protecting group;

X represents a boron-containing group.

Various features which characterize the invention are pointed out with particularity in the claims annexed to and forming a part of the disclosure. For a better understanding of the invention, its operating advantages, and specific objects attained by its use, reference should be had to the drawing and descriptive matter in which preferred embodiments of the invention are illustrated and described.

DETAILED DESCRIPTION OF THE INVENTION

I. General

Figure 1:
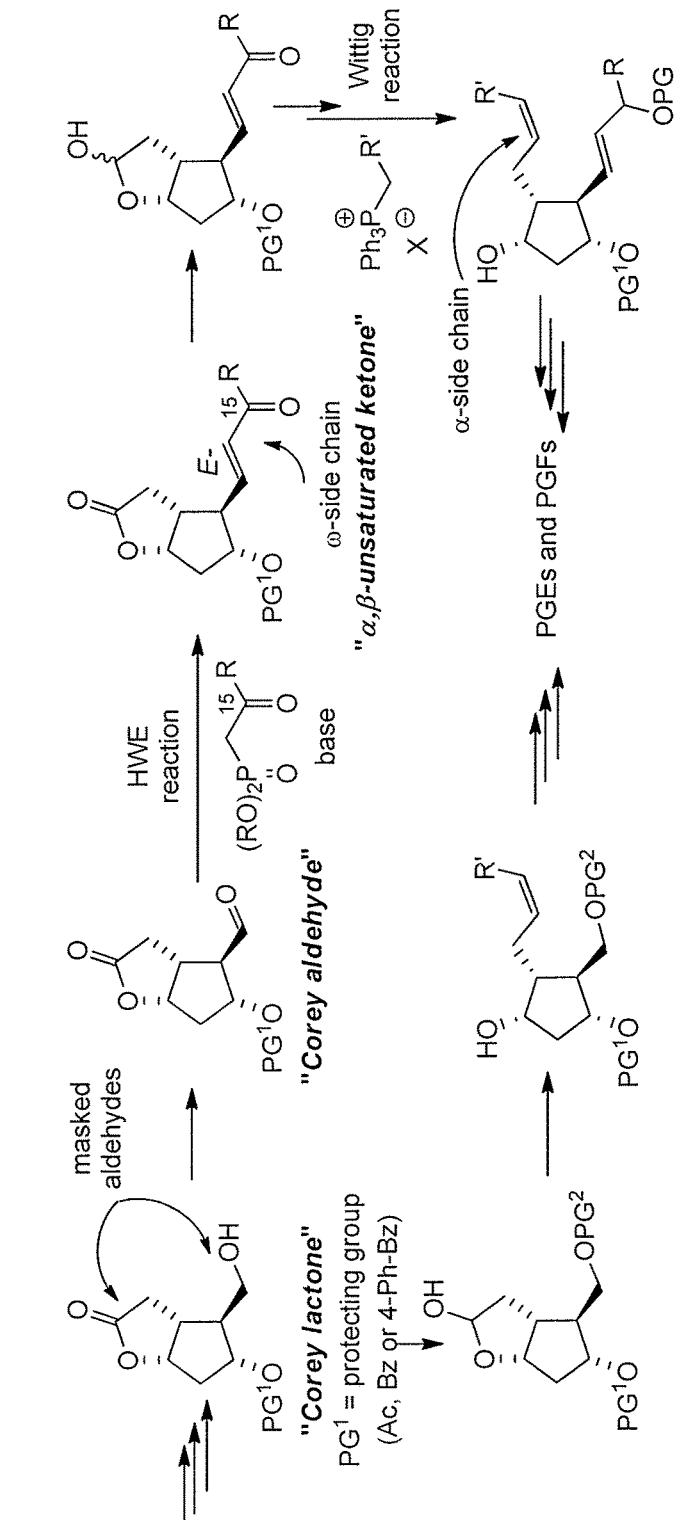
FIG. 1 shows the Corey method for prostaglandin synthesis.
Figure 2:
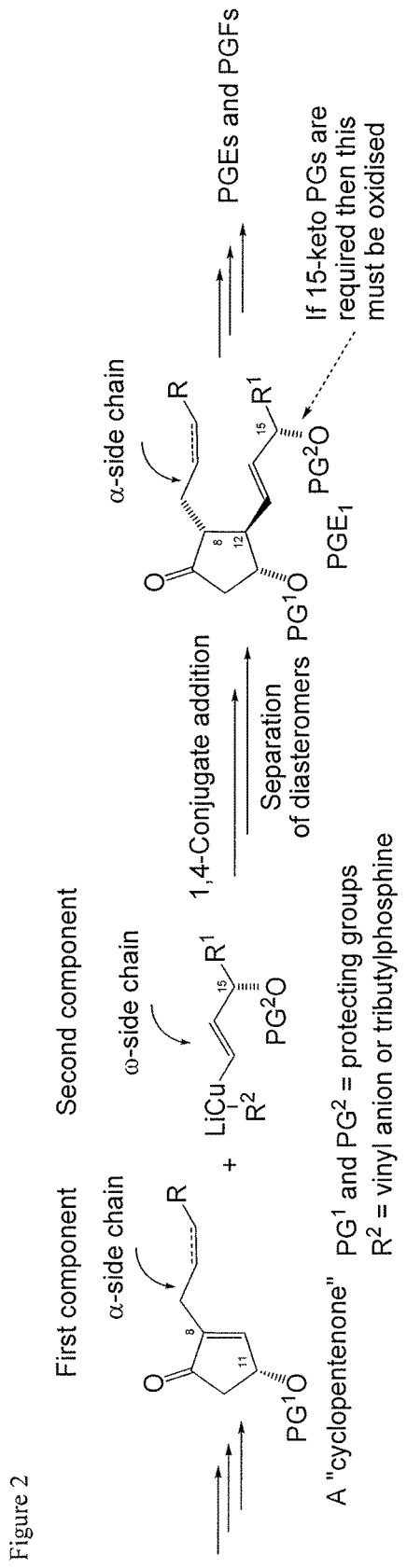
FIG. 2 shows the conventional two-component approach for prostaglandin synthesis.
Figure 3:
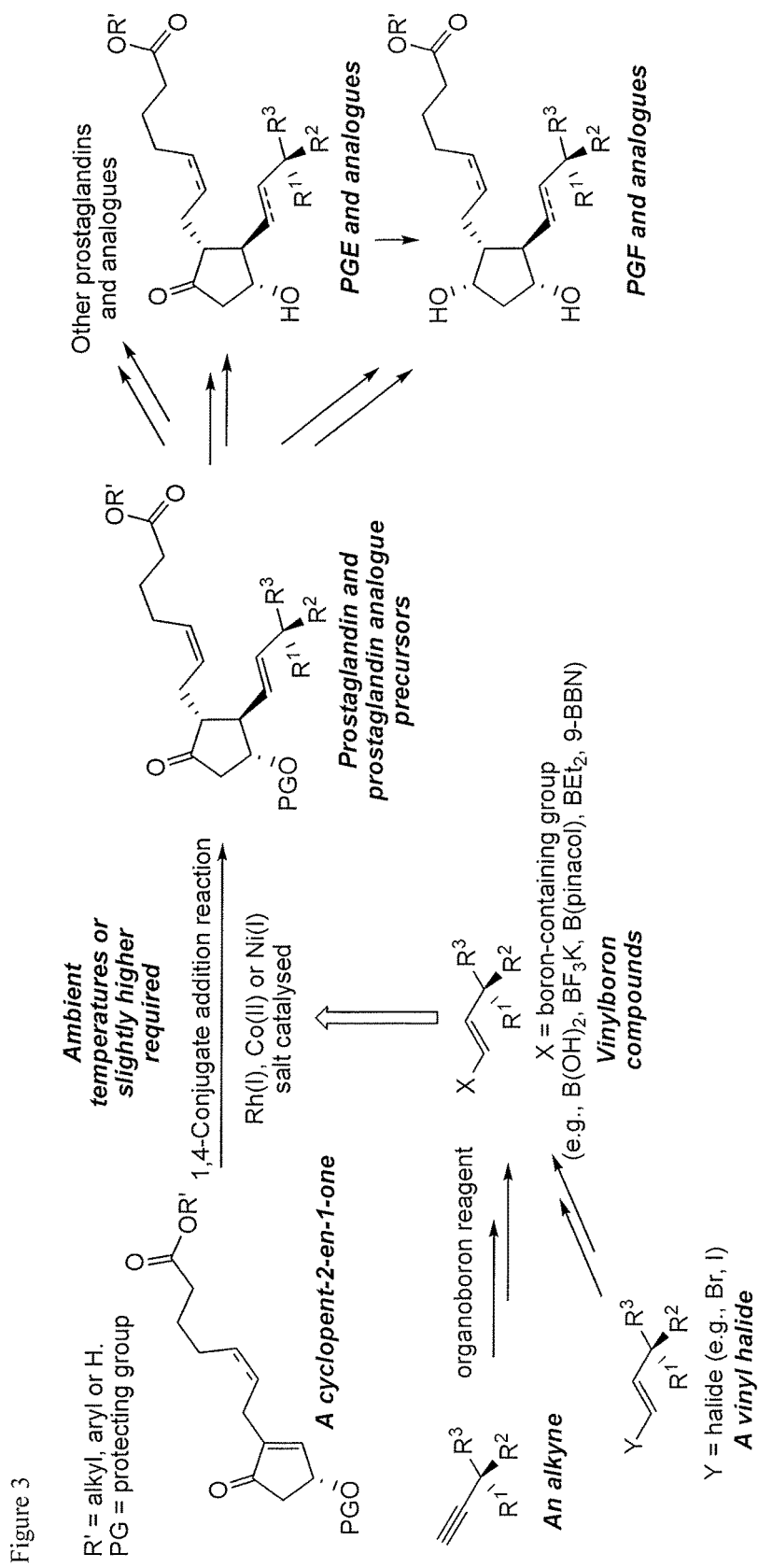
FIG. 3 shows the improved two-component approach for the syntheses of prostaglandins and prostaglandin analogs as disclosed by the present applicant.

The present invention provides a novel method using a metal-catalyzed asymmetric 1,4-conjugate addition reaction of vinylboron compounds and 2-substituted-4-oxy-cyclopent-2-en-1-ones to produce 2,3-disubstituted-4-oxy-cyclopentan-1-one compounds that are useful synthetic precursors of prostaglandins and prostaglandin analogs of industrial and pharmacological importance. This method uses less toxic, more easily-handled reagents, and can be performed under milder reaction conditions, than the conventional two-component method and is able to afford a diverse range of prostaglandin and prostaglandin analog precursors in an enantio- and diastereoselective manner with high yield.

II. Definitions

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the term "metal additive" refers to a catalyst or pre-catalyst that is used in substoichiometric amounts in a chemical reaction. A catalyst is a chemical substance which increases the rate of a chemical reaction of one or more reactants. It should be appreciated, unlike other reagents in the chemical reaction, a catalyst is not consumed by the reaction. A pre-catalyst is a chemical substance that itself might not be chemically active, or is less chemically active, in the said reaction and is converted in the reaction into a catalyst by the action of an additive. Additionally, the term "substoichiometric" refers to an amount that is less than a stoichiometric amount. For example, when 1 mole of compound II is combined with 1 mole or more of compound III, a substoichiometric amount of a metal additive is less than about 1 mole; generally less than about 0.5 moles; in some embodiments, less than about 0.1 moles; in preferred embodiments, from about 0.05 to about 0.0001 moles.

As used herein, the term "basic" is an adjective that refers to a chemical substance that is a base. A basic additive refers to an additive that is a base.

As used herein, the term "alkyl" by itself or as part of another substituent, means, unless otherwise stated, a straight or branched chain hydrocarbon radical. Alkyl substituents, as well as other hydrocarbon substituents, may contain number designators indicating the number of carbon atoms in the substituent (i.e. $C_{1-8}$ means one to eight carbons), although such designators may be omitted. Unless otherwise specified, the alkyl groups of the present invention contain 1 to 12 carbon atoms. For example, an alkyl group can contain 1-2, 1-3, 1-4, 1-5, 1-6, 1-7, 1-8, 1-9, 1-10, 1-11, 1-12, 2-3, 2-4, 2-5, 2-6, 3-4, 3-5, 3-6, 4-5, 4-6 or 5-6 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The terms "alkenyl" and "alkynyl" refer to an alkyl group as defined above, having one or more carbon-carbon double bonds (alkenyl) or carbon-carbon triple bonds (alkynyl), respectively. For those groups having both a carbon-carbon double bond and a carbon-carbon triple bond, the term "alkynyl" is used.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "arylalkyl" is meant to include those radicals in which an aryl group is attached to an alkyl group (e.g., benzyl, phenethyl, and the like). Similarly, the term "aryloxyalkyl" is meant to include those radicals in which an aryl group is attached to an alkyl group via an ether linkage (—O—), for example, phenoxypropyl, phenoxypentyl, and phenoxyheptyl.

As used herein, the term "silyloxy" refers to a moiety having the formula —OSiR$_3$, wherein each R is independently an alkyl group or aryl group as defined herein. Examples of silyloxy groups include, but are not limited to, trimethylsilyloxy, triethylsilyloxy, and (tert-butyl)dimethylsilyloxy.

As used herein, the term "acyloxy" refers to a moiety having the formula —OC(O)R, wherein R is an alkyl group, an aryl group, or an arylalkyl group as defined herein. Examples of acyloxy groups include, but are not limited to, acetyloxy and benzoyloxy.

As used herein, the term "protecting group" refers to a moiety that is formed to render a functional moiety unreactive, or less reactive. The protecting group can be removed so as to restore the functional moiety to its original state. Various protecting groups and protecting reagents, including hydroxyl protecting groups, are well known to one of ordinary skill in the art and include compounds that are disclosed in *Protective Groups in Organic Synthesis,* 4th edition, T. W. Greene and P. G. M. Wuts, John Wiley & Sons, New York, 2006, which is incorporated herein by reference in its entirety.

The term "diene ligand" refers to an organic compound containing two carbon-carbon double bonds, that together form a diene system, that can coordinate to rhodium(I) salts. The diene ligand can be, but is not limited to, norbornadiene, 1,5-cyclooctadiene, bicyclo[2.2.2]octa-2,5-diene system, bicyclo[2.2.1]hepta-2,5-diene system and bicyclo[2.2.0]octa-2,6-diene system.

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed. The following schemes are provided as embodiments to illustrate, but not to limit the present invention.

III. Embodiment of the Invention

The present invention provides a process for preparing a 2,3-disubstituted-4-oxy-cyclopentan-1-one compound of formula I

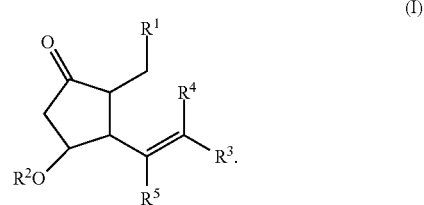

(I)

The process includes contacting a 2-substituted-4-oxy-cyclopent-2-en-1-one compound of formula II

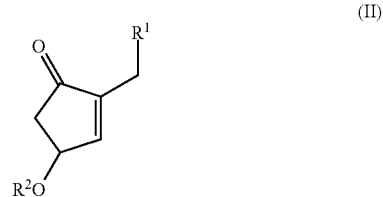

(II)

with a compound of formula III

(III)

in a solvent in the presence of a metal additive, optionally in the presence of a basic additive, to give the compound of formula I;

wherein $R^1$, $R^3$, $R^4$ and $R^5$ independently represent hydrogen, aryl, heteroaryl, alkyl, arylalkyl, aryloxyalkyl, alkenyl, or alkynyl;

or R³ and R⁵ are taken together to form a 5- to 7-membered carbocyclic ring, optionally having one or two heteroatoms as ring vertices, wherein the heteroatoms are selected from the group consisting of O, N and S;

or R³ and R⁴ are taken together to form a 5- to 7-membered carbocyclic ring, optionally having one or two heteroatoms as ring vertices, wherein the heteroatoms are selected from the group consisting of O, N and S, and wherein each of $R^1$, $R^3$, $R^4$ and $R^5$ are optionally substituted with from one to three members selected from the group consisting of halogen, hydroxy, $C_{1-4}$ alkyl, $C_{1-4}$ haloalkyl, $C_{1-4}$ alkoxy, silyloxy, aryloxy, acyloxy, heterocyclic ring, oxo, COOH, CONH₂, CONHC$_{1-4}$alkyl, C(O)OCH₂C$_{6-10}$ aryl, C(O)OC$_{6-10}$ aryl and C(O)OC$_{1-4}$ alkyl;

$R^2$ represents hydrogen or a hydroxyl-protecting group;

X represents a boron-containing group.

Figure 4:
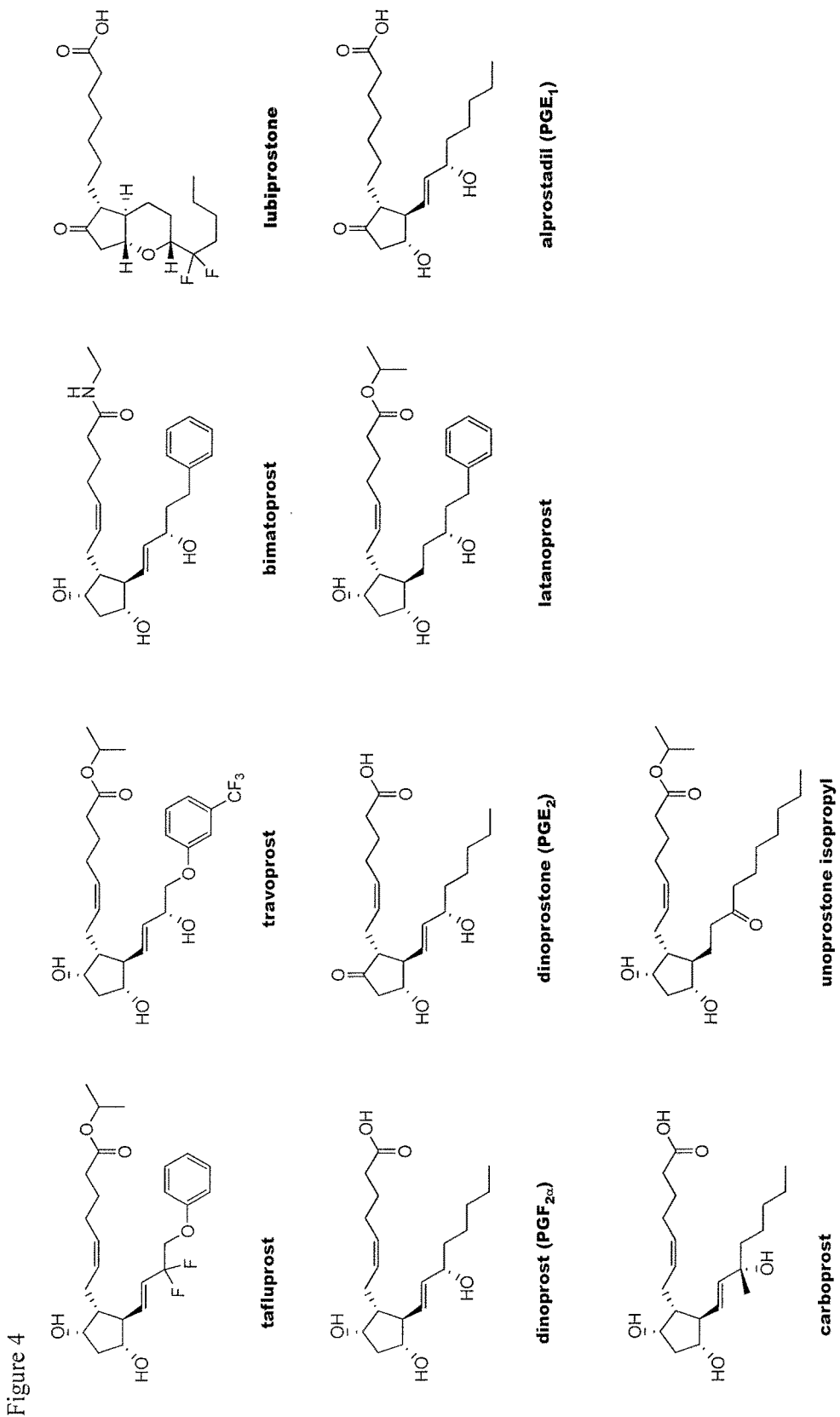
FIG. 4 shows some prostaglandin and prostaglandin analogs of industrial and pharmaceutical importance.
Figure 5:
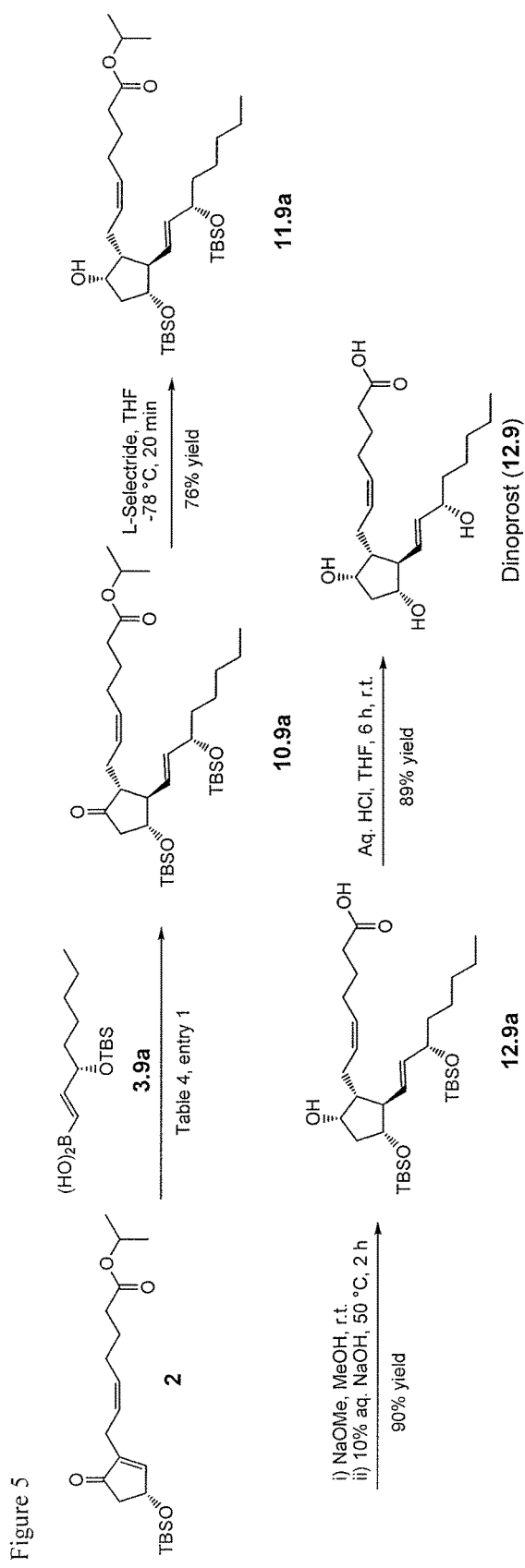
FIG. 5 shows the synthesis of dinoprost using the present invention.

Without wishing to be bound by any particular theory, it is believed that products of formula I are formed via a 1,4-conjugate addition reaction. The boron-containing compound III is a vinylboron compound, wherein the boron atom is present in the radical X and is covalently bonded to one of the carbon atoms of the carbon-carbon double bond of compound III. The process of the invention provides compounds of formula I that can be used for the preparation of prostaglandins and prostaglandin analogs. The prostaglandins and prostaglandin analogs include, but are not limited to, compounds of the prostaglandin E (PGE) and prostaglandin F (PGF) series and their analogs. Examples of the PGE and PGF series compounds (see FIG. 4) or analogs of these include, but are not limited to, travoprost (a PGF$_{2\alpha}$ analog), bimatoprost (a PGF$_{2\alpha}$ analog), dinoprost (PGF$_{2\alpha}$; see also FIG. 5), dinoprostone (PGE₂), lubiprostone (a PGE analog), tafluprost (a PGF$_{2\alpha}$ analog; see also FIG. 6), carboprost (a PGF$_{2\alpha}$ analog), alprostadil (PGE₁), latanoprost (a PGF$_{2\alpha}$ analog) and unoprostone (a PGF$_\alpha$ analog).

In some embodiments, the compound of formula I has formula I'

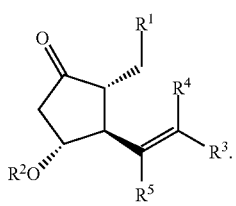

(I')

The reactions in the process of the invention can be conducted at any suitable temperature. In some embodiments, the 1,4-conjugate addition reaction step can be performed at ambient temperature (20-30° C.), under cooled (about 0° C.) conditions or under mildly heated (about 50° C.) conditions. Examples of instruments used to provide heat to the reaction include, but are not limited to, conventional heating equipment (such as an oil bath, a heating jacket, or a heating mantle) or microwave reactors. Subzero or cryogenic temperatures are typically not required when operating this process. In contrast, the known processes implementing the conventional two-component approach usually require cryogenic temperatures in the corresponding 1,4-conjugate addition reaction step.

Reaction temperatures such as about 30° C. can provide higher yields of 2,3-disubstituted-4-oxy-cyclopentan-1-one compounds I than can higher temperatures such as 50° C., 60° C. or 80° C., because at higher temperatures significant amounts of 2,3,4-trisubstituted-cyclopentan-1-one compounds VIII can form. For example, from about 3% up to about 15% (based on 2-substituted-4-oxy-cyclopent-2-en-1-one II) of the side product compounds VIII can form in certain instances.

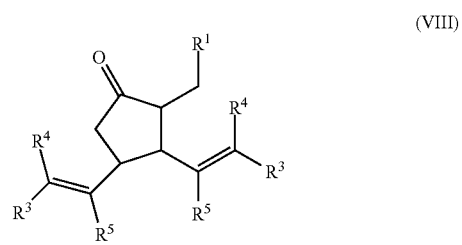

(VIII)

Without wishing to be bound by any particularly theory, it is believed that compounds VIII are formed from reactive precursors V, that themselves are degradation products of compounds I, and are formed by elimination of the 4-oxy substituent.

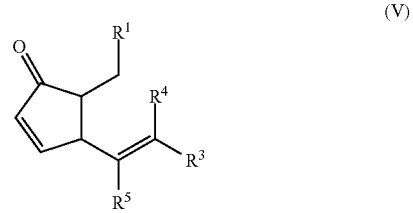

(V)

In support of this, when the 1,4-conjugate addition product, prostaglandin E₂ analog 10.1, was subjected to the standard 1,4-conjugate addition conditions of this invention ([RhCl(COD)]₂, KOH, 60° C. in the presence of trans-2-phenylvinylboronic acid (3.1)) for an extended reaction time of 18 h, compound 6.1 was formed as the major reaction product.

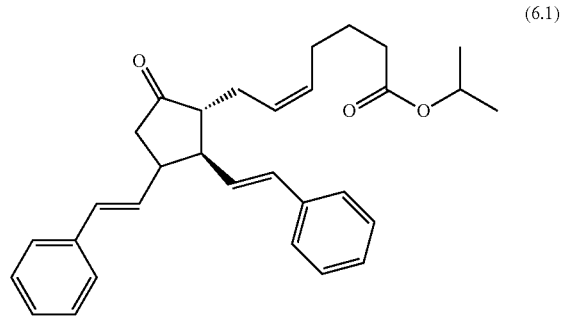 [SMILES: CC(C)OC(=O)CCC/C=C\C[C@H]1C(=O)CC(/C=C/c2ccccc2)[C@@H]1/C=C/c1ccccc1]

(6.1)

In addition to reaction temperature, the amounts of compounds VIII formed can depend on other reaction parameters such as the type of basic additive, the reaction solvent and reaction time (such as when extended reaction times are applied).

In general, for each set of substrates II and III and reaction solvent and basic additive, a reaction temperature is selected that provides the highest yield of 2,3-disubstituted-4-oxy-cyclopentan-1-one compounds I and that provides none, or a low level, of the 2,3,4-trisubstituted-cyclopentan-1-one compounds VIII. As non-limiting examples, Table 1, entries 1-3 show that lower temperatures can provide higher 2,3-disubstituted-4-oxy-cyclopentan-1-one compound I yields for reactions conducted in methanol using potassium hydroxide as the basic additive. When microwave irradiation (μw) was used and the reaction temperature was maintained at 50° C., 40° C. or 30° C., the level of the 2,3,4-trisubstituted-cyclopentan-1-one 6.1 was reduced from 9% to 3% to 0% yield, respectively. Meanwhile, the desired 2,3-disubstituted-4-oxy-cyclopentan-1-one compound 10.1 increased from 65% to 73% to 83%, respectively.

TABLE 1

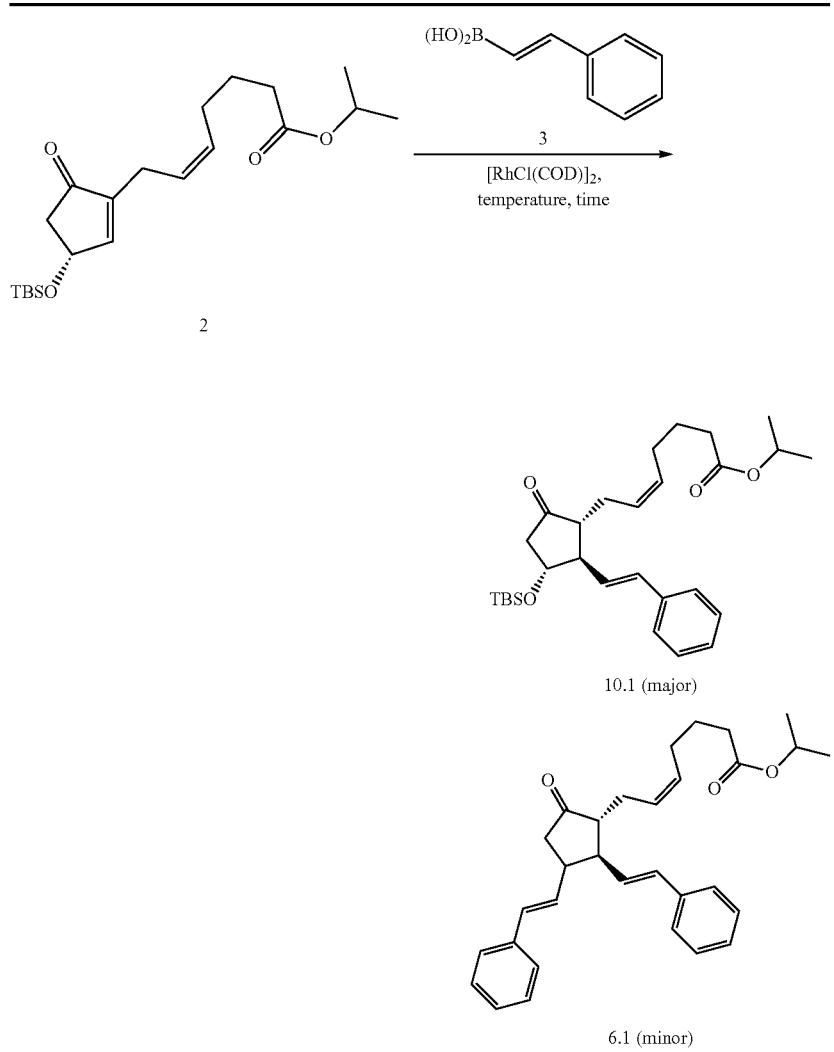

| Entry | Mole equivalent vinylboron compound 3.1[a] | Mole equivalent of [RhCl(COD)]$_2$[a] | Base | Solvent | Temp.[b] | Time | % yield 10.1 (% yield 6.1) |
|---|---|---|---|---|---|---|---|
| 1 | 1.5 | 1.5 | KOH | MeOH | 50° C. (μw) | 3 h | 65% (9%) |
| 2 | 1.5 | 1.5 | KOH | MeOH | 40° C. (μw) | 6 h | 73% (3%) |
| 3 | 1.5 | 1.5 | KOH | MeOH | 30° C. (μw) | 7 h | 83% (0%) |
| 4 | 1.5 | 1.5 | KOH | MeOH | 30° C. (μw) | 5 h | 84% |
| 5 | 1.5 | 3 | KOH | MeOH | 30° C. (μw) | 5 h | 84% |

TABLE 1-continued

| # | | | | | | | |
|---|---|---|---|---|---|---|---|
| 6 | 1.5, 0.5 | 1.5, 1.5 | KOH | MeOH | 30° C. (μw) | 5 h, 1 h | 96% |
| 7 | 1.5, 0.5 | 1.5, 1 | KOH | MeOH | 30° C. (μw) | 5 h, 1 h | 90% |
| 8 | 1.5 | 1.5 | t-BuOK | i-PrOH | 45° C. | 4.5 days | 78% (0%) |
| 9 | 1.5, 1.5 | 1.5 | NH$_2$(CH$_2$)$_3$NH$_2$ | i-PrOH | 25° C. | 3 days | 42% (15%) |
| 10 | 1.5 | 1.5 | KOH | i-PrOH | 0° C. | 3 days | 88% (0%) |
| 11 | 1.5 | 1.5 | KHF$_2$ | i-PrOH | 25° C. | 3 days | 74% (5%) |
| 12 | 1.5 | 1.5 | NaOH | i-PrOH | 25° C. | 3 days | 35% (0%) |
| 13 | 1.5 | 1.5 | K$_3$PO$_4$ | i-PrOH | 25° C. | 3 days | 54% (18%) |
| 14 | 1.5 | 1.5 | KOH | i-PrOH | 25° C. | 3 days | 70% (3%) |
| 15 | 1.5 | 1.5 | KOH | MeOH | 25° C. | 3 days | 80% (3%) |
| 16 | 1.5 | 1.5 | KOH | EtOH | 25° C. | 3 days | 76% (11%) |
| 17 | 1.5 | 1.5 | KOH | t-BuOH | 25° C. | 3 days | 58% (0%) |
| 18 | 1.5 | 1.5 | KOH | 1:1 MeOH/H$_2$O | 25° C. | 3 days | 61% (0%) |
| 19 | 1.5 | 1.5 | KHF$_2$ | MeOH | 25° C. | 3 days | 75% (0%) |
| 20 | 1.5 | 1.5 | KHF$_2$ | 1:1 MeOH/H$_2$O | 25° C. | 3 days | 48% (0%) |
| 21 | 1.5 | 1.5 | KHF$_2$ | 1,4-dioxane | 25° C. | 3 days | 48% (0%) |

$^a$When two values appear separated by a comma, this indicates the portionwise addition of the additive and/or reagent. The corresponding comma between the time units in the column for time indicates the reaction time period following each of the corresponding additions of additive.

$^b$μw indicates that the reaction solution was irradiated with microwaves. The stated temperature (Temp.) is that reported by the microwave reactor.

Any suitable solvent can be used in the 1,4-conjugate addition reaction step utilizing the vinylboron compounds. Examples of suitable solvents include, but are not limited to, water, methanol, ethanol, isopropyl alcohol, isobutyl alcohol, 1,4-dioxane, toluene, tetrahydrofuran (THF), 2-methyltetrahydrofuran (2-Me-THF), diglyme, acetonitrile, N-methylpyrrolidone (NMP), N,N-dimethylformamide (DMF), N,N-dimethylacetamide (DMAC), ethylene glycol and combinations thereof. The 1,4-conjugate addition reaction step utilizing vinylboron compounds can be conducted in protic or aprotic solvents. In some embodiments, the reaction is conducted in a protic solvent. In some embodiments, the protic solvent is an alcohol solvent. In some embodiments, the alcohol solvent is methanol. Methanol not only provides a good medium to conduct the 1,4-conjugate addition reaction of this invention, but also is cheap, readily available and easy to handle and dispose of on manufacturing scales.

Any suitable boron compound can be used in the process of the invention. Examples of suitable vinylboron compounds include, but are not limited to, vinylboronic acids, vinyl boroxines, vinylboronic esters (e.g., pinacolboronic esters and catecolboronic esters), trivinylboranes, dialkylvinylboranes, vinyl N-imino diacetic acid boronates, B-vinyl-9-BBN compounds, vinyltriol borates, trifluorovinylborate salts, and tetravinylborate salts. Preferably, the vinylboron compound is a vinylboronic acid or a vinyltrifluoroborate salt. That is, the boron-containing group X of the compound of formula III is selected from the group consisting of B(OH)$_2$ (a vinylboronic acid); B(OR)$_2$ (a vinylboronic ester) where R is an alkyl group or an aryl group; BR$_2$ (a dialkylvinylborane) where R is an alkyl group; BR$_2$ (a trivinylborane) where R is a vinyl group; a 9-borabicyclo[3.3.1]nonane (9-BBN) group; BR$_2$ where R is a carboxylate group; BR where R is a bidentate carboxylate group; BR$_2$ where R is an aryloxy group; BR where R is a bidentate aryloxy group, BF$_3$M (a vinyltrifluoroborate salt) where M is a metal ion, BF$_3$M where M is an is an ammonium or phosphonium ion, BR$_3$M (a trialkylvinylborate salt) where R is an alkyl group and M is a metal ion or an ammonium or phosphonium ion, and BR$_3$M (a tetravinylborate salt) where R is a vinyl group and where M is a metal ion or is an ammonium or phosphonium ion.

Table 2, entries 1-5 show that the same 2-phenylvinyl radical can be delivered to 2-substituted-4-oxy-cyclopent-2-en-1-one 2 in the 1,4-conjugate addition reaction via the vinylboronic acid 3.1 (entry 1), potassium vinyltrifluoroborate 3.1a (entry 2), catechol vinylboronate 3.1b (entry 3), pinacol vinylboronate 3.1c (entry 4) and N-methylimino diacetic acid vinylboronate 3.1d (entry 5), to provide the protected prostaglandin E$_2$ analog 10.1.

TABLE 2
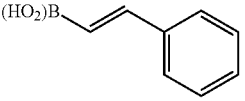
| Entry | Vinylboron compound 3 (mole equivalent[b]) | Mole equivalent of [RhCl(COD)]$_2$[b] | Solvent | Time | % Yield of 10.1 |
|---|---|---|---|---|---|
| 1 | 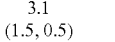<br>3.1<br>(1.5, 0.5) | 1.5, 1.5 | MeOH | 5 h, 1 h | 96% |
| 2 | 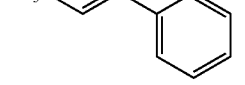<br>3.1a<br>(1.5, 0.5) | 1.5, 1.5 | MeOH | 3 h, 2 h | 48% |
| 3 | 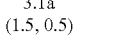<br>3.1b<br>(1.5, 0.5) | 1.5, 1.5 | MeOH | 3 h, 2 h | 28% |
| 4 | 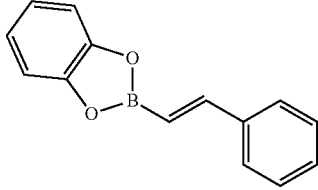<br>3.1c<br>(1.5, 0.5) | 1.5, 1.5 | MeOH | 3 h, 2 h | 58% |

TABLE 2-continued

| 5 | [structure of 3.1d: N-methyl diethanolamine boronate of styrene] (1.5) | 1.5 | MeOH/H₂O (3/10) | 6 h | 12% |

[a] µw indicates that the reaction solution was irradiated with microwaves. The stated temperature is that reported by the microwave reactor. The corresponding comma between the time units in the column for time indicates the reaction time period following each of the corresponding additions of additive.
[b] When two values appear separated by a comma, this indicates the portionwise addition of the additive and/or reagent.

The aforesaid vinylboron compounds III are easy to prepare using methods described in the literature and can often be isolated as solids, which are sometimes crystalline. Further, the vinylboron compounds III are generally air and moisture stable (i.e., water tolerant) and have a long shelf-life, unlike the corresponding vinylcuprate compounds used in the conventional two-component approach that must often be used immediately, or soon after preparation. The vinylboron compounds III can be easily handled in the laboratory or in the manufacturing plant, and can be purchased from commercial sources or prepared in-house and then stored under ambient conditions until needed. Moreover, these vinylboron compounds are generally considered to be "non-toxic", which is suitable for industrial and pharmaceutical applications. The use of vinylboron compounds III in the present invention is a significant improvement upon the use of vinylcopper compounds (vinylcuprates) of the conventional two-component method.

Surprisingly, the 1,4-conjugate addition reaction of this invention can function over a structurally diverse range of vinylboron compounds of formula III. As summarized in Table 3, entries 1-8, high yields of 2,3-disubstituted-4-oxy-cyclopentan-1-one compounds 10 (protected prostaglandin $E_2$ analogs) were obtained using the 2-substituted-4-silyloxy-cyclopent-2-en-1-one compound of formula 2 and vinylboronic acids 3, where $R^4$ and $R^5$ are H and $R^3$ is phenyl (3.1, entry 1), 4-methoxyphenyl (3.2, entry 2), 3-methoxyphenyl (3.12, entry 3), 4-methylphenyl (3.3, entry 4), 3-methylphenyl (3.4, entry 5), 2-methylphenyl (3.11, entry 6), 4-trifluoromethylphenyl (3.14, entry 7), or 4-fluorophenyl (3.13, entry 8). Moreover, when $R^4$ is H and $R^3$ and $R^5$ form a carbocyclic ring (i.e., 3.20; entry 9) the corresponding 2,3-disubstituted-4-oxy-cyclopentan-1-one compound of formula 10.20 was obtained. Furthermore, the non-aromatic vinylboronic acids 3.6 (entry 10), 3.5 (entry 11), 3.16 (entry 12), and 3.15 (entry 13) generally provided good to high yields of the corresponding 2,3-disubstituted-4-oxy-cyclopentan-1-one compounds of formula 10.6, 10.5, 10.16 and 10.15 (prostaglandin $E_2$ analogs).

TABLE 3

[Reaction scheme: compound 2 (TBSO-cyclopentenone with isopropyl ester side chain) + vinylboron compound 3 ($R_2B$-CR⁵=CR³R⁴) → under [RhCl(COD)]₂, KOH, MeOH 30° C. (µw)[a] → compound 10 (% Yield)]

| Entry | Vinylboron compound 3 (mole equivalents[b]) | [RhCl(COD)]₂ (mole equivalents[b]) | Time | |
|---|---|---|---|---|
| 1 | (HO)₂B-CH=CH-Ph  3.1  1.5, 0.5 | 1.5, 1.5 | 5 h, 1 h | 10.1 (96%) |

TABLE 3-continued
| | | | | |
|---|---|---|---|---|
| 2 | 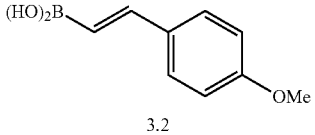<br>3.2<br>1.5, 0.5 | 1.5, 1.5 | 5 h, 1 h | 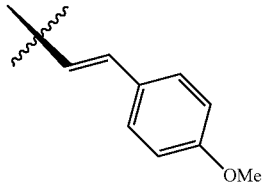<br>10.2<br>(93%) |
| 3 | 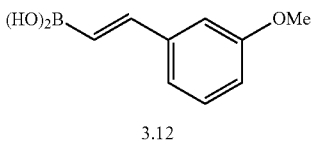<br>3.12<br>1.5, 0.5 | 1.5, 1.5 | 3 h, 2 h | 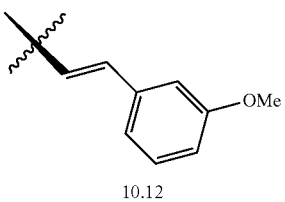<br>10.12<br>(93%) |
| 4 | 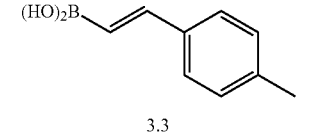<br>3.3<br>1.5, 0.5 | 1.5, 1.5 | 5 h, 1 h | 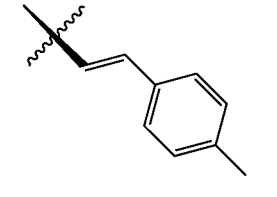<br>10.3<br>(95%) |
| 5 | 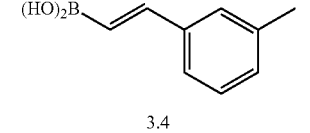<br>3.4<br>1.5, 0.5 | 1.5, 1.5 | 5 h, 1 h | 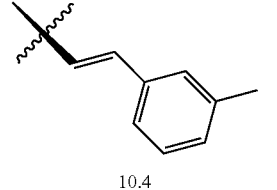<br>10.4<br>(98%) |
| 6 | 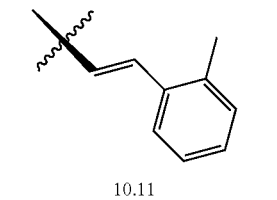<br>3.11<br>1.5, 0.5 | 1.5, 1.5 | 3 h, 2 h | 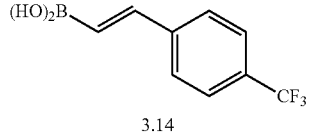<br>10.11<br>(88%) |
| 7 | 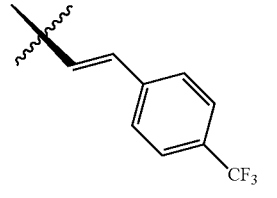<br>3.14<br>1.5, 0.5 | 1.5, 1.5 | 3 h, 2 h | <br>10.14<br>(80%) |

TABLE 3-continued

| # | Reagent | equiv | time | Product |
|---|---|---|---|---|
| 8 | (HO)₂B–CH=CH–C₆H₄–F (3.13) 1.5, 0.5 | 1.5, 1.5 | 3 h, 2 h | 10.13 (92%) |
| 9 | (HO)₂B–cyclohexenyl (3.20) 1.5, 0.5 | 1.5, 1.5 | 3 h, 2 h | 10.20 (38%) |
| 10 | (HO)₂B–CH=CH–C₆H₁₃ (3.6) 1.5, 0.5 | 1.5, 1.5 | 5 h, 1 h | 10.6 (93%) |
| 11 | (HO)₂B–CH=C(CH₃)₂ (3.5) 1.5, 0.5 | 1.5, 1.5 | 5 h, 1 h | 10.5 (99%) |
| 12 | (HO)₂B– (3.16) 1.5, 0.5 | 1.5, 1.5 | 3 h, 2 h | 10.16 (37%) |
| 13 | (HO)₂B– (3.15) 1.5, 0.5 | 1.5, 1.5 | 3 h, 2 h | 10.15 (76%) |
| 14 | (HO)₂B–cyclohexenyl (3.20) 1.5, 0.5 | 1.5, 1.5 | 5 h, 1 h | 10.20 (38%) |

[a]μw indicates that the reaction solution was irradiated with microwaves. The stated temperature is that reported by the microwave reactor.
[b]When two values appear separated by a comma, this indicates the portionwise addition of the additive and/or reagent. The corresponding comma between the time units in the column for time indicates the reaction time period following each of the corresponding additions of additive.

The applicability of the inventive method to the synthesis of precursors to prostaglandins and prostaglandin analogs of pharmaceutical importance is demonstrated by the non-limiting examples summarized in Table 4. The 1,4-conjugate addition reaction of 2-substituted-4-oxy-cyclopent-2-en-1-one compound of formula 2 and vinylboronic acids 3.9a (entry 1), 3.17 (entry 3), 3.18 (entry 4), or 3.7 (entry 5) provided 2,3-disubstituted-4-oxy-cyclopentan-1-one compounds of formula 10.9a, 10.17, 10.18, and 10.7 (prostaglandin $E_2$ analogs), respectively. Such compounds are known and reported synthetic precursors to dinoprost, bimatoprost, travoprost and tafluprost, respectively, which themselves are prostaglandin $F_{2\alpha}$ analogs that are used for the inducement of labor or in the treatment of disease. See, for example, the '795 patent for the use of protected prostaglandin $E_2$ analogs 10.17 and 10.18 for the synthesis of prostaglandin $F_{2\alpha}$ analogs bimatoprost and travoprost, respectively. Similarly, vinyl pinacolboronate 2.9a (entry 2), potassium vinyl trifluoroborate 3.7a (entry 6), or vinyl pinacolboronate 2.19 (entry 7) can be used in the 1,4-conjugate addition reaction to provide 2,3-disubstituted-4-oxy-cyclopentan-1-one compounds of formula 10.9a, 10.7, and 10.19, which are known and reported synthetic precursors to the prostaglandin $F_{2\alpha}$ analogs dinoprost and tafluprost, and the prostaglandin $E_1$ derivative lubiprostone, respectively. See, for example, the '958 patent for the use of the protected prostaglandin $E_2$ analog 10.19 for the synthesis of lubiprostone.

TABLE 4

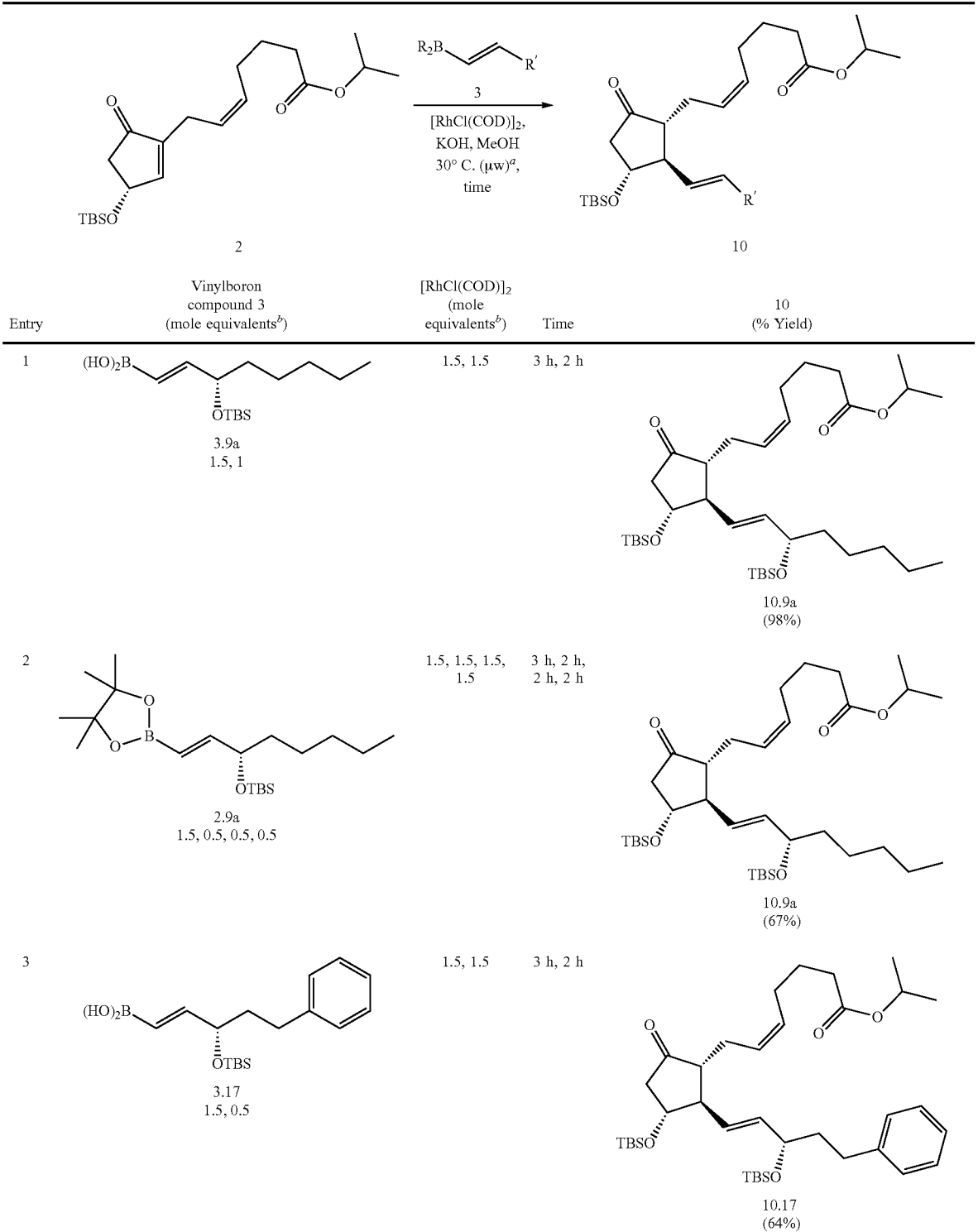

TABLE 4-continued

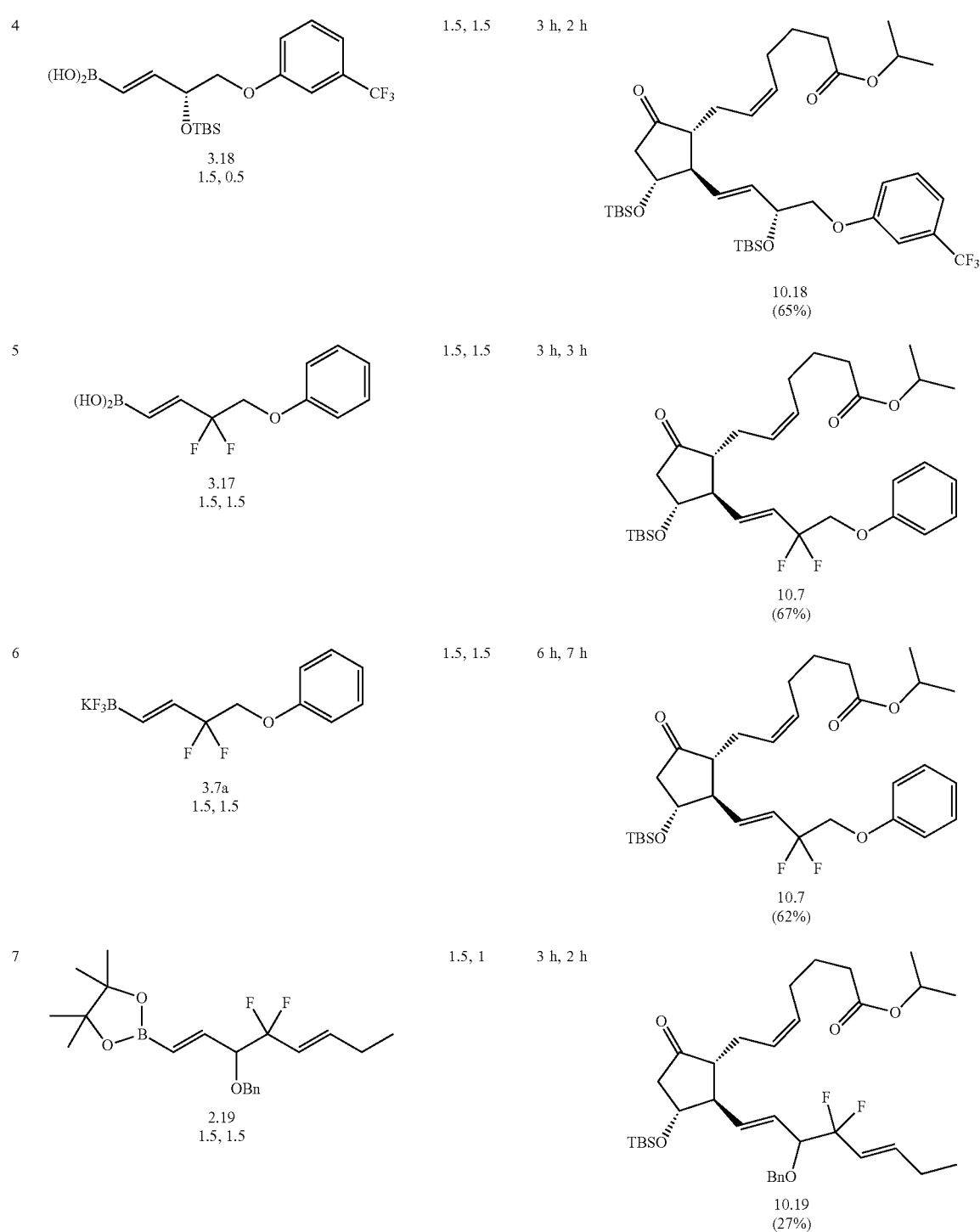

<sup>a</sup>μw indicates that the reaction solution was irradiated with microwaves. The stated temperature is that reported by the microwave reactor.
<sup>b</sup>When two values appear separated by a comma, this indicates the portionwise addition of the additive and/or reagent. The corresponding comma between the time units in the column for time indicates the reaction time period following each of the corresponding additions of additive.

Figure 6:
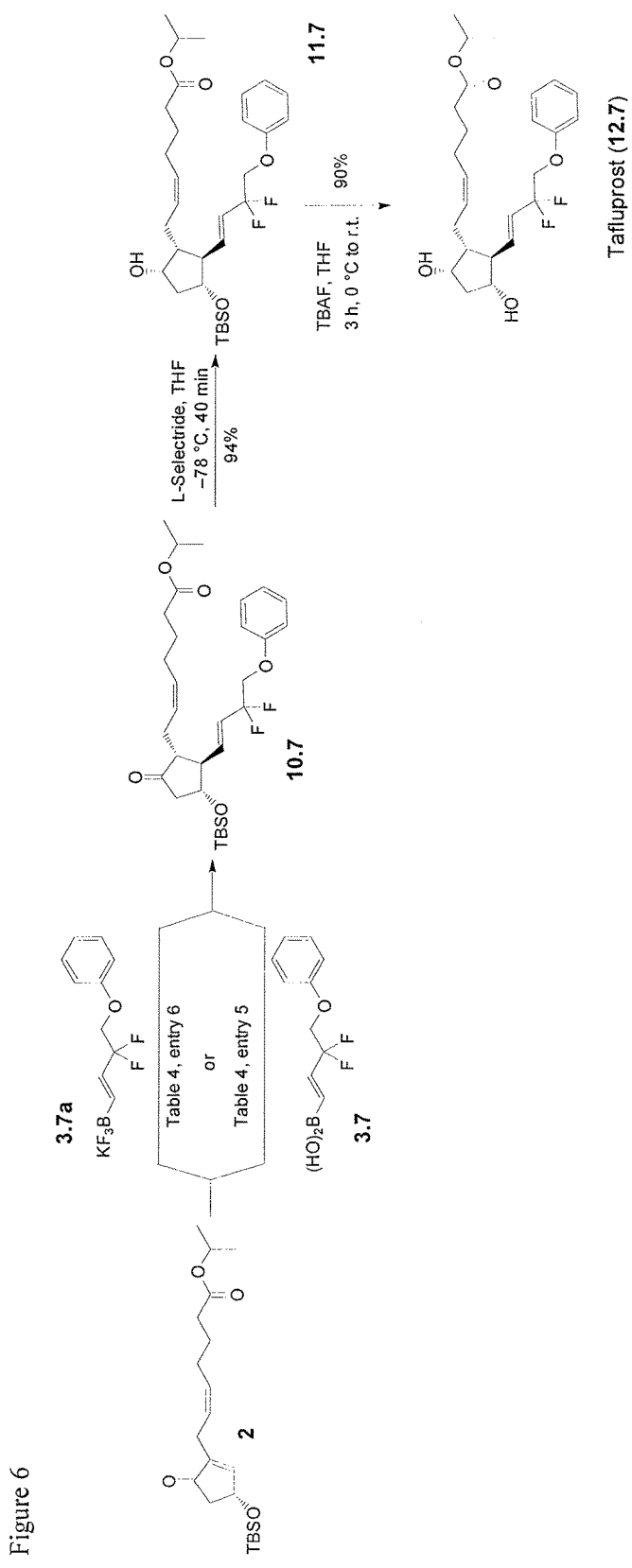
FIG. 6 shows the synthesis of tafluprost using the present invention.

It is notable that while multiple attempts to prepare the 2,3-disubstituted-4-oxy-cyclopentan-1-one compound of formula 10.7, useful for making tafluprost, utilizing the conventional two component approach using the corresponding vinylcuprate VII and 2-substituted-4-silyloxy-cyclopent-2-en-1-one compound 2 failed (see Table 5), both the vinylboronic acid 3.7 (Table 4, entry 5) and the potassium vinyl trifluoroborate 3.7a (entry 6) could be used to produce the 2,3-disubstituted-4-oxy-cyclopentan-1-one compound of formula 10.7, useful in the synthesis of tafluprost as outlined in FIG. 6, in good yield. 2,3-Disubstituted-4-oxy-cyclopentan-1-one compounds of formula 10.9a and 10.7 were further converted (as disclosed in the examples section herein) to the prostaglandin $F_{2\alpha}$ analogs dinoprost (see, FIG. 5) or tafluprost (see, FIG. 6), respectively, demonstrating the applicability and usefulness of the current invention to the preparation of prostaglandin drug precursors.

amount of 2-substituted-4-oxy-cyclopent-2-en-1-one compounds of formula II is sufficient to result in the high yielding conversion of 2-substituted-4-oxy-cyclopent-2-en-1-one compounds of formula II and vinylboron compounds III to 2,3-disubstituted-4-oxy-cyclopentan-1-one compounds of formula I. In contrast, the conventional organo-copper chemistry of the two-component approach requires stoichiometric amounts of the transition metal, Cu(I), and in

TABLE 5

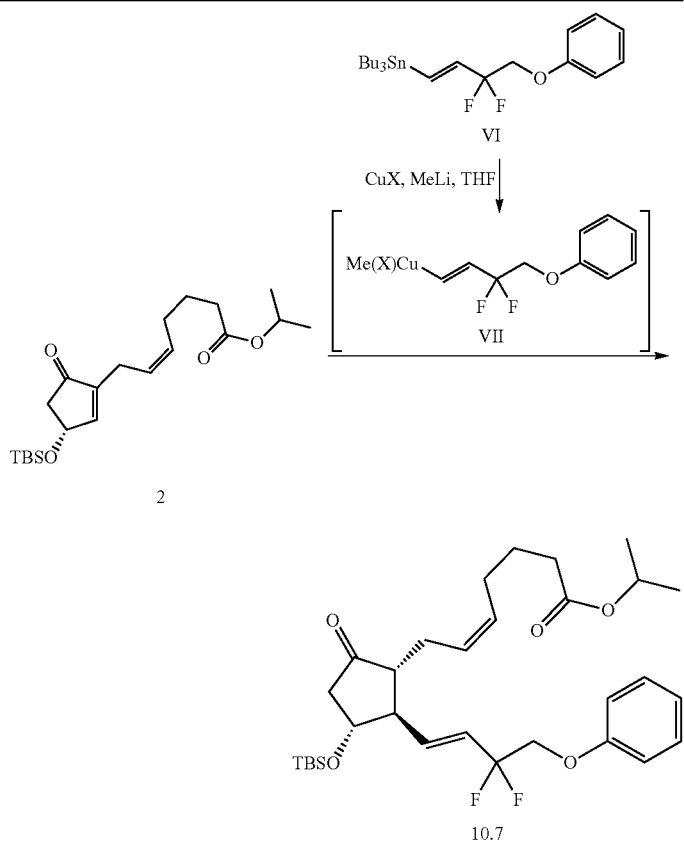

| Entry | 1 | 2 | 3 |
|---|---|---|---|
| CuX (mole equivalent with respect to VI) | CuCN, 1 | CuI, 1.1 | CuI, 1.1 |
| MeLi (mole equivalent with respect to VI) | 2.2 | 1 | 1.5 |
| Temp. for synthesis of VII | −5° C. for 1.5 h | −5° C. for 1.5 h | −5° C. for 1.5 h |
| Additive for reaction of VII and 2 | none | TMSI | TMSI |
| Temp. for reaction of VII and 2 | −55° C. for 2 h | −55° C. for 2 h | −55° C. for 2 h |
| Result | No 10.7 detected. Unreacted 2 was recovered. | No 10.7 detected. Unreacted 2 was recovered. | No 10.7 detected. Unreacted 2 was recovered. |

The reaction of the vinylboron compounds III with the 2-substituted-4-oxy-cyclopent-2-en-1-one compounds of formula II in the 1,4-conjugate addition reaction step only requires catalytic (i.e., substoichiometric) amounts of the metal additive (e.g., a rhodium compound, a cobalt compound, a nickel compound or combinations thereof). For example, typically 3 mole percent of the rhodium dimer, [RhCl(1,5-cyclooctadiene)]$_2$, with respect to the mole amount of 2-substituted-4-oxy-cyclopent-2-en-1-one compounds of formula II is sufficient to result in the high yielding conversion of 2-substituted-4-oxy-cyclopent-2-en-1-one compounds of formula II and vinylboron compounds III to 2,3-disubstituted-4-oxy-cyclopentan-1-one compounds of formula I. In contrast, the conventional organo-copper chemistry of the two-component approach requires stoichiometric amounts of the transition metal, Cu(I), and in some cases Zr(IV), and the metals Li(I), and commonly Sn(IV), all in stoichiometric amounts. In the invention disclosed herein, boron conveniently takes the place of Cu(I), and Sn(IV) or Zr(IV), and/or Li(I) metals of the conventional two-component approach and therefore reduces the amount of transition metals and other metals required to make prostaglandin precursor compounds of formula I.

In some embodiments of the present invention, the rhodium compound additive used in the 1,4-conjugate addition reaction step of the vinylboron compounds III to the compound of formula II is a pre-catalyst or catalyst that is used in substoichiometric amounts and includes, but is not limited to, rhodium(I) compounds selected from the group [RhCl (1,5-cyclooctadiene)]$_2$ (i.e., chloro(1,5-cyclooctadiene)rhodium(I) dimer); [RhCl(C$_2$H$_4$)$_2$]$_2$; [RhCl(C$_2$H$_4$)$_2$]$_2$ with a diene ligand additive; [RhCl(norbornadiene)]$_2$; and [Rh (OH)(1,5-cyclooctadiene)]$_2$ (i.e., hydroxy(1,5-cyclooctadiene)rhodium(I) dimer). 1,5-Cyclooctadiene is often abbreviated as COD, and thus [RhCl(1,5-cyclooctadiene)]$_2$ is abbreviated as [RhCl(COD)]$_2$. In certain embodiments, the rhodium additive is the rhodium dimer [RhCl(1,5-cyclooctadiene)]$_2$ or the rhodium dimer [Rh(OH)(1,5-cyclooctadiene)]$_2$.

The amount of the metal additive is preferably typically less than 50 mole percent with respect to the mole amount of the compound of formula II, such as less than or equal to 12 mole percent with respect to the mole amount of the compound of formula II, or less than 10 mole percent with respect to the mole amount of the compound of formula II, or less than or equal to 6 mole percent with respect to the mole amount of the compound of formula II, or less than or equal to 5 mole percent with respect to the mole amount of the compound of formula II.

Any suitable basic additive can be used in the process of the invention. Examples of suitable basic additives used in the 1,4-conjugate addition reaction step include, but are not limited to, KHF$_2$, t-BuOLi, t-BuONa, t-BuOK, K$_3$PO$_4$, K$_2$CO$_3$, Cs$_2$CO$_3$, LiOH, NaOH, KOH, CsOH, KF, CsF, NaHCO$_3$, KH$_2$PO$_4$, 1,3-diaminopropane, t-BuNH$_2$, i-Pr$_2$NH, piperidine, Et$_3$N, 2,6-lutidine, and combinations thereof. In certain embodiments, the basic additive is a hydroxide. In particular embodiments, the hydroxide is potassium hydroxide. Without intending to be bound by theory, it is believed that the basic additive acts upon the metal additive to convert it from a pre-catalyst into an active catalyst, although the basic additive may also serve other roles in the reaction. For example, it has been reported that rhodium(I) chloride salts are converted by hydroxide compounds into rhodium(I) hydroxides, and that these later compounds are catalytically active and can catalyze the addition reactions of vinylboron compounds to activated olefinic compounds, such as α,β-unsaturated carbonyl compounds (*J. Am. Chem. Soc.* 2002, 124, 5052-5058). The amount of the basic additive is preferably equimolar with respect to the metal additive, or greater than equimolar with respect to the metal additive.

Various combinations of different solvents, basic additives and reaction temperatures can result in significantly different yields of 2,3-disubstituted-4-oxy-cyclopentan-1-one compounds of formula I and levels of the 2,3,4-trisubstituted-cyclopentan-1-one degradation products of formula VIII. A person skilled in the art will understand that for each 2-substituted-4-oxy-cyclopent-2-en-1-one compound of formula II and vinylboron compound III, optimisation of the relative amount and type of basic additive, the relative amount and type of metal additive, the relative amount and type of solvent and the reaction temperature might be required to identify the conditions furnishing the best yields of 2,3-disubstituted-4-oxy-cyclopentan-1-one compounds of formula I.

In some embodiments, the reaction yield of 2,3-disubstituted-4-oxy-cyclopentan-1-one compounds of formula I can be increased by the portionwise addition of vinylboron compounds of formula III and/or the portionwise addition of the metal additive. For example, Table 1, entries 4-7 show that different permutations of the total amount and the number of and the amounts of each portionwise addition of boronic acid 3.1 and [RhCl(1,5-cyclooctadiene)]$_2$ resulted in different yields of the 2,3-disubstituted-4-oxy-cyclopentan-1-one compound 10.1.

In some embodiments of the present invention, R$^2$ of the compound of formula I and the compound of formula II is a hydroxyl-protecting group. Examples of hydroxyl-protecting groups include, but are not limited to, tetrahydropyranyl (THP), methoxymethyl (MOM), [2-(trimethylsilyl)ethoxy]methyl (SEM), trialkylsilyl, triarylsilyl, diarylalkylsilyl, benzyl, p-methoxybenzyl (PMB), alkylcarbonyl, arylcarbonyl and allyl. In certain embodiments, the hydroxyl-protecting group is a trialkylsilyl group. In some embodiments, trialkylsilyl is tert-butyldimethylsilyl (TBS).

In some embodiments of the present invention, the 2-substituted-4-oxy-cyclopent-2-en-1-one compound of formula II is IIa or IIb where R$^2$ is hydrogen or a hydroxyl-protecting group defined as above and R$^6$ is a radical selected from the group including H, methyl, ethyl, propyl, isopropyl, butyl, isobutyl, tert-butyl, trimethylsilyl, triethylsilyl, triisopropylsilyl, tent-butyldimethylsilyl and benzyl.

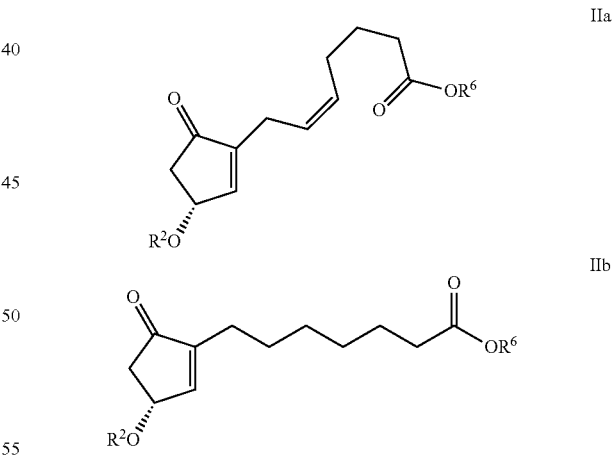

In further embodiments of the present invention, 2-substituted-4-oxy-cyclopent-2-en-1-one compound of formula II is IIa where R$^2$ is hydrogen and R$^6$ is isopropyl (see Table 6, entry 4). In other embodiments of the present invention (see Table 6), 2-substituted-4-oxy-cyclopent-2-en-1-one compound of formula II is selected from the group IIba where R$^2$ is tert-butyldimethylsilyl (TBS) and R$^6$ is methyl (entry 1), IIbb where R$^2$ is tetrahydropyranyl (THP) and R$^6$ is methyl (entry 2), and IIbc where R$^2$ is allyl and R$^6$ is methyl (entry 3).

TABLE 6

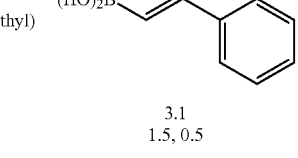

| Entry | IIa or IIb (R², R⁶) | Vinylboron compound III (mole equivalents[b]) | [RhCl(COD)]₂ (mole equivalent[b]) | Base | Time | Yield compound Ia or Ib |
|---|---|---|---|---|---|---|
| 1 | IIba (TBS, methyl) | 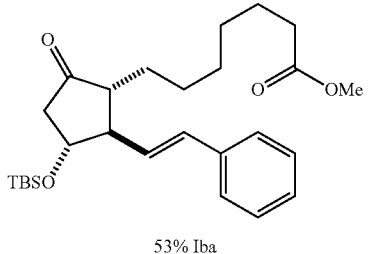 [SMILES: COC(=O)CCCCCC[C@H]1C(=O)C[C@@H](O[Si](C)(C)C(C)(C)C)[C@@H]1/C=C/c1ccccc1] 3.1 1.5, 0.5 | 1.5, 1.5 | 0.2 | 3 h, 2 h | 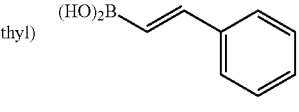 53% Iba |
| 2 | IIbb (THP, methyl) | 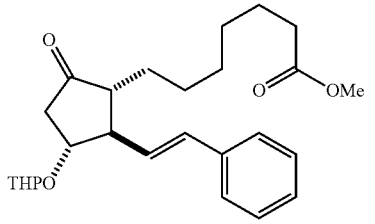 3.1 1.5, 1.0 | 1.5, 1.5 | 0.2 | 3 h, 2 h | 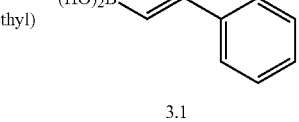 31% Ibb |
| 3 | IIbc (allyl, methyl) | 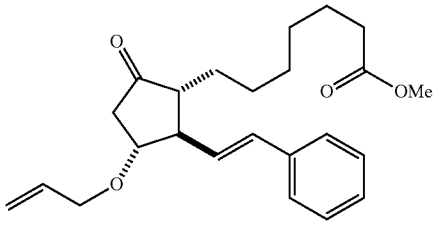 3.1 1.5, 0.5 | 1.5, 1.5 | 0.2 | 5 h, 1 h | 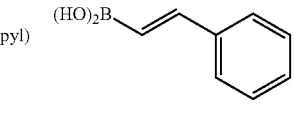 2% Ibc |
| 4 | IIaa (H, isopropyl) | 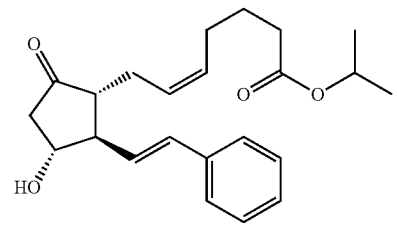 3.1 1.5, 0.5 | 1.5, 1.5 | 0.2 | 5 h, 1 h |  39% Iaa |

[a]μw indicates that the reaction solution was irradiated with microwaves. The stated temperature is that reported by the microwave reactor.

[b]When two values appear separated by a comma, this indicates the portionwise addition of the additive and/or reagent. The corresponding comma between the time units in the column for time indicates the time period following each of the corresponding additions of additive.

In some embodiments of the present invention, the radicals $R^3$, $R^4$, and/or $R^5$ of the compound of formula I and the compound of formula III possess one or more hydroxyl groups. In some embodiments, the aforementioned hydroxyl groups can be protected. Suitable hydroxyl-protecting group include, but are not limited to, tetrahydropyranyl (THP), methoxymethyl (MOM), [2-(trimethylsilyl)ethoxy]methyl (SEM), trialkylsilyl, triarylsilyl, diarylalkylsilyl, benzyl, 4-methoxybenzyl (PMB), alkylcarbonyl, arylcarbonyl and allyl. In certain embodiments, the protecting group is a trialkylsilyl group. In some embodiments, trialkylsilyl is tert-butyldimethylsilyl (TBS). Table 7, entries 1-8, show four different hydroxyl-protected vinylboronic acid derivatives 3.8a (tert-butyldimethylsilyl protected; entry 1), 3.8c (benzyl protected; entry 2), 3.8e (tetrahydropyranyl protected; entry 3), and 3.8b (acetyl protected; entry 4), and four different hydroxyl-protected pinacol vinylboronate derivatives 2.8a (tert-butyldimethylsilyl protected; entry 8), 2.8c (benzyl protected; entry 7), 2.8e (tetrahydropyranyl protected; entry 5), and 2.8b (acetyl protected; entry 6). In some embodiments, the aforementioned hydroxyl group can remain unprotected, such as in the example in Table 7, entry 9 (as in vinylboronic acid 2.8).

TABLE 7

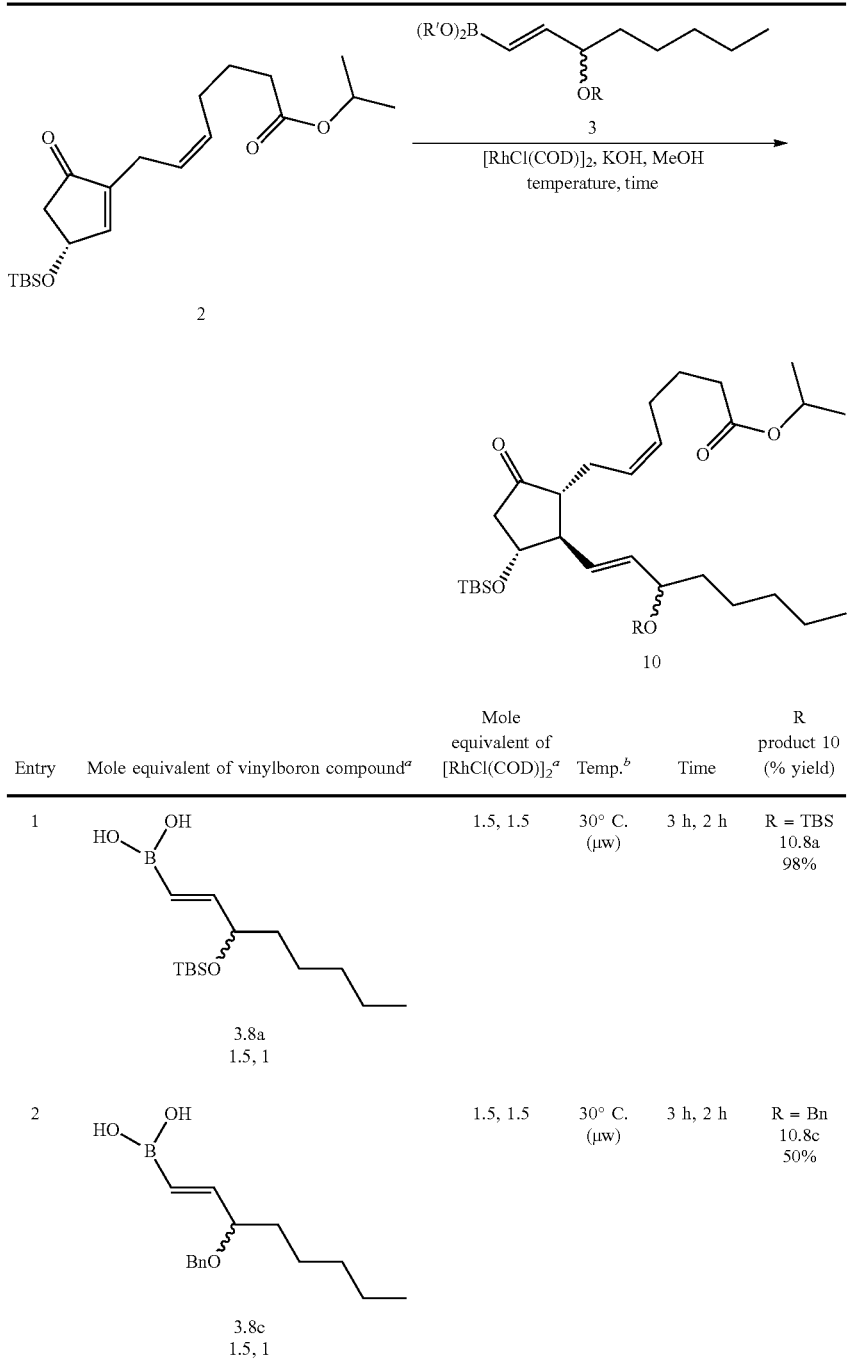

| Entry | Mole equivalent of vinylboron compound[a] | Mole equivalent of [RhCl(COD)]$_2$[a] | Temp.[b] | Time | R product 10 (% yield) |
|---|---|---|---|---|---|
| 1 | 3.8a  1.5, 1 | 1.5, 1.5 | 30° C. (μw) | 3 h, 2 h | R = TBS 10.8a 98% |
| 2 | 3.8c  1.5, 1 | 1.5, 1.5 | 30° C. (μw) | 3 h, 2 h | R = Bn 10.8c 50% |

TABLE 7-continued
| | | | | | |
|---|---|---|---|---|---|
| 3 | 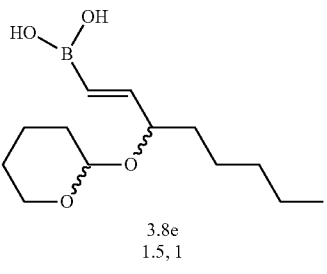 [SMILES: CCCCCC(/C=C/B(O)O)OC1CCCCO1]<br>3.8e<br>1.5, 1 | 1.5, 1.5 | 30° C.<br>(μw) | 3 h, 2 h | R = THP<br>10.8e<br>63% |
| 4 | 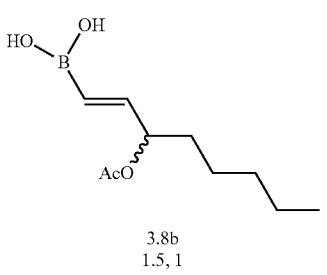<br>3.8b<br>1.5, 1 | 1.5, 1.5 | 30° C.<br>(μw) | 3 h, 2 h | R = Ac<br>10.8b<br>24% |
| 5 | 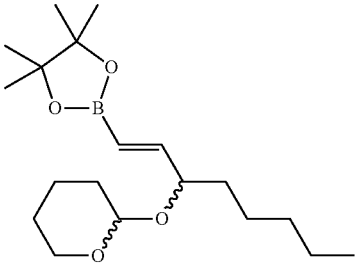<br>2.8e<br>1.5, 1 | 1.5, 1.5 | 30° C.<br>(μw) | 3 h, 2 h | R = THP<br>10.8e<br>63% |
| 6 | 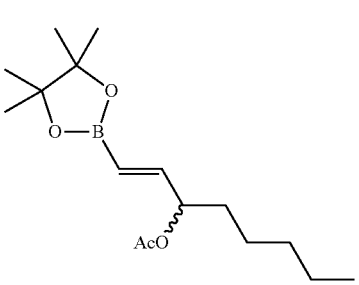<br>2.8b<br>1.5, 1 | 1.5, 1.5 | 30° C.<br>(μw) | 3 h, 2 h | R = Ac<br>10.8b<br>17% |
| 7 | 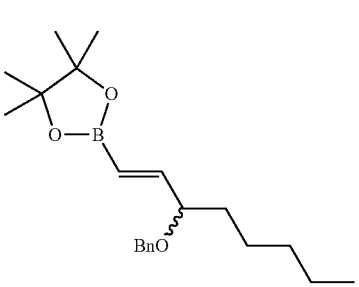<br>2.8c<br>1.5, 1 | 1.5, 1.5 | 30° C.<br>(μw) | 3 h, 2 h | R = Bn<br>10.8c<br>36% |

TABLE 7-continued

| 8 | ![structure 2.8a with TBSO and pinacol boronate] 2.8a 1.5, 0.5, 0.5, 0.5 | 1.5, 1.5, 1.5, 1.5 | 30° C. (μw) | 3 h, 2 h, 2 h, 2 h | R = TBS 10.8a 67% |
|---|---|---|---|---|---|
| 9 | ![structure 2.8 with HO and boronic acid] 2.8 1.5, 1 | 1.5, 1.5 | 30° C. (μw) | 3 h, 2 h | R = H 10.8 40% |

[a]When two or more values appear separated by a comma, this indicates the portionwise addition of the additive and/or reagent. The corresponding comma between the time units in the column for time indicates the reaction time period following each of the corresponding additions of additive.

[b]μw indicates that the reaction solution was irradiated with microwaves. The stated temperature is that reported by the microwave reactor.

The vinylboron compounds of formula III that are useful in this invention can be prepared by methods reported in the literature (*J. Am. Chem. Soc.* 2005, 127, 5766-5767; *Angew. Chem.* 2003, 42, 3399-3404; *J. Org. Chem.* 2001, 66, 5359-5365; *Angew. Chem.* 2012, 51, 9385-9388; *Org. Lett.* 2012, 14, 6104-6107; *Org. Lett* 2010, 12, 2004-2007).

For example, when $R^4$ is H, one method comprises
a) contacting the alkyne compound of formula IV

(IV)

with an organoboron reagent; and
b) converting the product from step a) to afford III. Alternatively, the vinylboron compounds of formula III can be prepared using vinyl halides as starting materials, and methods for this transformation are known in the art.

The aforementioned organoboron reagent is a hydroborane compound and is selected from the group consisting of a borane ether complex, such as $BH_3.THF$ or $BH_3.OEt_2$; a borane sulfide complex, such as $BH_3.SMe_2$; 9-borabicyclo[3.3.1]nonane; 9-borabicyclo[3.3.1]nonane dimer; pinacolborane; catecholborane; a dialkylborane such as dicyclohexylborane, disiamylborane, diisopinocampheylborane or di(isopropylprenyl)borane; and mono- and dichloroborane or mono- and dibromoborane—Lewis base complexes such as $BHCl_2.dioxane$, $BH_2Cl.OEt_2$, $BH_2Cl.SMe_2$, $BHBr_2.dioxane$, $BH_2Br.OEt_2$ or $BH_2Br.SMe_2$. The vinylboron compounds of formula III that are useful in this invention include vinylboronic acids, vinylboronic esters, vinyl N-imino diacetic acid boronates, vinyl triorganoboranes (e.g., vinyl trialkylboranes), vinyl B-organo-9-BBN compounds (e.g., vinyl B-alkyl-9-BBN compounds), vinyltrifluoroborate salts and tetravinylborate salts. In certain embodiments, the vinylboron compound is a vinylboronic acid or a vinyltrifluoroborate salt.

2-Substituted-4-oxy-cyclopent-2-en-1-one compounds of formula II useful in the process of the invention can be prepared using methods known in the art, including those reported in U.S. Pat. No. 7,897,795, *Org. Process Res. Dev.* 2012, 16, 1905-1916 and *Tetrahedron Lett.* 2003, 44, 7411-7415.

While some guidance is provided in the Examples below, one of skill in the art will appreciate the process described herein will operate under a variety of conditions relating to temperature and the solvent or solvents used (discussed above), as well as the time of reaction, and the concentration of reactants in the reaction mixture. The following Examples are illustrative of certain embodiments of the invention and should not be considered as limiting in any way.

IV. Examples

Example 1

Synthesis of isopropyl (Z)-7-[(2R,3R)-3-(tert-butyl-dimethyl-silanyloxy)-5-oxo-2-styryl-cyclopentyl]-hept-5-enoate (10.1)

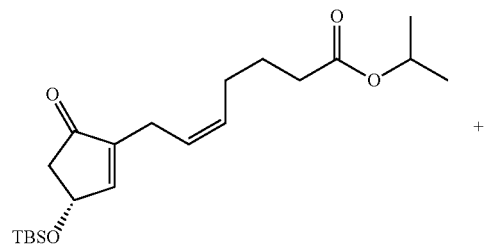

2

+

A solution of isopropyl (Z)-7-[(3R)-3-(tert-butyl-dimethyl-silanyloxy)-5-oxo-cyclopent-1-enyl]-hept-5-enoate (2) (57 mg, 0.15 mmol), trans-2-phenylvinylboronic acid (3.1) (33 mg, 0.22 mmol), [RhCl(1,5-cyclooctadiene)]$_2$ (1.1 mg, 2.2 μmol) and aq. KOH (9.5 μL, 3.0 M aq. KOH, 29 μmmol) in MeOH (1.0 mL) was stirred under microwave irradiation (CEM, Discover S; or Milestone, Startsynth; the temperature was set at 30° C.). After 5 hours, trans-2-phenylvinylboronic acid (3.1) (11 mg, 74 μmol) and [RhCl(1,5-cyclooctadiene)]$_2$ (1.1 mg, 2.4 μmol) were added and the reaction mixture was stirred for another hour and was directly concentrated in vacuo. The residue was purified by column chromatography (eluting with 1:80 (v/v) acetone-hexanes) affording 10.1 (70 mg, 96%).

$[\alpha]^{27}{}_D$–57.4 (c 1.00, CHCl$_3$); $^1$H NMR (400 MHz, CDCl$_3$): δ 0.01 (s, 3H), 0.03 (s, 3H), 0.86 (s, 9H), 1.20 (d, J=6.2 Hz, 6H), 1.59-1.69 (m, 2H), 2.05 (dd, J=7.1, 14.1 Hz, 2H), 2.16-2.26 (m, 4H), 2.38-2.42 (m, 2H), 2.58-2.73 (m, 2H), 4.13 (dd, J=8.4, 16.0 Hz, 1H), 4.97 (septet, J=6.2 Hz, 1H), 5.32-5.46 (m, 2H), 6.05 (dd, J=8.6, 15.8 Hz, 1H), 6.50 (d, J=15.8 Hz, 1H), 7.22-7.26 (m, 1H), 7.27-7.37 (m, 4H); $^{13}$C NMR (125 MHz, CDCl$_3$): δ –4.8 (CH$_3$), –4.7 (CH$_3$), 18.1 (C), 21.8 (CH$_3$), 24.8 (CH$_2$), 25.1 (CH$_2$), 25.7 (CH), 26.7 (CH$_2$), 34.1 (CH$_2$), 47.6 (CH$_2$), 54.1 (CH), 54.4 (CH), 67.4 (CH), 73.0 (CH), 126.1 (CH), 126.5 (CH), 127.4 (CH), 128.6 (CH), 129.8 (CH), 131.0 (CH), 132.9 (CH), 137.1 (C), 173.1 (C), 214.7 (C); HRMS (ESI-QTOF) calculated for [C$_{29}$H$_{44}$O$_4$Si+H]$^+$=485.3081, found 485.3064; FTIR (KBr, neat) 2935, 2861, 1736, 1593, 1459, 1372, 1250, 1107, 838, 745 cm$^{-1}$.

Example 2

Synthesis of Isopropyl (Z)-7-[(1R,2R)-5-oxo-2,3-distyryl-cyclopent-3-enyl]-hept-5-enoate (6.1)

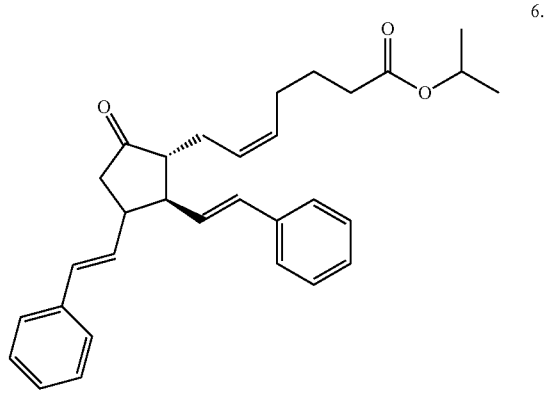

The degradation product 6.1 standard can be prepared using the following procedure: A solution of 10.1 (16 mg, 33 μmol, trans-2-phenylvinylboronic acid (3.1) (9.2 mg, 62 μmol, [RhCl(1,5-cyclooctadiene)]$_2$ (1.1 mg, 2.25 μmol, 5.6 mol %) and aq. KOH (9.5 μL, 3.0 M aq. KOH, 28.5 μmol) in MeOH (1 mL) was stirred at 60° C. After 12 hours, the mixture was directly concentrated in vacuo. The residue was purified by column chromatography (eluting with 1:80 (v/v) acetone-hexanes) affording the title compound 6.1 (13 mg, 86%).

$[\alpha]^{24}{}_D$–149.5 (c 0.46, CHCl$_3$)); $^1$H NMR (400 MHz, CDCl$_3$): δ 1.20 (d, J=6.4, 6H), 1.58-1.72 (m, 2H), 1.98-2.12 (m, 2H), 2.13-2.34 (m, 4H), 2.36-2.58 (m, 3H), 2.64-2.85 (m, 2H), 4.97 (septet, J=6.4 Hz, 1H), 5.31-5.50 (m, 2H), 6.06-6.22 (m, 2H), 6.43 (dd, J=11.6, 16.0 Hz, 2H), 7.17-7.36 (m, 10H); $^{13}$C NMR (100 MHz, CDCl$_3$): δ 21.8 (CH$_3$), 24.8 (CH$_2$), 25.0 (CH$_2$), 26.7 (CH$_2$), 30.9 (CH$_2$), 34.1 (CH$_2$), 44.4 (CH), 51.7 (CH), 55.5 (CH), 67.4 (CH), 77.2 (CH), 126.18 (CH), 126.22 (CH), 126.5 (CH), 127.4 (CH), 127.5 (CH), 128.5 (CH), 128.6 (CH), 130.3 (CH), 131.0 (CH), 131.2 (CH), 132.5 (CH), 137.0 (C), 173.1 (C), 216.7 (C); HRMS (ESI-TOF) calculated for [C$_{31}$H$_{36}$O$_3$+H]$^+$=457.2737, found 457.2738; FTIR (KBr, neat) 3446, 2975, 1730, 1640, 1443, 1375, 1217, 1164, 1102, 963 cm$^{-1}$.

Example 3

Synthesis of isopropyl (Z)-7-{(2R,3R),-3-(tert-butyl-dimethyl-silanyloxy)-2-[2-(4-methoxy-phenyl)-vinyl]-5-oxo-cyclopentyl}-hept-5-enoate (10.2)

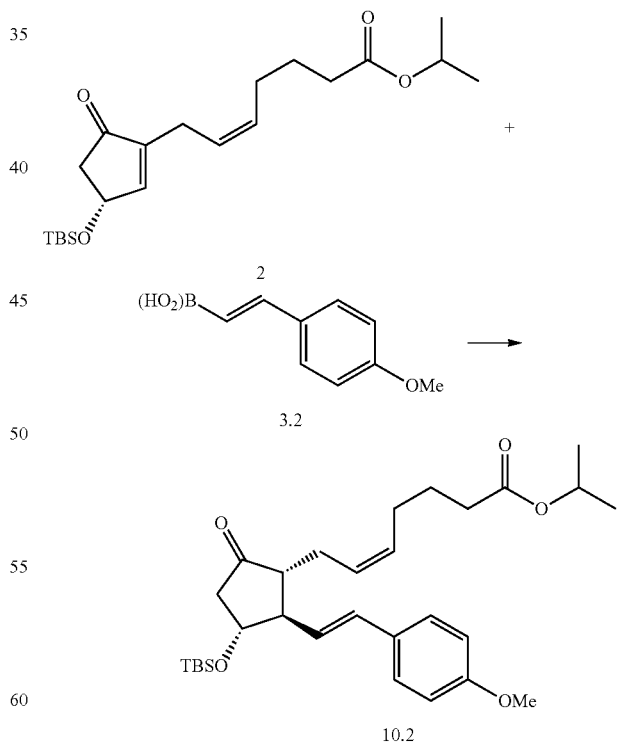

Following the procedure described in Example 1 the title compound was synthesized using trans-2-(4-methoxy-phenyl)-vinylboronic acid (3.2). The crude product mixture was then purified by column chromatography (eluting with 1:80

(v/v) acetone-hexanes) affording isopropyl (Z)-7-{(2R,3R),-3-(tert-butyl-dimethyl-silanyloxy)-2-[2-(4-methoxy-phenyl)-vinyl]-5-oxo-cyclopentyl}-hept-5-enoate (10.2, 72 mg, 93%).

$[\alpha]^{22}_D$ -50.6 (c 1.00, CHCl$_3$); $^1$H NMR (400 MHz, CDCl$_3$): δ 0.00 (s, 3H), 0.02 (s, 3H), 0.85 (s, 9H), 1.20 (d, J=6.3 Hz, 6H), 1.60-1.68 (m, 2H), 2.05 (dd, J=7.0, 14.1 Hz, 2H), 2.14-2.25 (m, 4H), 2.36-2.39 (m, 2H), 2.55-2.71 (m, 2H), 3.81 (s, 3H), 4.09 (dd, J=8.5, 15.8 Hz, 1H), 4.97 (septet, J=6.3 Hz, 1H), 5.32-5.45 (m, 2H), 5.89 (dd, J=8.4, 15.6 Hz, 1H), 6.44 (d, J=15.6 Hz, 1H), 6.85 (d, J=8.6 Hz, 2H), 7.28 (d, J=8.6 Hz, 2H); $^{13}$C NMR (100 MHz, CDCl$_3$): δ -4.8 (CH$_3$), -4.6 (CH$_3$), 18.0 (C), 21.8 (CH$_3$), 24.8 (CH$_2$), 25.1 (CH$_2$), 25.7 (CH$_3$), 26.6 (CH$_2$), 34.1 (CH$_2$), 47.6 (CH$_2$), 54.1 (CH), 54.4 (CH), 55.2 (CH$_3$), 67.4 (CH), 73.1 (CH), 114.0 (CH), 126.5 (CH), 127.2 (CH), 127.5 (CH), 129.9 (C), 130.9 (CH), 132.3 (CH), 159.0 (C), 173.1 (C), 214.9 (C); HRMS (ESI-QTOF) calculated for [C$_{30}$H$_{46}$O$_5$Si+H]$^+$=515.3187, found 515.3182; FTIR (KBr, neat) 2939, 2863, 1737, 1604, 1512, 1463, 1371, 1246, 1166, 1109 cm$^{-1}$.

Example 4

Synthesis of isopropyl (Z)-7-[(2R,3R)-3-(tert-butyl-dimethyl-silanyloxy)-5-oxo-2-(2-p-tolyl-vinyl)-cyclopentyl]-hept-5-enoate (10.3)

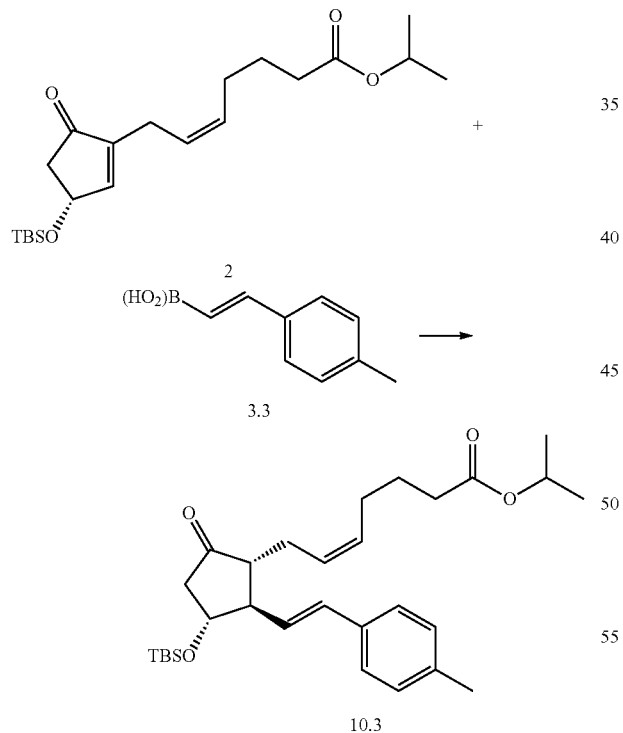

Following the procedure described in Example 1 the title compound was synthesized using trans-2-p-tolyl-vinylboronic acid (3.3). The crude product mixture was then purified by column chromatography (eluting with 1:80 (v/v) acetone-hexanes) affording isopropyl (Z)-7-[(2R,3R)-3-(tert-butyl-dimethyl-silanyloxy)-5-oxo-2-(2-p-tolyl-vinyl)-cyclopentyl]-hept-5-enoate (10.3, 71 mg, 95%).

$[\alpha]^{23}_D$ -40.2 (c 1.00, CHCl$_3$); $^1$H NMR (400 MHz, CDCl$_3$): δ 0.00 (s, 3H), 0.02 (s, 3H), 0.85 (s, 9H), 1.20 (d, J=6.2 Hz, 6H), 1.64 (quintet, J=7.6 Hz, 2H), 2.04 (dd, J=7.3, 14.2 Hz, 2H), 2.13-2.26 (m, 4H), 2.34 (s, 3H), 2.38-2.40 (m, 2H), 2.57-2.72 (m, 2H), 4.11 (dd, J=8.0, 15.6 Hz, 1H), 4.97 (septet, J=6.2 Hz, 1H), 5.31-5.45 (m, 2H), 5.98 (dd, J=8.7, 15.7 Hz, 1H), 6.46 (d, J=15.7 Hz, 1H), 7.13 (d, J=8.0 Hz, 2H), 7.25 (d, J=8.0 Hz, 2H); $^{13}$C NMR (100 MHz, CDCl$_3$): δ -4.8 (CH$_3$), -4.7 (CH$_3$), 18.0 (C), 21.1 (CH$_3$), 21.8 (CH$_3$), 24.8 (CH$_2$), 25.0 (CH$_2$), 25.7 (CH$_3$), 26.6 (CH$_2$), 34.1 (CH$_2$), 47.6 (CH$_2$), 54.1 (CH), 54.4 (CH), 67.3 (CH), 73.0 (CH), 126.0 (CH), 126.5 (CH), 128.7 (CH), 129.3 (C), 130.9 (CH), 132.7 (CH), 134.3 (C), 137.1 (C), 173.1 (C), 214.8 (C); HRMS (ESI-QTOF) calculated for [C$_{30}$H$_{46}$O$_4$Si+H]$^+$=499.3238, found 499.3244; FTIR (KBr, neat) 2938, 2863, 1737, 1509, 1463, 1372, 1250, 1110, 964, 841 cm$^{-1}$.

Example 5

Synthesis of isopropyl (Z)-7-[(2R,3R)-3-(tert-butyl-dimethyl-silanyloxy)-5-oxo-2-(2-m-tolyl-vinyl)-cyclopentyl]-hept-5-enoate (10.4)

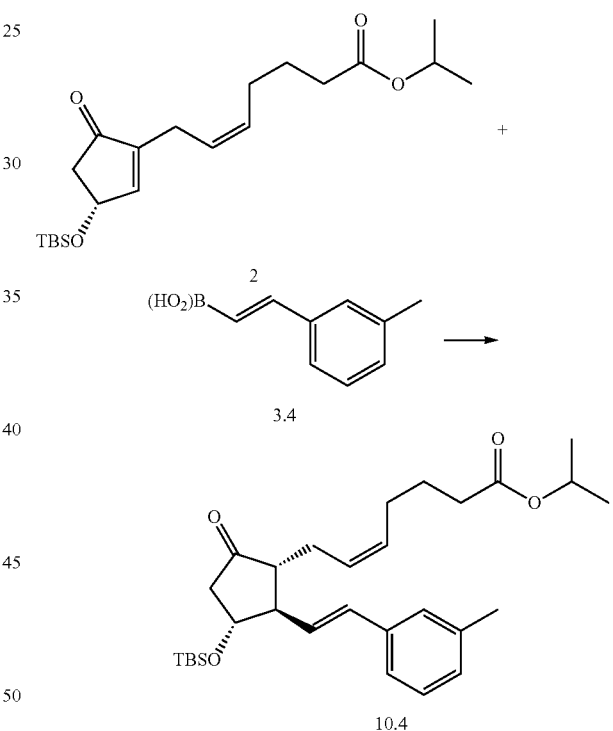

Following the procedure described in Example 1 the title compound was synthesized using trans-2-m-tolyl-vinylboronic acid (3.4). The crude product mixture was then purified by column chromatography (eluting with 1:80 (v/v) acetone-hexanes) affording isopropyl (Z)-7-[(2R,3R)-3-(tert-butyl-dimethyl-silanyloxy)-5-oxo-2-(2-m-tolyl-vinyl)-cyclopentyl]-hept-5-enoate (10.4, 73 mg, 98%).

$[\alpha]^{23}_D$ -51.1 (c 1.00, CHCl$_3$); $^1$H NMR (400 MHz, CDCl$_3$): δ 0.01 (s, 3H), 0.03 (s, 3H), 0.86 (s, 9H), 1.20 (d, J=6.4 Hz, 6H), 1.65 (quintet, J=7.6 Hz, 2H), 2.05 (dd, J=7.0, 14.2 Hz, 2H), 2.15-2.26 (m, 4H), 2.35 (s, 3H), 2.36-2.41 (m, 2H), 2.58-2.73 (m, 2H), 4.12 (dd, J=8.4, 16.0 Hz, 1H), 4.97 (septet, J=6.4 Hz, 1H), 5.32-5.46 (m, 2H), 6.03 (dd, J=8.6, 15.8 Hz, 1H), 6.47 (d, J=15.8 Hz, 1H), 7.06 (d, J=7.3 Hz, 1H), 7.15-7.23 (m, 3H); $^{13}$C NMR (100 MHz, CDCl$_3$): δ -4.8

($CH_3$), −4.6 ($CH_3$), 18.0 (C), 21.4 ($CH_3$), 21.8 ($CH_3$), 24.8 ($CH_2$), 25.1 ($CH_2$), 25.7 ($CH_3$), 26.7 ($CH_2$), 34.1 ($CH_2$), 47.6 ($CH_2$), 54.1 (CH), 54.3 (CH), 67.4 (CH), 73.1 (CH), 123.2 (CH), 126.5 (CH), 126.9 (CH), 128.2 (CH), 128.5 (CH), 129.5 (CH), 131.0 (CH), 133.0 (CH), 137.0 (C), 138.1 (C), 173.1 (C), 214.8 (C); HRMS (ESI-QTOF) calculated for $[C_{30}H_{46}O_4Si+H]^+$=499.3238, found 499.3242; FTIR (KBr, neat) 2939, 2863, 1737, 1600, 1463, 1375, 1253, 1112, 971, 884 $cm^{-1}$.

Example 6

Synthesis of isopropyl (Z)-7-[(2R,3R)-3-(tert-butyl-dimethyl-silanyloxy)-2-(2-methyl-prop-1-enyl)-5-oxo-cyclopentyl]-hept-5-enoate (10.5)

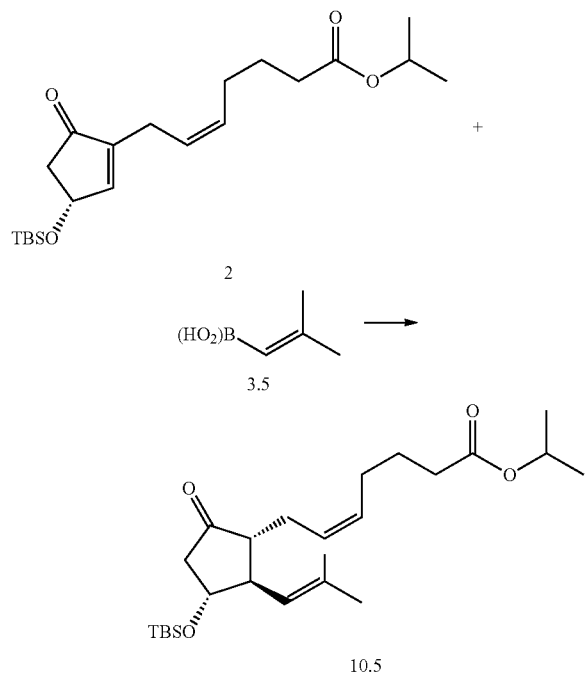

Following the procedure described in Example 1 the title compound was synthesized using 2-methyl-propenylboronic acid (3.5). The crude product mixture was then purified by column chromatography (eluting with 1:80 (v/v) acetone-hexanes) affording isopropyl (Z)-7-[(2R,3R)-3-(tert-butyl-dimethyl-silanyloxy)-2-(2-methyl-prop-1-enyl)-5-oxo-cyclopentyl]-hept-5-enoate (10.5, 65 mg, 99%).

$[\alpha]^{23}_D$−68.2 (c 1.00, $CHCl_3$); $^1H$ NMR (400 MHz, $CDCl_3$): δ 0.00 (s, 3H), 0.01 (s, 3H), 0.86 (s, 9H), 1.22 (d, J=6.4 Hz, 6H), 1.63-1.68 (m, 5H), 1.74 (s, 3H), 1.92-1.99 (m, 1H), 2.01-2.07 (m, 2H), 2.13-2.21 (m, 1H), 2.22-2.27 (m, 2H), 2.27-2.33 (m, 2H), 2.58-2.65 (m, 1H), 2.67-2.76 (m, 1H), 3.95 (dd, J=8.0, 15.6 Hz, 1H), 4.92 (d, J=9.6 Hz, 1H), 5.00 (septet, J=6.4 Hz, 1H), 5.30-5.43 (m, 2H); $^{13}C$ NMR (100 MHz, $CDCl_3$): δ −5.0 ($CH_3$), 18.0 (C), 18.7 ($CH_3$), 21.8 ($CH_3$), 24.8 ($CH_2$), 25.0 ($CH_2$), 25.6 ($CH_3$), 25.8 ($CH_3$), 26.5 ($CH_2$), 34.1 ($CH_2$), 47.6 ($CH_2$), 49.4 (CH), 55.2 (CH), 67.4 (CH), 73.6 (CH), 125.4 (CH), 127.0 (CH), 130.4 (CH), 135.4 (C), 173.1 (C), 215.6 (C); HRMS (ESI-QTOF) calculated for $[C_{25}H_{44}O_4Si+H]^+$=437.3082, found 437.3096; FTIR (KBr, neat) 2937, 2855, 1738, 1463, 1373, 1248, 1150, 1108, 880, 834 $cm^{-1}$.

Example 7

Synthesis of isopropyl (Z)-7-[(2R,3R)-3-(tert-butyl-dimethyl-silanyloxy)-2-(trans-oct-1-enyl)-5-oxo-cyclopentyl]-hept-5-enoate (10.6)

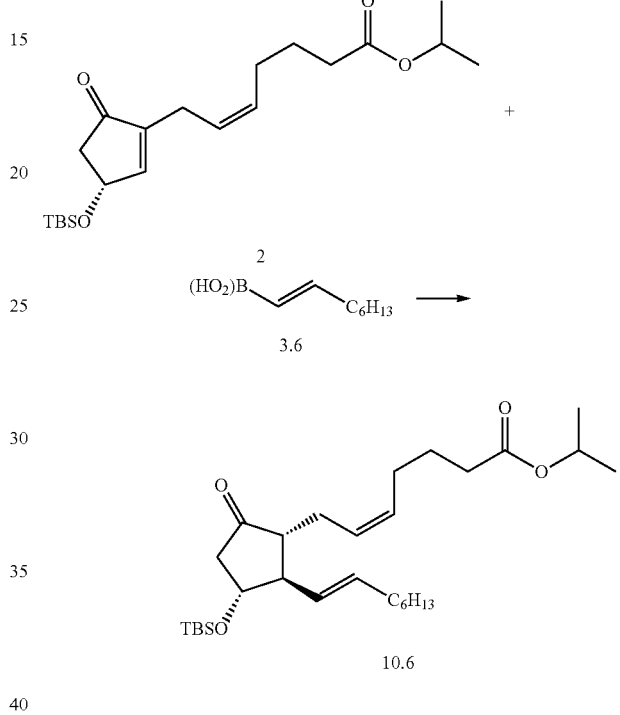

Following the procedure described in Example 1 the title compound was synthesized using trans-oct-1-enylboronic acid (3.6). The crude product mixture was then purified by column chromatography (eluting with 1:80 (v/v) acetone-hexanes) affording isopropyl (Z)-7-[(2R,3R)-3-(tert-butyl-dimethyl-silanyloxy)-2-(trans-oct-1-enyl)-5-oxo-cyclopentyl]-hept-5-enoate (10.6, 69 mg, 93%).

$[\alpha]^{23}_D$−54.5 (c 1.00, $CHCl_3$); $^1H$ NMR (400 MHz, $CDCl_3$): δ 0.02 (s, 3H), 0.03 (s, 3H), 0.86 (s, 9H), 1.21 (d, J=6.4 Hz, 6H), 1.26-1.36 (m, 10H), 1.62-1.69 (m, 3H), 1.97-2.07 (m, 5H), 2.09-2.16 (m, 1H), 2.24 (t, J=7.6 Hz, 2H), 2.26-2.43 (m, 3H), 2.61 (ddd, J=1.1, 7.14, 18.3 Hz, 1H), 3.98 (dd, J=8.0, 15.6 Hz, 1H), 4.99 (septet, J=6.4 Hz, 1H), 5.26 (dd, J=8.4, 15.2 Hz, 1H), 5.30-5.42 (m, 2H), 5.50-5.58 (m, 1H); $^{13}C$ NMR (100 MHz, $CDCl_3$): δ 4.7 ($CH_3$), 14.1 ($CH_3$), 18.1 (C), 21.8 ($CH_3$), 22.6 ($CH_2$), 24.8 ($CH_2$), 24.9 ($CH_2$), 25.7 ($CH_3$), 26.6 ($CH_2$), 28.9 ($CH_2$), 29.3 ($CH_2$), 31.7 ($CH_2$), 32.6 ($CH_2$), 34.1 ($CH_2$), 47.6 ($CH_2$), 53.5 (CH), 54.2 (CH), 67.3 (CH), 73.1 (CH), 126.8 (CH), 129.6 (CH), 130.6 (CH), 134.0 (CH), 173.1 (C), 215.3 (C); HRMS (ESI-QTOF) calculated for $[C_{29}H_{52}O_4Si+H]^+$=493.3708, found 493.3702; FTIR (KBr, neat) 2930, 2860, 1739, 1462, 1371, 1250, 1111, 968, 839, 775 $cm^{-1}$.

Example 8

Synthesis of isopropyl (Z)-7-[(2R,3R)-3-(tert-butyl-dimethyl-silanyloxy)-2-(trans-3,3-difluoro-4-phenoxy-but-1-enyl)-5-oxo-cyclopentyl]-hept-5-enoate (10.7)

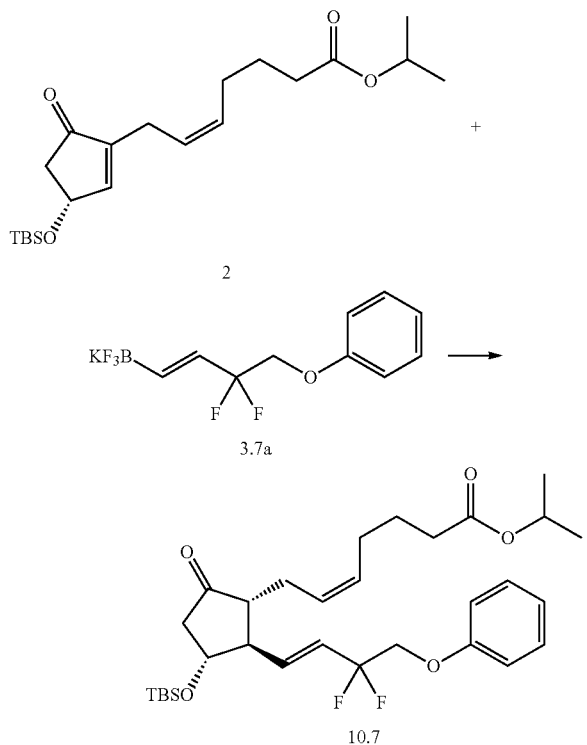

Following the procedure described in Example 1 the title compound was synthesized using potassium trans-3,3-difluoro-4-phenoxy-but-1-enyltrifluoroborate (3.7a). The crude product mixture was then purified by column chromatography (eluting with 1:80 (v/v) acetone-hexanes) affording isopropyl (Z)-7-[(2R,3R)-3-(tert-butyl-dimethyl-silanyloxy)-2-(trans-3,3-difluoro-4-phenoxy-but-1-enyl)-5-oxo-cyclopentyl]-hept-5-enoate (10.7, 52 mg, 61%).

$[\alpha]^{24}_D$ -45.0 (c 1.00, CHCl$_3$); $^1$H NMR (600 MHz, CDCl$_3$): δ 0.03 (s, 3H), 0.04 (s, 3H), 0.86 (s, 9H), 1.21 (d, J=6.3 Hz, 6H), 1.58-1.63 (m, 2H), 2.01 (dd, J=7.2, 14.4 Hz, 2H), 2.11-2.22 (m, 4H), 2.35-2.38 (m, 2H), 2.57 (dd, J=8.7, 20.2 Hz, 1H), 2.66 (dd, J=1.0, 7.2 Hz, 1H), 4.09 (dd, J=8.4, 16.2 Hz, 1H), 4.16-4.21 (m, 2H), 4.98 (septet, J=6.3 Hz, 1H), 5.28-5.32 (m, 1H), 5.37-5.41 (m, 1H), 5.85-5.91 (m, 1H), 6.11 (m, 1H), 6.91 (d, J=8.0 Hz, 2H), 7.00 (t, J=7.4 Hz, 1H), 7.30 (dd, J=7.4, 8.0 Hz, 2H); $^{13}$C NMR (150 MHz, CDCl$_3$): δ -4.8 (CH$_3$), -4.7 (CH$_3$), 18.0 (C), 21.8 (CH$_3$), 24.7 (CH$_2$), 25.0 (CH$_2$), 25.7 (CH$_3$), 26.6 (CH$_2$), 34.0 (CH$_2$), 47.4 (CH$_2$), 53.0 (CH), 53.8 (CH), 67.4 (CH), 69.4 (t, J=35.0 Hz, CH$_2$), 72.3 (CH), 114.7 (CH), 117.9 (t, J=238.5 Hz, C), 121.8 (CH), 125.5 (t, J=24.8 Hz, CH), 126.0 (CH), 129.6 (CH), 131.4 (CH), 136.9 (t, J=9.0 Hz, CH), 157.9 (C), 173.0 (C), 213.6 (C); HRMS (ESI-QTOF): calculated for $[C_{31}H_{46}F_2O_5Si+NH_4]^+$=586.3421, found 582.3406; FTIR (KBr, neat) 2939, 2863, 1737, 1592, 1490, 1463, 1375, 1307, 1250, 1158 cm$^{-1}$.

Example 9

Synthesis of (Z)-isopropyl 7-((1R,2R,3R)-3-((tert-butyldimethylsilyl)oxy)-2-((E)-2-methylstyryl)-5-oxocyclopentyl)hept-5-enoate (10.11)

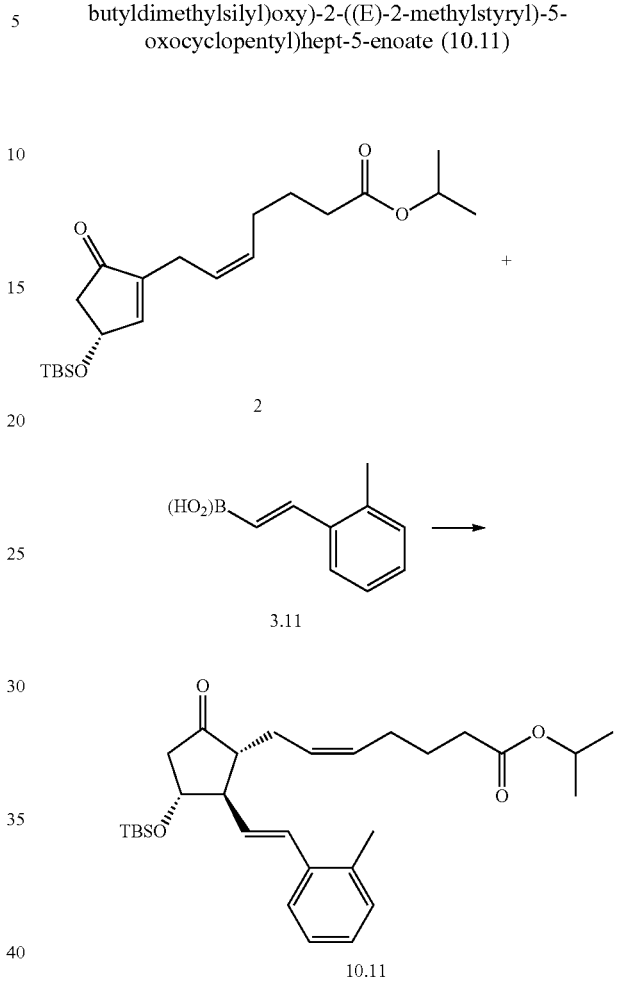

Following procedures described in Example 1, except using trans-2-o-tolyl-vinylboronic acid (3.11), the reaction crude mixture was purified by column chromatography (eluting with 1:80 (v/v) acetone-hexanes) affording the title compound 10.11 (66 mg, 88%).

$[\alpha]^{25}_D$ -53.4 (c 1.00, CHCl$_3$); $^1$H NMR (400 MHz): δ 0.03 (s, 3H), 0.04 (s, 3H), 0.87 (s, 9H), 1.20 (d, J=6.2 Hz, 6H), 1.65 (quintet, J=7.6 Hz, 2H), 2.07 (dd, J=6.4, 14.0 Hz, 2H), 2.13-2.30 (m, 4H), 2.34 (s, 3H), 2.35-2.45 (m, 2H), 2.60-2.72 (m, 2H), 4.15 (dd, J=8.6, 15.8 Hz, 1H), 4.97 (septet, J=6.2 Hz, 1H), 5.32-5.47 (m, 2H), 5.93 (dd, J=8.6, 15.6 Hz, 1H), 6.72 (d, J=15.6 Hz, 1H), 7.12-7.20 (m, 3H), 7.38-7.44 (m, 1H); $^{13}$C NMR (100 MHz): δ -4.72 (CH$_3$), 4.65 (CH$_3$), 18.0 (C), 19.7 (CH$_3$), 21.8 (CH$_3$), 24.8 (CH$_2$), 25.1 (CH$_2$), 25.7 (CH$_3$), 26.7 (CH$_2$), 34.0 (CH$_2$), 47.6 (CH$_2$), 54.4 (CH), 54.5 (CH), 67.3 (CH), 73.0 (CH), 125.5 (CH), 126.1 (CH), 126.6 (CH), 127.3 (CH), 130.2 (CH), 130.7 (CH), 130.9 (CH), 131.2 (CH), 135.1 (C), 136.2 (C), 173.0 (C), 214.7 (C); HRMS (ESI-QTOF) calculated for $[C_{30}H_{46}O_4Si+H]^+$=499.3238, found 499.3234; FTIR (KBr, neat) 3454, 2948, 1737, 1647, 1462, 1375, 1253, 1107, 969, 880 cm$^{-1}$.

Example 10

Synthesis of (Z)-isopropyl 7-((1R,2R,3R)-3-((tert-butyldimethylsilyl)oxy)-2-((E)-3-methoxystyryl)-5-oxocyclopentyl)hept-5-enoate (10.12)

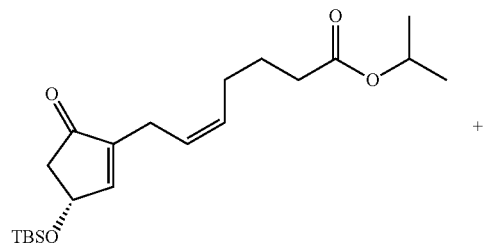

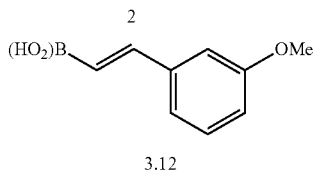

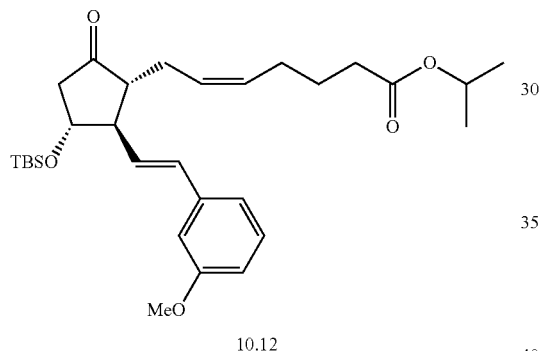

Following procedures described in Example 1, except using trans-2-(3-methoxy-phenyl)-vinylboronic acid (3.12), the reaction crude mixture was purified by column chromatography (eluting with 1:80 (v/v) acetone-hexanes) affording the title compound 10.12 (72 mg, 93%).

$[\alpha]^{25}_D$ –65.1 (c 1.00, CHCl$_3$); $^1$H NMR (400 MHz): δ 0.01 (s, 3H), 0.02 (s, 3H), 0.85 (s, 9H), 1.20 (d, J=6.2 Hz, 6H), 1.69-1.70 (m, 2H), 2.05 (dd, J=7.1, 14.1 Hz, 2H), 2.13-2.27 (m, 4H), 2.33-2.44 (m, 2H), 2.53-2.80 (m, 2H), 3.81 (s, 3H), 4.12 (dd, J=8.6, 15.8 Hz, 1H), 4.97 (septet, J=6.2 Hz, 1H), 5.29-5.48 (m, 2H), 6.04 (dd, J=8.6, 15.7 Hz, 1H), 6.47 (d, J=15.7 Hz, 1H), 6.79 (dd, J=2.2, 8.0 Hz, 1H), 6.89 (s, 1H), 6.94 (d, J=7.6 Hz, 1H), 7.19-7.27 (m, 1H); $^{13}$C NMR (100 MHz): δ –4.8 (CH$_3$), –4.7 (CH$_3$), 18.0 (C), 21.8 (CH$_3$), 24.8 (CH$_2$), 25.1 (CH$_2$), 25.7 (CH$_3$), 26.6 (CH$_2$), 34.0 (CH$_2$), 47.5 (CH$_2$), 54.0 (CH), 54.3 (CH), 55.1 (CH$_3$), 67.3 (CH), 73.0 (CH), 111.6 (CH), 112.8 (CH), 118.8 (CH), 126.4 (CH), 129.5 (CH), 130.1 (CH), 131.0 (CH), 132.7 (CH), 138.5 (C), 159.8 (C), 173.0 (C), 214.6 (C); HRMS (ESI-QTOF) calculated for [C$_{30}$H$_{46}$O$_5$Si+H]$^+$=515.3187, found 515.3172; FTIR (KBr, neat) 2945, 2862, 1737, 1666, 1590, 1463, 1375, 1257, 1156, 1108 cm$^{-1}$.

Example 11

Synthesis of (Z)-isopropyl 7-((1R,2R,3R)-3-((tert-butyldimethylsilyl)oxy)-2-((E)-4-fluorostyryl)-5-oxo-cyclopentyl)hept-5-enoate (10.13)

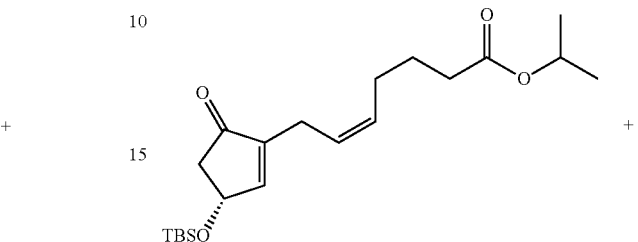

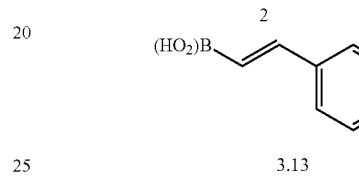

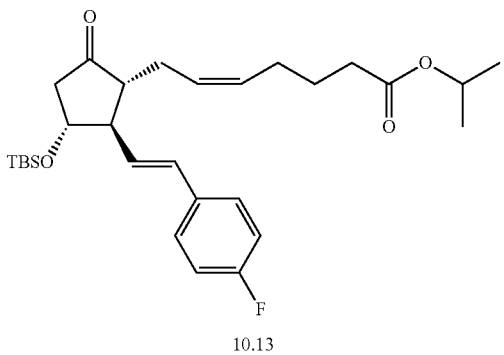

Following procedures described in Example 1, except using trans-2-(4-fluoromethyl-phenyl)-vinylboronic acid (3.13), the reaction crude mixture was purified by column chromatography (eluting with 1:80 (v/v) acetone-hexanes) affording the title compound 10.13 (69 mg, 92%).

$[\alpha]^{30}_D$ –44.7 (c 1.00, CHCl$_3$); $^1$H NMR (400 MHz): δ –0.01 (s, 3H), 0.01 (s, 3H), 0.85 (s, 9H), 1.19 (d, J=6.2 Hz, 6H), 1.64 (quintet, J=7.5 Hz, 2H), 2.04 (dd, J=7.1, 14.2 Hz, 2H), 2.12-2.28 (m, 4H), 2.32-2.45 (m, 2H), 2.54-2.74 (m, 2H), 4.11 (dd, J=8.6, 15.8 Hz, 1H), 4.96 (septet, J=6.2 Hz, 1H), 5.27-5.46 (m, 2H), 5.95 (dd, J=8.6, 15.7 Hz, 1H), 6.46 (d, J=15.7 Hz, 1H), 7.00 (dd, J=8.6, 8.7 Hz, 2H), 7.26-7.34 (m, 2H); $^{13}$C NMR (100 MHz): δ –4.8 (CH$_3$), –4.7 (CH$_3$), 18.0 (C), 21.8 (CH$_3$), 24.8 (CH$_2$), 25.1 (CH$_2$), 25.6 (CH$_3$), 26.6 (CH$_2$), 34.1 (CH$_2$), 47.5 (CH$_2$), 54.1 (CH), 54.3 (CH), 67.4 (CH), 72.9 (CH), 115.5 (d, J=21.0 Hz, CH), 126.5 (CH), 127.5 (d, J=8.0 Hz, CH), 129.5 (CH), 131.0 (CH), 131.7 (CH), 133.2 (d, J=3.0 Hz, C), 162.2 (d, J=245.0 Hz, C), 173.0 (C), 214.5 (C); HRMS (ESI-QTOF) calculated for [C$_{29}$H$_{43}$FO$_4$Si+H]$^+$=503.2987, found 503.2970; FTIR (KBr, neat) 2939, 1737, 1603, 1463, 1373, 1232, 1154, 1111, 845, 777 cm$^{-1}$.

Example 12

Synthesis of (Z)-isopropyl 7-((1R,2R,3R)-3-((tert-butyldimethylsilyl)oxy)-5-oxo-2-((E)-4-(trifluoromethyl)styryl)cyclopentyl)hept-5-enoate (10.14)

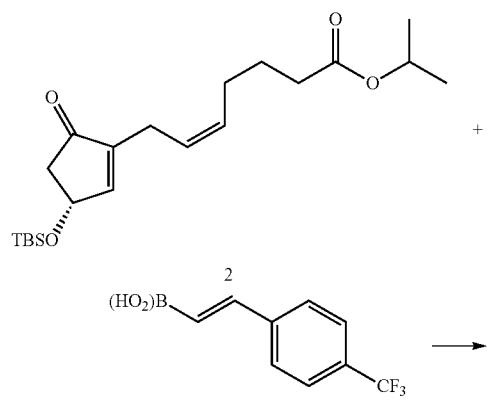

Following procedures described in Example 1, except using trans-2-(4-trifluoromethyl-phenyl)-vinylboronic acid (3.14), the reaction crude mixture was purified by column chromatography (eluting with 1:80 (v/v) acetone-hexanes) affording the title compound 10.14 (66 mg, 80%).

$[\alpha]^{29}_D$ –40.4 (c 1.00, CHCl$_3$); $^1$H NMR (400 MHz): δ –0.01 (s, 3H), 0.02 (s, 3H), 0.85 (s, 9H), 1.18 (d, J=6.2 Hz, 6H), 1.64 (quintet, J=7.4 Hz, 2H), 2.04 (dd, J=7.2, 14.5 Hz, 2H), 2.14-2.28 (m, 4H), 2.35-2.43 (m, 2H), 2.59-2.75 (m, 2H), 4.13 (dd, J=8.7, 15.9 Hz, 1H), 4.96 (septet, J=6.2 Hz, 1H), 5.25-5.52 (m, 2H), 6.16 (dd, J=8.6, 15.7 Hz, 1H), 6.54 (d, J=15.7 Hz, 1H), 7.44 (d, J=8.2 Hz, 2H), 7.57 (d, J=8.2 Hz, 2H); $^{13}$C NMR (100 MHz): δ –4.7 (CH$_3$), 18.0 (C), 21.8 (CH$_3$), 24.8 (CH$_2$), 25.1 (CH$_2$), 25.6 (CH$_3$), 26.6 (CH$_2$), 34.0 (CH$_2$), 47.5 (CH$_2$), 54.2 (CH), 54.3 (CH), 67.4 (CH), 72.8 (CH), 124.2 (q, J=270.2 Hz, C), 125.6 (q, J=4.0 Hz, CH), 126.2 (CH), 126.4 (CH), 129.2 (q, J=33.0 Hz, C), 131.1 (CH), 131.7 (CH), 132.6 (CH), 140.4 (C), 173.0 (C), 214.1 (C); HRMS (ESI-QTOF) calculated for [C$_{30}$H$_{43}$F$_3$O$_4$Si+H]$^+$=553.2955, found 553.2936; FTIR (KBr, neat) 2941, 2866, 1739, 1617, 1464, 1373, 1252, 1163, 1118, 840, 777 cm$^{-1}$.

Example 13

Synthesis of (Z)-isopropyl 7-((1R,2S,3R)-3-((tert-butyldimethylsilyl)oxy)-5-oxo-2-(prop-1-en-2-yl)cyclopentyl)hept-5-enoate (10.15)

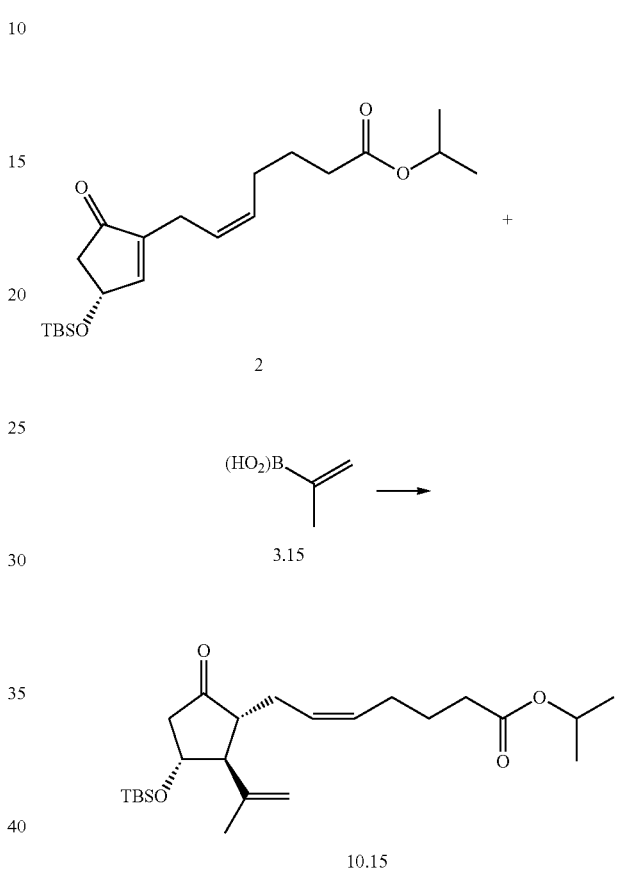

Following procedures described in Example 1 except using prop-1-en-2-ylboronic acid (3.15), the reaction crude mixture was purified by column chromatography (eluting with 1:80 (v/v) acetone-hexanes) affording the title compound 10.15 (48 mg, 76%).

$[\alpha]^{25}_D$ –85.4 (c 1.00, CHCl$_3$); $^1$H NMR (400 MHz): δ 0.016 (s, 3H), 0.024 (s, 3H), 0.86 (s, 9H), 1.22 (d, J=6.2 Hz, 6H), 1.58-1.69 (m, 3H), 1.73 (s, 3H), 2.04 (q, J=7.0 Hz, 2H), 2.10-2.27 (m, 3H), 2.27-2.34 (m, 2H), 2.50 (dd, J=8.3, 12.0 Hz, 1H), 2.66 (dd, J=7.1, 18.4 Hz, 1H), 4.13 (dd, J=8.2, 15.8 Hz, 1H), 4.85 (s, 1H), 4.93 (s, 1H), 4.99 (septet, J=6.2 Hz, 1H), 5.28-5.44 (m, 2H); $^{13}$C NMR (100 MHz): δ –4.9 (CH$_3$), –4.8 (CH$_3$), 18.0 (C), 19.6 (CH$_3$), 21.8 (CH$_3$), 24.8 (CH$_2$), 25.3 (CH$_2$), 25.7 (CH$_3$), 26.6 (CH$_2$), 34.1 (CH$_2$), 47.7 (CH$_2$), 52.2 (CH), 57.7 (CH), 67.4 (CH), 71.3 (CH), 114.2 (CH$_2$), 126.5 (CH), 130.8 (CH), 142.4 (C), 173.1 (C), 215.2 (C); HRMS (ESI-QTOF) calculated for [C$_{24}$H$_{42}$O$_4$Si+H]$^+$=423.2925, found 423.2927; FTIR (KBr, neat) 3421, 2950, 2862, 1738, 1636, 1376, 1253, 1107, 888, 837, 786 cm$^{-1}$.

Example 14

Synthesis of (Z)-isopropyl 7-((1R,2S,3R)-2-((E)-but-2-en-2-yl)-3-((tert-butyldimethylsilyl)oxy)-5-oxocyclopentyl)hept-5-enoate (10.16)

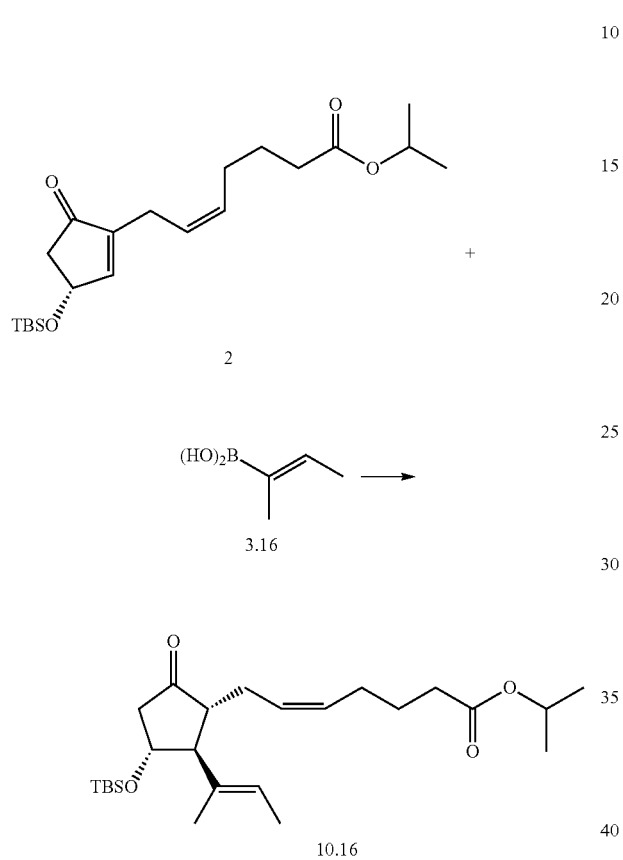

Following procedures described in Example 1 except using (Z)-but-2-en-2-ylboronic acid (3.16), the reaction crude mixture was purified by column chromatography (eluting with 1:80 (v/v) acetone-hexanes) affording the title compound 10.16 (24 mg, 37%).

$[\alpha]^{25}_D$ –43.6 (c 1.00, CHCl$_3$); $^1$H NMR (400 MHz): δ –0.01 (s, 3H), 0.01 (s, 3H), 0.85 (s, 9H), 1.22 (d, J=6.0 Hz, 6H), 1.54-1.71 (m, 8H), 1.99-2.08 (m, 2H), 2.10-2.31 (m, 6H), 2.59-2.72 (m, 1H), 3.04 (dd, J=8.8, 12.4 Hz, 1H), 4.15 (q, J=8.8 Hz, 1H), 4.99 (septet, J=6.0 Hz, 1H), 5.29-5.42 (m, 2H), 5.48-5.55 (m, 1H); $^{13}$C NMR (100 MHz): δ –5.0 (CH$_3$), –4.9 (CH$_3$), 13.4 (CH$_3$), 17.9 (C), 18.7 (CH$_3$), 21.8 (CH$_3$), 24.8 (CH$_2$), 24.9 (CH$_2$), 25.7 (CH$_3$), 26.4 (CH$_2$), 34.1 (CH$_2$), 47.7 (CH$_2$), 50.7 (CH), 51.7 (CH), 67.4 (CH), 70.0 (CH), 125.0 (CH), 126.6 (CH), 130.6 (CH), 131.4 (C), 173.1 (C), 215.4 (C); HRMS (ESI-QTOF) calculated for [C$_{25}$H$_{44}$O$_4$Si+H]$^+$=437.3081, found 437.3087; FTIR (KBr, neat) 3452, 2938, 1736, 1667, 1461, 1373, 1250, 1108, 972, 838 cm$^{-1}$.

Example 15

Synthesis of isopropyl (Z)-7-[(2R,3R)-3-(tert-butyl-dimethyl-silanyloxy)-5-oxo-2-styryl-cyclopentyl]-hept-5-enoate (10.1)

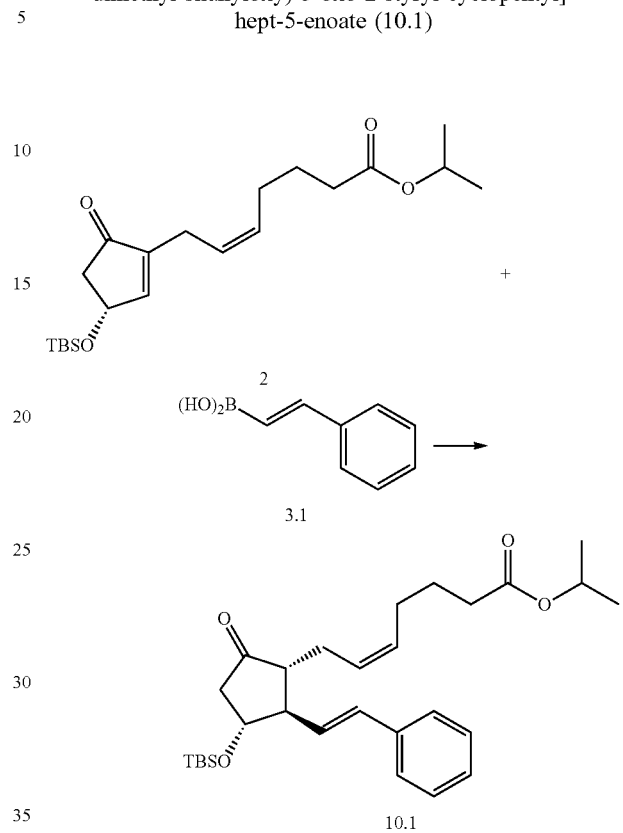

A solution of 2 (57 mg, 0.15 mmol), trans-2-phenylvinylboronic acid (3.1) (33mg, 0.22 mmol), [RhCl(1,5-cyclooctadiene)]$_2$ (1.1 mg, 2.2 μmol) and aq. t-BuOK (20 μL, 1.5 M aq. t-BuOK, 30 μmol) in dioxane (1.0 mL) was stirred at 60° C. for 4 days using conventional heating (heating mantle) and then the reaction mixture was directly concentrated in vacuo. The residue was purified by column chromatography (eluting with 1:80 (v/v) acetone-hexanes) affording 10.1 (39 mg, 54%).

Example 16

Synthesis of isopropyl (Z)-7-[(2R,3R)-3-(tert-butyl-dimethyl-silanyloxy)-5-oxo-2-styryl-cyclopentyl]-hept-5-enoate (10.1)

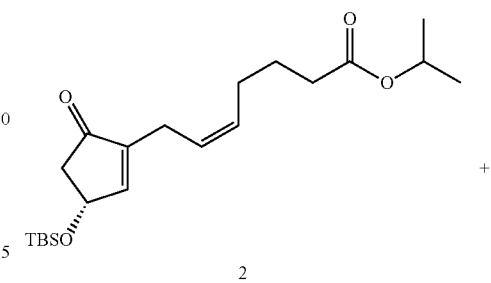

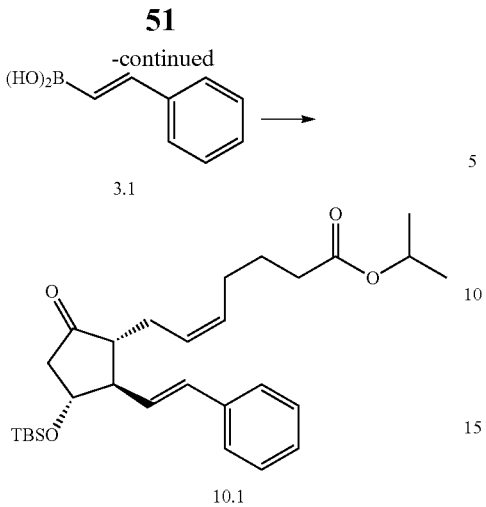

A solution of 2 (57 mg, 0.15 mmol), trans-2-phenylvinylboronic acid (3.1) (33 mg, 0.22 mmol), [RhCl(1,5-cyclooctadiene)]₂ (1.1 mg, 2.2 μmol) and aq. t-BuOK (20 μL, 1.5 M aq. t-BuOK, 30 μmol) in isopropanol (1.0 mL) was stirred at 60° C. for 3 days using conventional heating (heating mantle) and then the reaction mixture was directly concentrated in vacuo. The residue was purified by column chromatography (eluting with 1:80 (v/v) acetone-hexanes) affording 10.1 (43 mg, 59%).

Example 17

Synthesis of isopropyl (Z)-7-[(2R,3R)-3-(tert-butyl-dimethyl-silanyloxy)-5-oxo-2-styryl-cyclopentyl]-hept-5-enoate (10.1)

A solution of 2 (57 mg, 0.15 mmol), trans-2-phenylvinylboronic acid (3.1) (33 mg, 0.22 mmol), [RhCl(1,5-cyclooctadiene)]₂ (1.1 mg, 2.2 μmol) and aq. KOH (9.5 μL, 3.0 M aq. KOH, 29 μmmol) in isopropanol (1.0 mL) was stirred at 25° C. for 3 days and then the reaction mixture was directly concentrated in vacuo. The crude product mixture was then analyzed by ¹H NMR spectroscopy which showed 70% yield of 10.1 and 22% recovery of 2.

Example 18

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17 the title compound was synthesized using aq. KHF₂ (0.3 mL, 3.0 M aq. KHF₂, 0.9 mmol) as the basic additive. The crude product mixture was then analyzed by ¹H NMR spectroscopy which showed 74% yield of 10.1 and 18% recovery of 2.

Example 19

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using aq. NaOH (9.5 μL, 3.0 M aq. NaOH, 29 μmmol) as the basic additive. The crude product mixture was then analyzed by ¹H NMR spectroscopy which showed 35% yield of 10.1 and 70% recovery of 2.

Example 20

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using aq. LiOH (9.5 μL, 3.0 M aq. LiOH, 29 μmmol) as the basic additive. The crude product mixture was then analyzed by ¹H NMR spectroscopy which showed 25% yield of 10.1 and 65% recovery of 2.

Example 21

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using aq. CsOH (9.5 μL, 3.0 M aq. CsOH, 29 μmmol) as the basic additive. The crude product mixture was then analyzed by ¹H NMR spectroscopy which showed 22% yield of 10.1 and 77% recovery of 2.

Example 22

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using aq. K₂CO₃ (0.3 mL, 3.0 M aq. K₂CO₃, 0.9 mmol) as the basic additive. The crude product mixture was then analyzed by ¹H NMR spectroscopy which showed 13% yield of 10.1 and 60% recovery of 2.

Example 23

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using aq. K₃PO₄ (0.6 mL, 1.5 M aq. K₃PO₄, 0.9 mmol) as the basic additive. The crude product mixture was then analyzed by ¹H NMR spectroscopy which showed 54% yield of 10.1 and 26% recovery of 2.

Example 24

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 18, the title compound was synthesized using dichlorobis(norbornadiene)dirhodium (1.0 mg, 2.2 μmol) as the metal additive. The crude product mixture was then analyzed by ¹H NMR spectroscopy which showed 35% yield of 10.1 and 57% recovery of 2.

Example 25

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 18, the title compound was synthesized using [RhCl($C_2H_4$)$_2$]$_2$ (0.9 mg, 2.3 µmmol) as the metal additive. The crude product mixture was then analyzed by ¹H NMR spectroscopy which showed 29% yield of 10.1 and 69% recovery of 2.

Example 26

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using t-BuOH (0.8 mL) as the solvent. The crude product mixture was then analyzed by ¹H NMR spectroscopy which showed 58% yield of 10.1 and 44% recovery of 2.

Example 27

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using EtOH (0.8 mL) as the solvent. The crude product mixture was then analyzed by ¹H NMR spectroscopy which showed 75% yield of 10.1 and 15% recovery of 2.

Example 28

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using MeOH (0.8 mL) as the solvent. The crude product mixture was then analyzed by ¹H NMR spectroscopy which showed 80% yield of 10.1 and 17% recovery of 2.

Example 29

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using MeOH—H$_2$O (0.8 mL, 1:1 v/v) as the solvent. The crude product mixture was then analyzed by ¹H NMR spectroscopy which showed 61% yield of 10.1 and 39% recovery of 2.

Example 30

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 18, the title compound was synthesized using dioxane (0.8 mL) as the solvent. The crude product mixture was then analyzed by ¹H NMR spectroscopy which showed 48% yield of 10.1 and 52% recovery of 2.

Example 31

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 28, the title compound was synthesized using K$_3$PO$_4$ (0.6 mL, 1.5 M aq. K$_3$PO$_4$, 0.9 mmol) as the basic additive. The crude product mixture was then analyzed by ¹H NMR spectroscopy which showed 60% yield of 10.1 and 42% recovery of 2.

Example 32

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 28, the title compound was synthesized using t-BuNH$_2$ (0.95 mL, 9.0 mmol) as the basic additive. The crude product mixture was then analyzed by ¹H NMR spectroscopy which showed 50% yield of 10.1 and 50% recovery of 2.

Example 33

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 28, the title compound was synthesized using piperidine (0.89 mL, 9.0 mmol) as the basic additive. The crude product mixture was then analyzed by ¹H NMR spectroscopy which showed 28% yield of 10.1 and 38% recovery of 2.

Example 34

Synthesis of isopropyl (Z)-7-[(2R,3R)-3-(tert-butyl-dimethyl-silanyloxy)-5-oxo-2-styryl-cyclopentyl]-hept-5-enoate (10.1)

Following the procedure described in Example 17, the title compound was synthesized using 1,3-diaminopropane (0.8 mL, 9.6 mml) as the basic additive. The crude product mixture was then analyzed by ¹H NMR spectroscopy which showed 42% yield of 10.1 and 38% recovery of 2.

Example 35

Synthesis of isopropyl (Z)-7-[(2R,3R)-3-(tert-butyl-dimethyl-silanyloxy)-5-oxo-2-styryl-cyclopentyl]-hept-5-enoate (10.1)

A solution of 2 (57 mg, 0.15 mmol), trans-2-phenylvinyl-boronic acid (3.1) (33 mg, 0.22 mmol) and [RhOH(1,5-cyclooctadiene)]₂ (1.0 mg, 2.2 μmol) in MeOH (1.0 mL) was stirred for 6 hours under microwave irradiation while the temperature was set to 30° C., and then the reaction mixture was directly concentrated in vacuo. The crude product mixture was then analyzed by ¹H NMR spectroscopy which showed 29% yield of 10.1 and 74% recovery of 2.

Example 36

Synthesis of isopropyl (Z)-7-[(2R,3R)-3-(tert-butyl-dimethyl-silanyloxy)-5-oxo-2-styryl-cyclopentyl]-hept-5-enoate (10.1)

A solution of 2 (57 mg, 0.15 mmol), trans-2-phenylvinyl-boronic acid (3.1) (33 mg, 0.22 mmol) and [RhOH(1,5-cyclooctadiene)]₂ (1.0 mg, 2.2 μmol) in MeOH (1 mL) was stirred at 50° C. for 3 days using conventional heating (heating mantle) and then the reaction mixture was directly concentrated in vacuo. The crude product mixture was then analyzed by ¹H NMR spectroscopy which showed 47% yield of 10.1 and 53% recovery of 2.

Example 37

Synthesis of tert-butyl-(1-ethynyl-hexyloxy)-dimethyl-silane (1.8a)

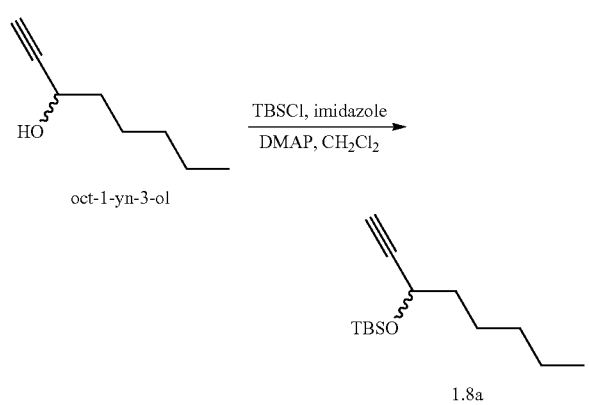

To a solution of oct-1-yn-3-ol (11.574 mL, 76.1 mmol), imidazole (10.4 g, 153 mmol) and DMAP (0.929 g, 7.60 mmol) in CH₂Cl₂ (100 mL) at 0-5° C. was added dropwise a solution of TBSCl (17.2 g, 114 mmol) in CH₂Cl₂ (50 mL). The reaction mixture (white suspension) was allowed to warm up to room temperature. The mixture was stirred at room temperature for 20 h and diluted with CH₂Cl₂ (150 mL) and sat. aq. NH₄Cl (300 mL). The organic layer was separated and the aqueous layer was extracted with CH₂Cl₂ (200 mL×2). The combined organic layer was washed with brine, dried over MgSO₄, and concentrated. Column chromatography (eluting with 1:20 (v/v) EtOAc-n-heptane) afforded the title compound 1.8a as a colorless liquid (18.11 g, 99%).

¹H NMR (400 MHz, CDCl₃): δ 4.35 (td, J=6.4, 2.0 Hz, 1H), 2.38 (d1H), 1.72-1.67 (m, 2H), 1.62-1.45 (m, 2H), 1.44-1.30 (m, 4H), 0.91-0.86 (m, 12H), 0.04 (s, 3H), 0.02 (s, 3H); ¹³C NMR (100 MHz, CDCl₃): δ 85.8, 71.8, 62.8, 38.5, 31.4, 25.8 (CH₂×3), 24.8, 22.6, 18.2, 14.0, −4.6, −5.1; FTIR (KBr, neat) 3312, 2956, 2930, 2858, 1716, 1642, 1471, 1463, 1362, 1341, 1253, 1144, 1119, 1005, 969 cm⁻¹.

Example 38

Synthesis of 2-[3-(tert-butyl-dimethyl-silanyloxy)-oct-1-enyl]-4,4,5,5-tetramethyl-[1,3,2]dioxaborolane (2.8a)

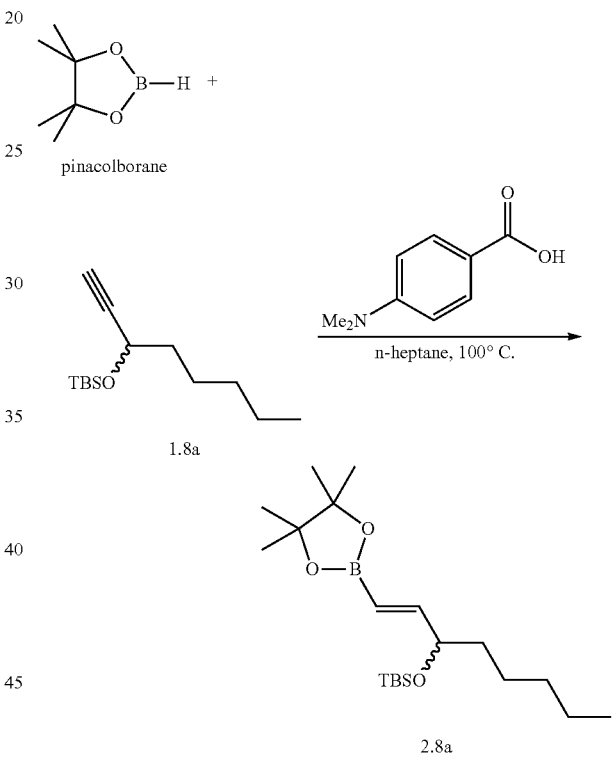

To n-heptane (10.0 mL) was added tert-butyl-(1-ethynyl-hexoxy)-dimethyl-silane (2.48 g, 10.3 mmol), 5 mol % of 4-(dimethylamino)benzoic acid (83 mg, 0.50 mmol) and pinacolborane (4.5 mL, 30 mmol; neat oil) under N₂ atmosphere at ambient temperature. The solution was heated by 100° C. bath for 5.5 hours and was cooled to room temperature. The mixture was diluted with EtOAc (30 mL) and sat. aq. NH₄Cl solution (40 mL) and the layers were separated. The aqueous layer was back-extracted with EtOAc (30 mL) and the combined organic layers were washed with brine (50 mL), dried over anhydrous MgSO₄ (2.5 g), filtered and concentrated under reduced pressure to afford the crude mixture which was purified by column chromatography (50 g SiO₂; eluting with n-heptane (200 mL) then 1:50 (v/v) MTBE-n-heptane (750 mL)) to give the title compound (2.85 g, 7.74 mmol, 75% yield).

¹H NMR (400 MHz, CDCl₃): δ 6.37 (1H, dd, J=18.0, 5.6), 5.43 (1H, dd, J=18.0, 1.2), 4.11 (1H, m), 1.48 (2H, m), 1.29

(6H, m), 1.28 (12H, s), 0.90 (9H, s), 0.88 (3H,m), 0.04 (3H, s), 0.03 (3H, s); $^{13}$C NMR (100 MHz, CDCl$_3$): δ 156.2, 116.2, 83.0 (C×2), 74.1, 37.5, 31.9, 25.9 (CH$_2$×3), 24.8 (CH×2), 24.7 (CH×3), 22.6, 18.2, 14.0, −4.4, −4.9; FTIR (KBr, neat) 2956, 2929, 2857, 1715, 1642, 1463, 1471, 1362, 1339, 1255, 1165, 1087 cm$^{-1}$; HRMS (ESI-QTOF) calculated for [C$_{20}$H$_{41}$BO$_3$Si+OH]$^-$=385.2951, found 385.2961.

Example 39

Synthesis of (E)-(3-((tert-butyldimethylsilyl)oxy)oct-1-en-1-yl)boronic acid (3.8a)

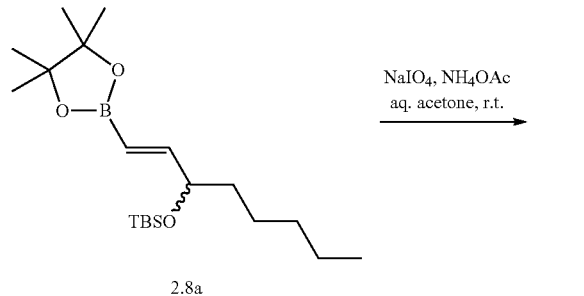

To a solution of 2-[3-(tert-Butyl-dimethyl-silanyloxy)-oct-1-enyl]-4,4,5,5-tetramethyl-[1,3,2]dioxaborolane (2.8a, 0.99 g, 2.69 mmol) in acetone and water (150 mL, 2:1 v/v) was added NaIO$_4$ (1.80 g, 8.42 mmol; 3.1 equiv.) and NH$_4$OAc (0.63 g, 8.17 mmol; 3.0 equiv.). The resulting cloudy solution was stirred at ambient temperature for 20 hours and was concentrated under reduced pressure to remove acetone. The residue was diluted with EtOAc (50 mL) and the layers were separated. The aqueous layer was back-extracted with EtOAc (50 mL) and the combined organic layers were washed with brine (100 mL), dried over MgSO$_4$ (2.0 g), filtered, and concentrated under reduced pressure to provide the title boronic acid 3.8a (820 mg, quant.).

$^1$H NMR (400 MHz, DMSO-d$_6$): δ 7.57 (2H, s), 6.58 (1H, dd, J=17.8, 5.0), 5.58 (1H, dd, J=18.0, 1.2), 4.16 (1H, m), 1.39 (2H, m), 1.37 (6H, m), 0.84 (9H, s), 0.83 (3H,m), 0.01 (3H, s), −0.01 (3H, s); $^{13}$C NMR (100 MHz, DMSO-d$_6$): δ 152.1, 122.4, 74.0, 37.2, 31.2, 25.7 (CH×3), 24.2, 22.0, 17.9, 13.8, −4.4, −4.9; FTIR (KBr, neat) 2956, 2929, 2857, 1636, 1472, 1463, 1348, 1286, 1255, 1118, 1088, 1004, 966 cm$^{-1}$; HRMS (ESI-QTOF) calculated for [C$_{14}$H$_{31}$BO$_3$Si−H]$^-$=285.2063, found 285.2082.

Example 40

Synthesis of 1-(4,4,5,5-tetramethyl-[1,3,2]dioxaborolan-2-yl)-oct-1-en-3-ol (2.8)

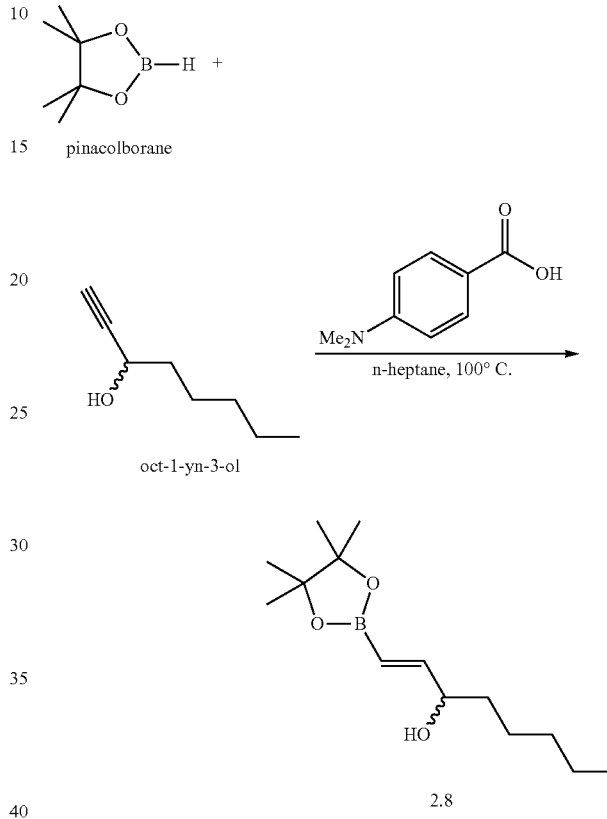

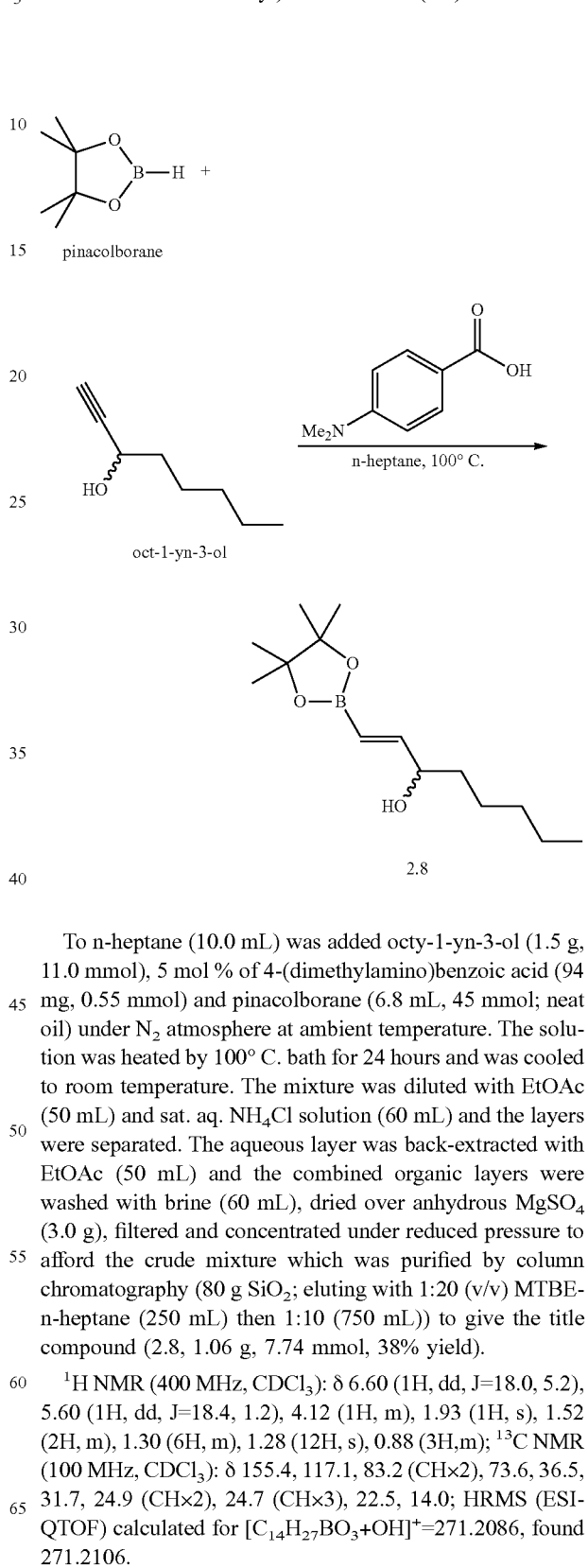

To n-heptane (10.0 mL) was added octy-1-yn-3-ol (1.5 g, 11.0 mmol), 5 mol % of 4-(dimethylamino)benzoic acid (94 mg, 0.55 mmol) and pinacolborane (6.8 mL, 45 mmol; neat oil) under N$_2$ atmosphere at ambient temperature. The solution was heated by 100° C. bath for 24 hours and was cooled to room temperature. The mixture was diluted with EtOAc (50 mL) and sat. aq. NH$_4$Cl solution (60 mL) and the layers were separated. The aqueous layer was back-extracted with EtOAc (50 mL) and the combined organic layers were washed with brine (60 mL), dried over anhydrous MgSO$_4$ (3.0 g), filtered and concentrated under reduced pressure to afford the crude mixture which was purified by column chromatography (80 g SiO$_2$; eluting with 1:20 (v/v) MTBE-n-heptane (250 mL) then 1:10 (750 mL)) to give the title compound (2.8, 1.06 g, 7.74 mmol, 38% yield).

$^1$H NMR (400 MHz, CDCl$_3$): δ 6.60 (1H, dd, J=18.0, 5.2), 5.60 (1H, dd, J=18.4, 1.2), 4.12 (1H, m), 1.93 (1H, s), 1.52 (2H, m), 1.30 (6H, m), 1.28 (12H, s), 0.88 (3H,m); $^{13}$C NMR (100 MHz, CDCl$_3$): δ 155.4, 117.1, 83.2 (CH×2), 73.6, 36.5, 31.7, 24.9 (CH×2), 24.7 (CH×3), 22.5, 14.0; HRMS (ESI-QTOF) calculated for [C$_{14}$H$_{27}$BO$_3$+OH]$^+$=271.2086, found 271.2106.

Example 41

Synthesis of (E)-(3-hydroxyoct-1-en-1-yl)boronic acid (3.8)

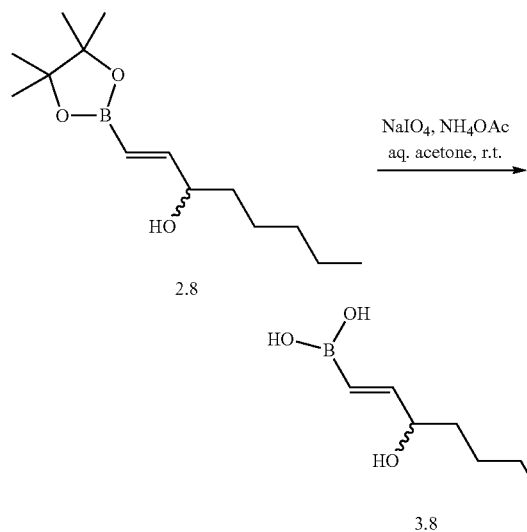

To a solution of 2.8 (1.17 g, 4.6 mmol) in acetone and water (180 mL, 2:1 v/v) was added NaIO$_4$ (3.05 g, 14.3 mmol) and NH$_4$OAc (1.06 g, 13.8 mmol). The resulting cloudy solution was stirred at 40° C. for 20 hours and was concentrated under reduced pressure to remove acetone. The residue was diluted with EtOAc (60 mL) and the layers were separated. The aqueous layer was back-extracted with EtOAc (60 mL) and the combined organic layers were washed with brine (120 mL), dried over MgSO$_4$ (2.5 g), filtered, and concentrated under reduced pressure to provide the title compound (3.8, 443 mg, 56%).

$^1$H NMR (400 MHz, DMSO-d$_6$): δ 7.55 (s, 2H), 6.39 (dd, J=18.0, 5.2 Hz, 1H), 5.42 (dd, J=18.0, 1.2 Hz, 1H), 4.66 (d, J=4.4 Hz, 1H), 3.90 (m, 1H), 1.34 (m, 2H), 1.27 (m, 6H), 0.85 (m, 3H); $^{13}$C NMR (100 MHz, DMSO-d$_6$): δ 153.8, 122.4, 72.5, 37.2, 31.8, 25.1, 22.6, 14.4; HRMS (ESI-QTOF) calculated for [C$_8$H$_{17}$BO$_3$–H]$^-$=171.1198, found 171.1210.

Example 42

Synthesis of oct-1-yn-3-yl acetate (1.8b)

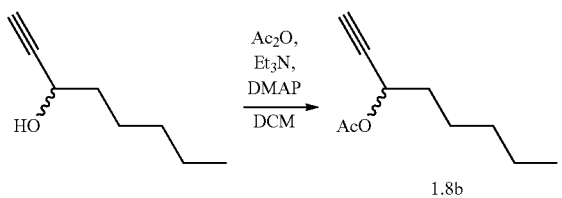

A flask was charged with 4-dimethylaminopyridine (610 mg, 4.9930 mmol), oct-1-yn-3-ol (7.3 mL, 50 mmol), and dichloromethane (100 mL). The solution was cooled to 0° C. and triethylamine (20.9 mL, 150 mmol) was added, followed by dropwise addition of acetic anhydride (7.09 mL, 75 mmol) in 3 mL of dichloromethane. The solution was gradually warmed to room temperature. After the reaction was completed, the reaction mixture was concentrated in vacuo. The crude reaction mixture was purified on silica gel (eluting with 1:25 (v/v) MTBE-hexanes) to afford the title compound (1.8b, 8.21 g, 97.6% yield) as a pale yellow oil.

$^1$H NMR (400 MHz, CDCl$_3$): δ 5.30 (t, J=5.2 Hz, 1H), 2.43 (d1H), 2.04 (s, 3H), 1.75-1.70 (m, 2H), 1.41-1.39 (m, 2H), 1.28-1.27 (m, 4H), 0.86-0.84 (m, 3H); $^{13}$C NMR (100 MHz, CDCl$_3$): δ 169.7, 81.2, 73.4, 63.7, 34.5, 31.2, 24.5, 22.4, 20.9, 13.9.

Example 43

Synthesis of (E)-1-(4,4,5,5-tetramethyl-1,3,2-dioxaborolan-2-yl)oct-1-en-3-yl acetate (2.8b)

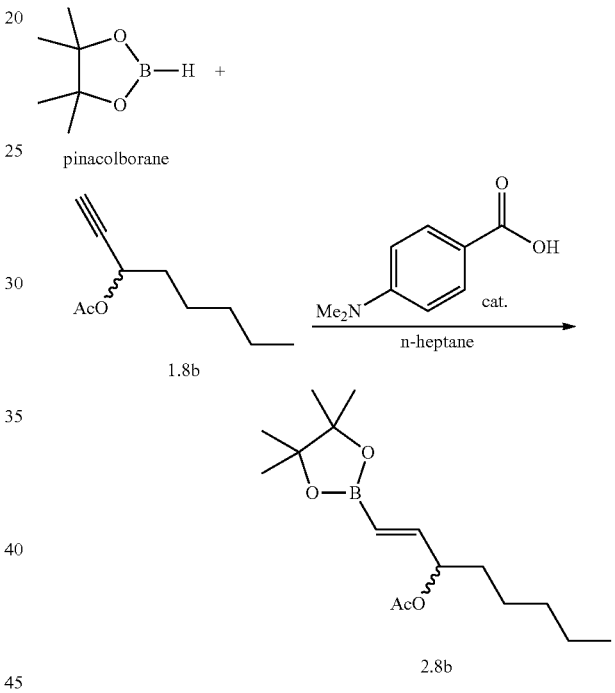

To dry n-heptane (15 mL) was added oct-1-yn-3-yl acetate (2.5 g, 15 mmol), 4-dimethylaminobenzoic acid (120 mg, 0.74 mmol), and pinacolborane (6.47 mL, 43.3 mmol) under N$_2$. The solution was heated to 90-100° C. After the reaction was complete and cooled to room temperature, the reaction mixture was concentrated under vacuum and partitioned between EtOAc (50 mL) and 10% aq. NH$_4$Cl (50 mL). The aqueous phase was extracted with EtOAc (50 mL×2) and the combined organic phases were washed with brine (100 mL), and dried over MgSO$_4$. The reaction mixture was concentrated in vacuo, and the crude reaction mixture was purified on silica gel (eluting with 1:25 (v/v) MTBE-n-heptane with 1% Et$_3$N) to afford the title compound (2.8b, 1.23 g, 27.9% yield) as a pale yellow oil.

$^1$H NMR (400 MHz, CDCl$_3$): δ 6.38 (dd, J=18.4, 5.2 Hz, 1H), 5.57 (dd, J=17.2, 1.2 Hz, 1H), 5.32-5.27 (m, 1H), 2.07 (s, 3H), 1.64-1.59 (m, 2H), 1.34-1.24 (m, 17H), 0.90-0.86 (m, 4H); $^{13}$C NMR (100 MHz, CDCl$_3$): δ 170.3, 150.3, 83.3 (C×2), 75.0, 33.8, 31.6, 24.8, 24.7 (CH$_3$×4), 22.5, 21.1, 14.0 (the ipso carbon (attached to B) signal was not observed due to low intensity).

Example 44

Synthesis of (I)-(3-acetoxyoct-1-en-1-yl)boronic acid (3.8b)

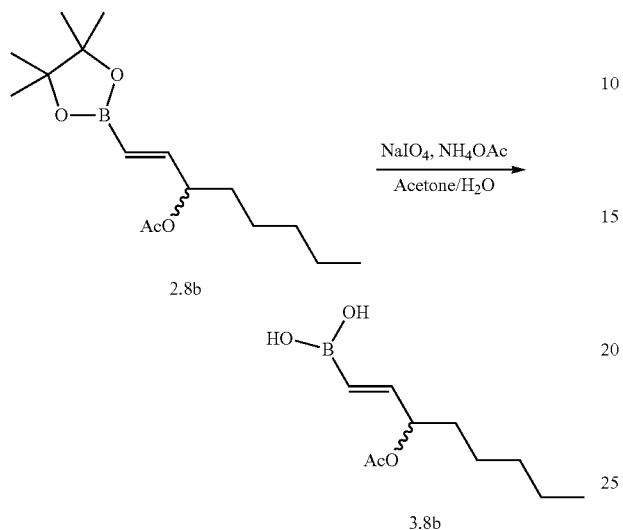

To a solution of 2.8b (950 mg, 3.2 mmol) in acetone/H$_2$O (3/1, v/v) (142 mL) was added sodium periodate (2.13 g, 9.96 mmol) and ammonium acetate (742 mg, 9.63 mmol). The resulting cloudy solution was stirred at 40° C. After the reaction was completed, the reaction mixture was placed under reduced pressure to remove acetone. The residual was diluted with EtOAc (100 mL) and the phases were separated. The aqueous layer was extracted with EtOAc (100 mL) and the combined organic layers were washed with brine (50 mL), dried over MgSO$_4$. The reaction mixture was concentrated in vacuo, and the crude reaction mixture was purified on silica gel (eluting with 1:4 (v/v) acetone-n-heptane) to afford the title compound (3.8b, 507 mg, 74% yield) as a pale yellow oil.

$^1$H NMR (400 MHz, DMSO-d$_6$): δ 6.34 (dd, J=18, 5.2 Hz, 1H), 5.44 (dd, J=18.4, 1.6 Hz, 1H), 5.17-5.13 (m, 1H), 2.04 (s, 3H), 1.56-1.52 (m, 2H), 1.3-1.26 (m, 6H), 0.88-0.84 (m, 3H); $^{13}$C NMR (100 MHz, DMSO-d$_6$): δ 170.1, 147.2, 75.2, 33.9, 31.4, 24.7, 22.4, 21.3, 14.3 (the ipso carbon (attached to B) signal was not observed due to low intensity); HRMS (ESI-QTOF) calculated for [C$_{10}$H$_{19}$BO$_4$-H]$^-$=213.1304, found 213.1316.

Example 45

Synthesis of {[(1-pentylprop-2-ynyl)oxy]methyl}benzene (1.8c)

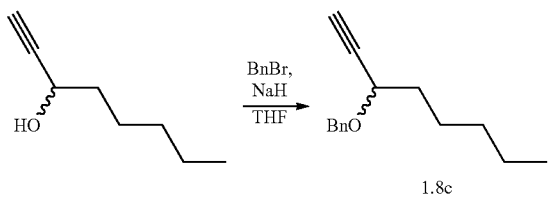

A flask was charged with oct-1-yn-3-ol (6 g, 47.544 mmol) and THF (60 mL). The solution was cooled to 0-5° C., and then was added 60% NaH (2.9 g, 73 mmol). The mixture was added BnBr (6 mL, 50.45 mmol) dropwise, and then stirred at room temperature. After the reaction was complete, the mixture was quenched by adding 30 mL of H$_2$O at 0-15° C. The reaction mixture was extracted with EtOAc (50 mL×2) and the combined organic phases were washed with brine (30 mL), and dried over MgSO$_4$. The reaction mixture was concentrated in vacuo, and the crude reaction mixture was purified on silica gel (eluting with 0-20% (v/v) EtOAc-n-heptane) to afford the title compound as a pale yellow oil (1.8c, 10.27 g, 47.5 mmol, 99.9% yield).

$^1$H NMR (400 MHz, CDCl$_3$): δ 7.40-7.28 (m, 5H), 4.84 (d, J=12 Hz, 1H), 4.54 (d, J=12 Hz, 1H), 4.12-4.08 (m, 1H), 2.49 (d, J=2 Hz, 1H), 1.83-1.74 (m, 2H), 1.53-1.50 (m, 2H), 1.37-1.28 (m, 4H), 0.93-0.92 (m, 3H); $^{13}$C NMR (100 MHz, CDCl$_3$): δ 137.9, 128.4 (CH×2), 128.0 (CH×2), 127.7, 83.1, 73.7, 70.5, 68.5, 35.6, 31.5, 24.9, 22.5, 14.0.

Example 46

Synthesis of (E)-2-[3-(benzyloxy)oct-1-en-1-yl]-4,4,5,5-tetramethyl-1,3,2-dioxaborolane (2.8c)

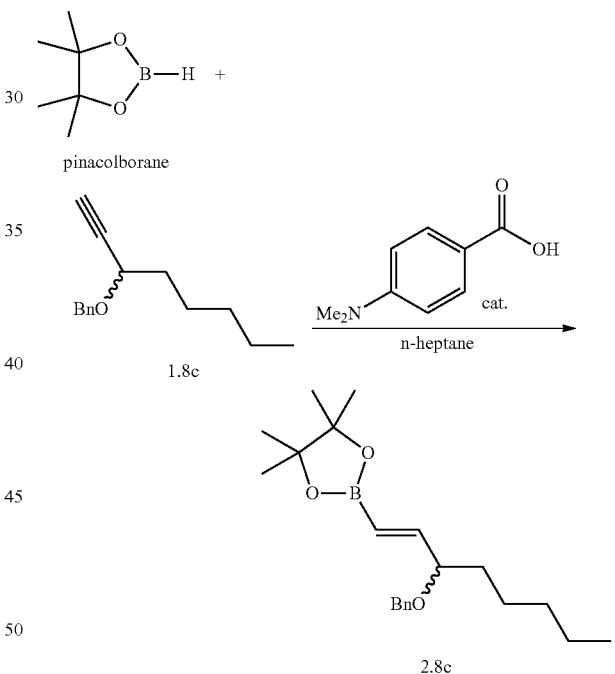

To dry n-heptane (15 mL) was added 1.8c (2.18 g, 10.1 mmol), 4-dimethylaminobenzoic acid (0.0906 g, 0.548 mmol), and pinacolborane (5 mL, 33.4 mmol) under N$_2$. The solution was heated to 90-100° C. After the reaction was complete and cooled to room temperature, the reaction mixture was concentrated under vacuum and partitioned between EtOAc (50 mL) and 10% aq. NH$_4$Cl (50 mL). The aqueous phase was extracted with EtOAc (50 mL×2) and the combined organic phases were washed with brine (100 mL) and dried over MgSO$_4$. The reaction mixture was concentrated in vacuo, and the crude reaction mixture was purified on silica gel (eluting with 1:30 (v/v) EtOAc-n-heptane) to afford the title compound as a pale yellow oil (2.8c, 2.75 g, 79.2% yield).

$^1$H NMR (400 MHz, CDCl$_3$): δ 7.36-7.28 (m, 5H), 6.53 (dd, J=18, 6.8 Hz, 1H), 5.65 (dd, .1=18.4, 0.8 Hz, 1H), 4.62 (d, J=12 Hz, 1H), 4.36 (d, J=12 Hz, 1H), 3.82-3.80 (m, 1H), 1.65-1.26 (m, 20H), 0.90-0.97 (m, 3H); $^{13}$C NMR (100 MHz, CDCl$_3$): δ 153.6, 138.8, 128.3 (CH×2), 127.7 (CH×2), 127.4, 83.3 (C×2), 81.3, 70.5, 35.1, 31.8, 25.0, 24.8 (CH$_3$× 4), 22.6, 14.1 (the ipso carbon (attached to B) signal was not observed due to low intensity).

Example 47

Synthesis of (E)-[3-(benzyloxy)oct-1-en-1-yl]boronic acid (3.8c)

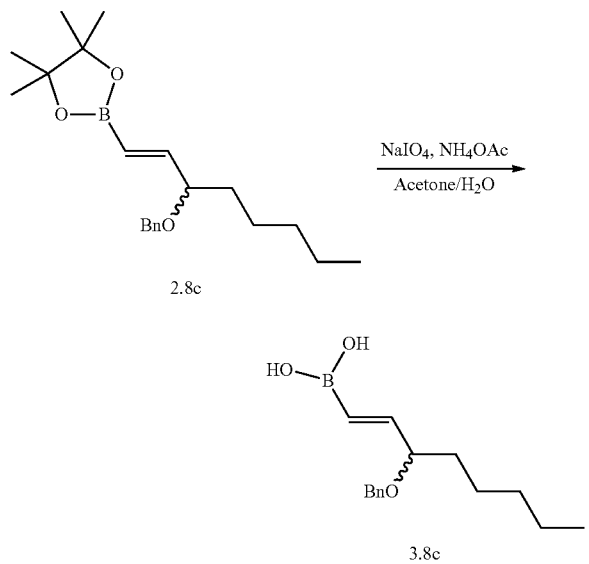 [SMILES: CCCCCC(/C=C/B1OC(C)(C)C(C)(C)O1)OCc1ccccc1 ; CCCCCC(/C=C/B(O)O)OCc1ccccc1]

To a solution of 2.8c (1.2 g, 3.5 mmol) in acetone/H$_2$O (3/1, v/v) (150 mL) was added sodium periodate (1.8 g, 8.4 mmol) and ammonium acetate (0.67 g, 8.7 mmol). The resulting cloudy solution was stirred at 40° C. After the reaction was complete, the reaction mixture was placed under reduced pressure to remove acetone. The residual was diluted with EtOAc (100 mL) and the phases were separated. The aqueous layer was extracted with EtOAc (100 mL) and the combined organic layers were washed with brine (50 mL) and dried over MgSO$_4$. The reaction mixture was concentrated in vacuo, and the crude reaction mixture was purified on silica gel (eluting with 35% acetone-n-heptane) to afford the title compound as a pale yellow oil (3.8c, 0.7 g, 80% yield).

$^1$H NMR (400 MHz, DMSO-d$_6$): δ 7.68 (s, 2H), 7.37-7.26 (m, 5H), 6.33 (dd, J=18, 6.8 Hz, 1H), 5.52 (d, J=18 Hz, 1H), 4.49 (d, J=12 Hz, 1H), 4.29 (d, J=12 Hz, 1H), 3.79-3.75 (m, 1H), 1.55-1.20 (m, 8H), 0.86-0.83 (m, 3H); $^{13}$C NMR (100 MHz, DMSO-d$_6$): δ 150.0, 139.3, 128.6, 127.9 (CH×2), 127.7 (CH×2), 81.1, 69.9, 35.1, 31.7, 24.9, 22.5, 14.4 (the ipso carbon (attached to B) signal was not observed due to low intensity); HRMS (ESI-QTOF) calculated for [C$_{15}$H$_{23}$BO$_3$–H]$^-$=261.1667, found 261.1681.

Example 48

Synthesis of (E)-2-[3-(allyloxy)oct-1-en-1-yl]-4,4,5,5-tetramethyl-1,3,2-dioxaborolane (2.8d)

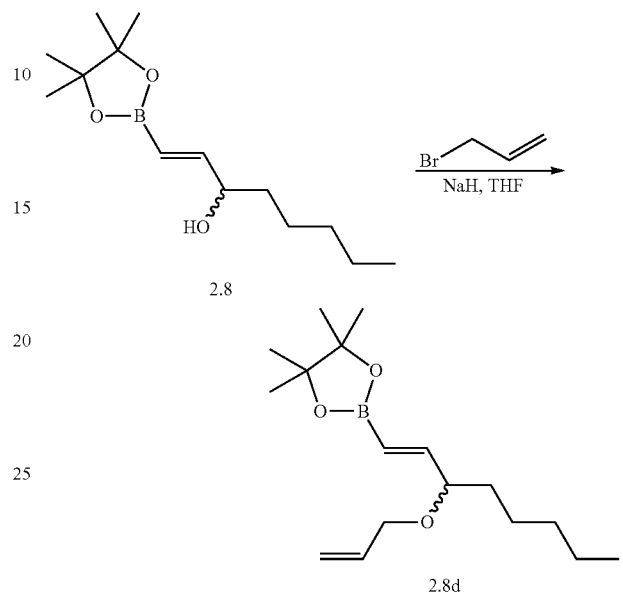

To a solution of 2.8 (1.3 g, 5.1 mmol) in THF (13 mL) was added a suspension of pre-washed NaH (0.8 g, 20 mmol) in THF (10 mL). The resulting suspension was heated at reflux for 30 min and was added allyl bromide (2.0 mL, 23 mmol). The resulting suspension was heated at reflux for 2 hours. The reaction mixture was cooled to ambient temperature and poured into ice. The mixture was extracted with EtOAc (30 mL×2) and the combined organic extracts were dried over MgSO$_4$ (2.0 g). The volatiles were removed in vacuo and the residue was purified by column chromatography (40 g SiO$_2$; eluting with 1:20 (v/v) MTBE-n-heptane (500 mL) to give the title compound (2.8d, 861 mg, 2.93 mmol, 57% yield).

$^1$H NMR (400 MHz, CDCl$_3$): δ 6.45 (dd, J=18.0, 6.4 Hz, 1H), 5.90 (m, 1H), 5.59 (dd, J=18.0, 0.8 Hz, 1H), 5.26 (dd, J=17.2, 3.6 Hz, 1H), 5.15 (dd, J=17.2, 3.6 Hz, 1H), 4.05 (m, 1H), 3.79 (m, 2H), 1.48 (m, 2H), 1.38 (m, 6H), 1.28 (s, 12H), 0.88 (m, 3H); $^{13}$C NMR (100 MHz, CDCl$_3$): δ 153.5, 135.1, 119.5, 116.5, 83.2 (CH×2), 81.3, 69.6, 35.0, 31.8, 25.0, 24.8 (CH×4), 22.5, 14.0.

Example 49

Synthesis of (E)-[3-(allyloxy)oct-1-en-1-yl]boronic acid (3.8d)

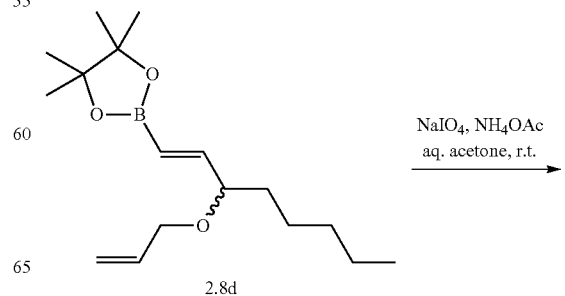

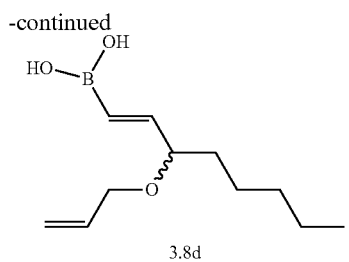

3.8d

To a solution of 2.8d (1.1 g, 3.7 mmol) in acetone and water (150 mL, 2:1 v/v) was added NaIO$_4$ (2.6 g, 12.0 mmol) and NH$_4$OAc (0.9 g, 11.1 mmol). The resulting cloudy solution was stirred at 40° C. for 24 hours and was concentrated under reduced pressure to remove acetone. The residue was diluted with EtOAc (60 mL) and the layers were separated. The aqueous layer was back-extracted with EtOAc (60 mL) and the combined organic layers were washed with brine (100 mL), dried over MgSO$_4$ (2.0 g), filtered, and concentrated under reduced pressure to provide the crude mixture which was purified by column chromatography (30 g SiO$_2$; eluting with 1:10 (v/v) MTBE-n-heptane (100 mL) then 1:3 (400 mL) to give the title compound (3.8d, 679 mg, 3.2 mmol, 86% yield).

$^1$H NMR (400 MHz, DMSO-d$_6$): δ 7.64 (s, 2H), 6.24 (dd, J=18.0, 7.2 Hz, 1H), 5.85 (m, 1H), 5.46 (d, J=18.0, 1H), 5.21 (dd, J 17.2, 3.6 Hz, 1H), 5.10 (dd, J=10.4, 1.6 Hz, 1H), 3.93 (m, 1H), 3.77 (m, 1H), 3.71 (m, 1H), 1.37 (m, 2H), 1.24 (m, 6H), 0.84 (m, 3H); $^{13}$C NMR (100 MHz, DMSO-d$_6$): δ 149.4, 135.5, 125.9, 115.6, 80.7, 68.4, 34.6, 31.2, 24.4, 22.0, 13.8; HRMS (ESI-QTOF) calculated for [C$_{11}$H$_{21}$BO$_3$–H]$^-$=211.1511, found 211.1527.

Example 50

Synthesis of 2-(oct-1-yn-3-yloxy)tetrahydro-2H-pyran (1.8e)

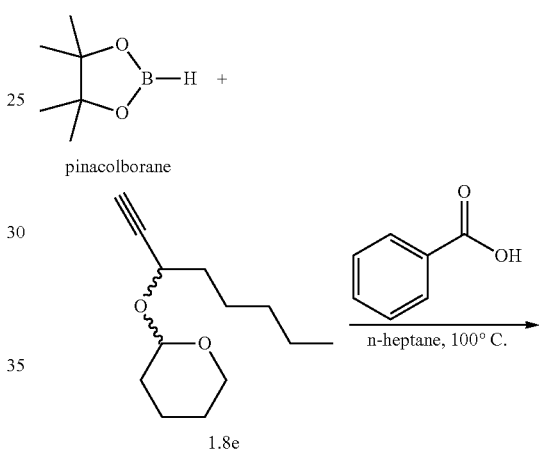

To a solution of oct-1-yn-3-ol (11.6 mL, 76.2 mmol), DHP (13.9 mL, 152 mmol) in CH$_2$Cl$_2$ (100 mL) at 0-5° C. was added PPTS (950 mg, 3.78 mmol) in CH$_2$Cl$_2$ (2.0 mL). The reaction mixture was allowed to warm up to room temperature and stirred for 4 hours. After diluting with CH$_2$Cl$_2$ (100 mL), sat. aq. NH$_4$Cl (200 mL) was added. The layers were separated and the aqueous layer was back-extracted with CH$_2$Cl$_2$ (100 mL×2). The organic layers were combined, washed with brine, dried over MgSO$_4$, and concentrated. Column chromatography (eluting with 1:20 (v/v) EtOAc-n-heptane) afforded the title compound as a mixture of four diastereomers as a colorless liquid (1.8e, 14.22 g, 89% as a diastereomeric mixture).

$^1$H NMR (400 MHz, CDCl$_3$): δ 4.98-4.74 (m, 1H), 4.43-4.25 (m, 1H), 4.05-3.77 (m, 1H), 3.56-3.50 (m, 1H), 2.43-2.37 (m, 1H), 1.79-1.60 (m, 4H), 1.59-1.42 (m, 6H), 1.35-1.28 (m, 4H), 0.91-0.84 (m, 3H); $^{13}$C NMR (100 MHz, CDCl$_3$): δ 98.2, 95.5, 84.0, 83.0, 73.1, 72.5, 67.1, 64.7, 62.3, 62.2, 35.6, 35.5, 31.5 (×2), 30.5 (×2), 25.5, 25.4, 25.0, 24.7, 22.5 (×2), 19.3, 19.1, 14.0 (×2).

Example 51

Synthesis of (E)-2-[3-(tetrahydro-2H-pyranoxy)oct-1-en-1-yl]-4,4,5,5-tetramethyl-1,3,2-dioxaborolane (2.8e)

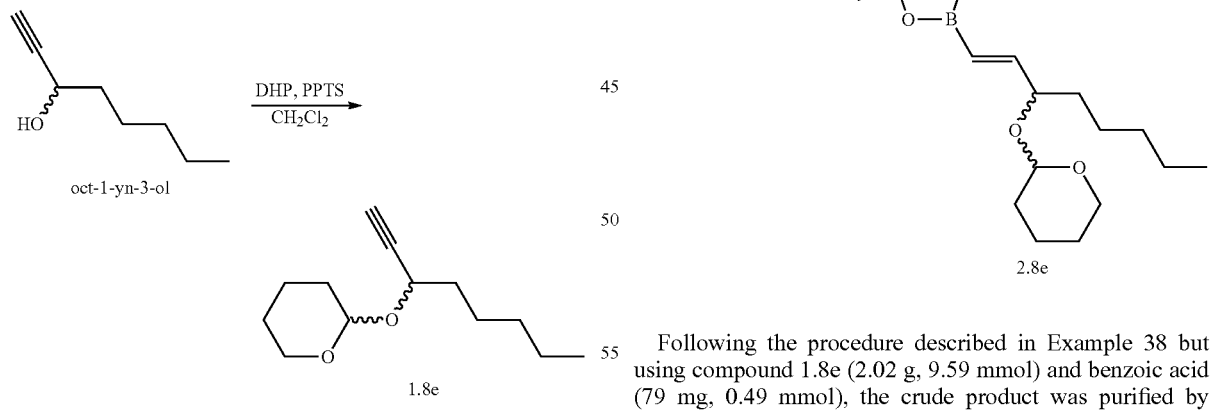

Following the procedure described in Example 38 but using compound 1.8e (2.02 g, 9.59 mmol) and benzoic acid (79 mg, 0.49 mmol), the crude product was purified by column chromatography (eluting with 1:20 (v/v) MTBE-n-heptane) affording 2.8e (2.31 g, 71% as a diastereomeric mixture).

$^1$H NMR (400 MHz, CDCl$_3$): δ 6.63 (dd, J=18.2, 5.4 Hz, 0.5 H), 6.42 (dd, J=18.0, 6.4 Hz, 0.5H), 5.69 (dd, J=18.0, 1.6 Hz, 0.5H), 5.57 (dd, J=18.0, 0.8 Hz, 0.5H), 4.73 (t, J=3.6 Hz, 0.5H), 4.61 (t, J=3.4 Hz, 0.5H), 4.19-4.11 (m, 1H), 3.88-3.84 (m, 1H), 3.51-3.42 (m, 1H), 1.88-1.82 (m, 1H), 1.75-1.68 (m, 1H), 1.65-1.27 (m, 24H), 0.90-0.86 (m, 3H); $^{13}$C NMR (100 MHz, CDCl$_3$): δ 153.9, 153.2, 119.9 (br), 96.8, 95.7, 83.2, 83.1, 77.3, 77.1, 62.3, 62.1, 35.3, 33.8, 31.9, 31.8, 30.7, 25.5, 25.4, 25.1, 24.79, 24.75, 24.71, 24.67, 24.5, 22.5, 19.6, 19.3, 14.0.

Example 52

Synthesis of (E)-[3-(tetrahydro-2H-pyranoxy)oct-1-en-1-yl]boronic acid (3.8e)

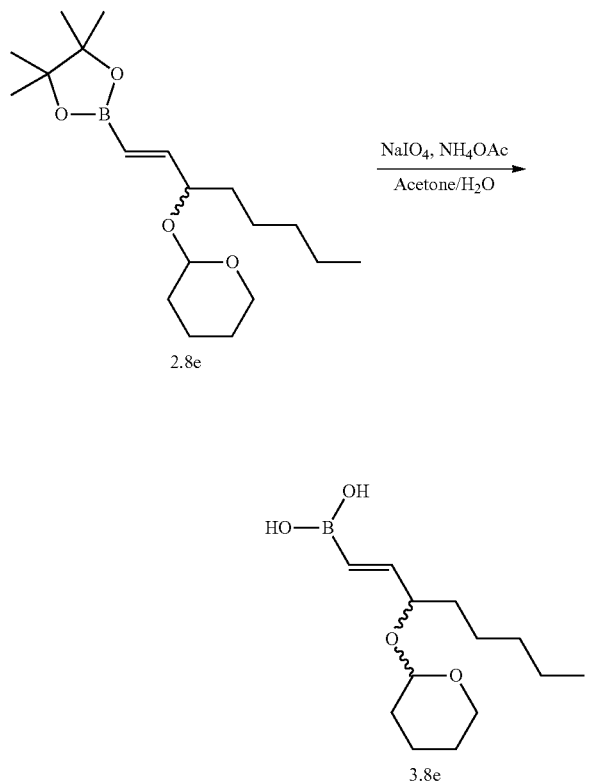

Following the procedure described in Example 39 but using compound 2.8e (950 mg, 2.80 mmol), the crude product was purified by column chromatography (eluting with 1:10 (v/v) EtOAc-n-heptane) affording 3.8e (495 mg, 69% as a diastereomeric mixture).

$^1$H NMR (400 MHz, DMSO-d$_6$): δ 7.65 (s, 1H), 7.59 (s, 1H), 6.40 (dd, J=18.0, 5.6 Hz, 0.5H), 6.21 (dd, J=18.0, 6.8 Hz, 0.5H), 6.45 (t, J=18.4 Hz, 1H), 4.65 (d, J=3.2 Hz, 0.5H), 4.51 (d, J=3.6 Hz, 0.5H), 4.01-3.98 (m, 1H), 3.78-3.71 (m, 1H), 3.43-3.39 (m, 1H), 1.74-1.70 (m, 1H), 1.62-1.58 (m, 1H), 1.51-1.40 (m, 6H), 1.26-1.24 (m, 6H), 0.87-0.84 (m, 3H); $^{13}$C NMR (100 MHz, DMSO-d$_6$): δ 150.74, 149.5, 126.7, 123.8, 97.1, 95.1, 78.0, 77.1, 61.9, 61.7, 35.4, 34.2, 31.81, 31.74, 31.68, 30.98, 30.84, 28.9, 25.62, 25.57, 25.1, 24.5, 22.5, 19.7, 19.6, 14.4; HRMS (ESI-QTOF) calculated for [C$_{13}$H$_{25}$BO$_4$-H]$^-$=255.1773, found 255.1785.

Example 53

Synthesis of (S)-tert-butyldimethyl(oct-1-yn-3-yloxy)silane (1.9a)

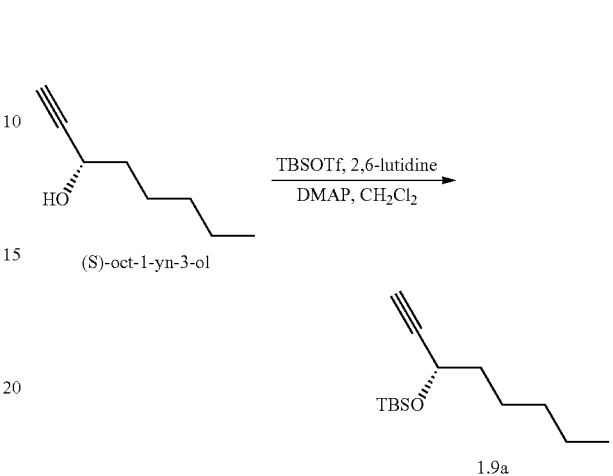

To a solution of (S)-oct-1-yn-3-ol (5.08 g, 40.3 mmol), 2,6-lutidine (8.49 g, 79.2 mmol) and DMAP (0.506 g, 4.14 mmol) in CH$_2$Cl$_2$ (70 mL) at 0-5° C. was added dropwise a solution of TBSOTf (15.8 g, 59.8 mmol) in CH$_2$Cl$_2$ (20 mL). The reaction mixture (light yellow solution) was allowed to warm up to room temperature and stirred 16 hours. After sat. aq. NH$_4$Cl (50 mL) was added, the organic layer was collected and the aqueous layer was extracted with CH$_2$Cl$_2$ (50 mL×2). The organic layers were combined, washed with brine (100 mL), dried over MgSO$_4$ (3.0 g), filtered and concentrated. Column chromatography (eluting with n-heptane then 1:20 (v/v) EtOAc-n-heptane) afforded 1.9a as a colorless liquid (8.52 g, 88.0%).

Example 54

Synthesis of (S,E)-tert-butyldimethyl{[1-(4,4,5,5-tetramethyl-1,3,2-dioxaborolan-2-yl)oct-1-en-3-yl]oxy}silane (2.9a)

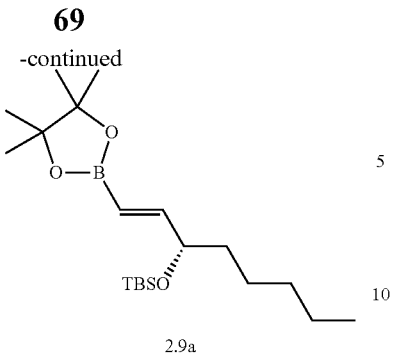

2.9a

To n-heptane (20.0 mL) was added 1.9a (4.9 g, 20.0 mmol), 5 mol % of 4-(dimethylamino)benzoic acid (170 mg, 1.0 mmol) and pinacolborane (9.2 mL, 62 mmol; neat oil) under N₂ atmosphere at ambient temperature. The solution was heated by 100° C. bath for 5 hours and was cooled to room temperature. The mixture was diluted with EtOAc (40 mL) and sat. aq. NH₄Cl solution (50 mL) and the layers were separated. The aqueous layer was back-extracted with EtOAc (40 mL) and the combined organic layers were washed with brine (80 mL), dried over anhydrous MgSO₄ (3.0 g), filtered and concentrated under reduced pressure to afford the crude 2.9a which was purified by column chromatography (100 g SiO₂; eluting with n-heptane (400 mL) then 1:30 (v/v) MTBE-n-heptane (900 mL)) to give the title compound (2.9a, 6.83 g, 18.5 mmol, 91% yield).

Example 55

Synthesis of (S,E)-{3-[(tert-butyldimethylsilyl)oxy] oct-1-en-1-yl}boronic acid (3.9)

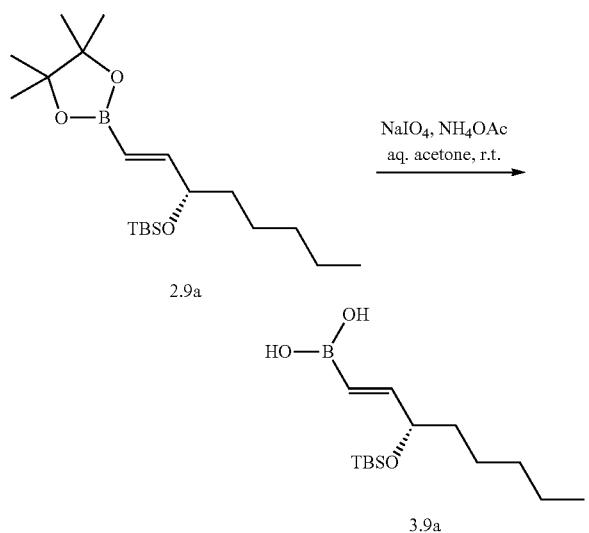

To a solution of 2.9a (9.29 g, 25.2 mmol) in acetone and water (540 mL, 2:1 v/v) was added NaIO₄ (15.0 g, 70.13 mmol) and NH₄OAc (5.15 g, 66.80 mmol). The resulting cloudy solution was stirred at 40° C. for 20 hours and was concentrated under reduced pressure to remove acetone. The residue was diluted with EtOAc (200 mL) and the layers were separated. The aqueous layer was back-extracted with EtOAc (200 mL) and the combined organic layers were washed with brine (200 mL), dried over MgSO₄ (5.0 g), filtered, and concentrated under reduced pressure to provide the title compound (3.9, 3.86 g, 13.5 mmol, 53.5%).

$[\alpha]^{20}_D$=−1.26 (c 1.0, MeOH); HRMS (ESI-QTOF) calculated for $[C_{14}H_{31}BO_3Si-H]^-$=285.2063, found 285.2078.

Example 56

Synthesis of (Z)-isopropyl 7-((1R,2R,3R)-3-[(tert-butyldimethylsilyl)oxy]-2-{(E)-3-[(tert-butyldimethylsilyl)oxy]-5-phenylpent-1-en-1-yl)}-5-oxocyclopentyl)hept-5-enoate (10.17)

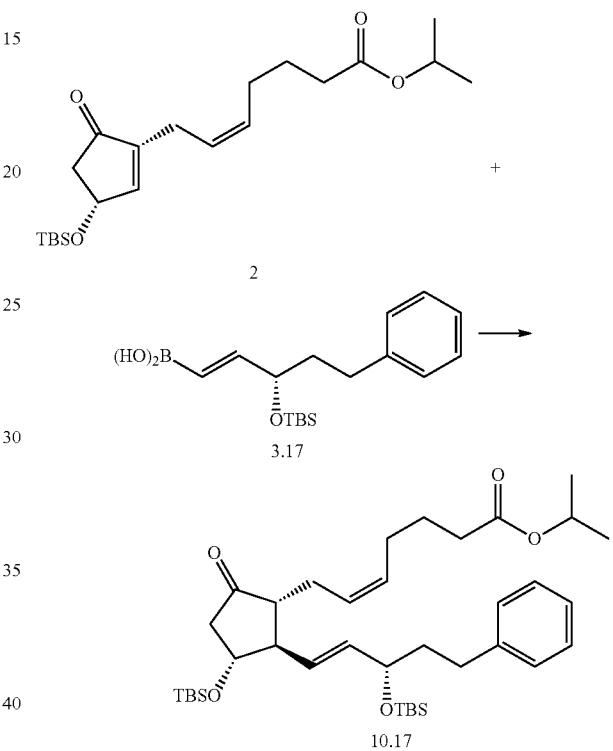

Following procedures described in Example 1 except using (S,E)-{3-[(tert-butyldimethylsilyl)oxy]-5-phenylpent-1-en-1-yl}boronic acid (3.17, 72.0 mg, 0.225 mmol), the reaction crude mixture was purified by column chromatography (eluting with 1:80 (v/v) acetone-hexanes) affording the title compound 10.17 (63 mg, 64%).

$[\alpha]^{29}_D$−35.9 (c 1.00, CHCl₃); ¹H NMR (400 MHz): δ 0.03 (s, 3H), 0.05 (s, 3H), 0.06 (s, 3H), 0.07 (s, 3H), 0.87 (s, 9H), 0.92 (s, 9H), 1.22 (d, J=6.4 Hz, 6H), 1.57-1.72 (m, 3H), 1.74-1.89 (m, 2H), 1.92-2.11 (m, 3H), 2.11-2.43 (m, 4H), 2.52 (dt, J=7.6, 10.8 Hz, 1H), 2.56-2.74 (m, 3H), 4.08 (q, J=7.6 Hz, 1H), 4.20 (q, J=5.5 Hz, 1H), 4.99 (septet, J=6.4 Hz, 1H), 5.28-5.47 (m, 2H), 5.50-5.68 (m, 2H), 7.10-7.22 (m, 3H), 7.24-7.32 (m, 2H); ¹³C NMR (100 MHz): δ −4.7 (CH₃), −4.63 (CH₃), −4.59 (CH₃), −4.2 (CH₃), 18.0 (C), 18.2 (C), 21.8 (CH₃), 24.8 (CH₂), 25.3 (CH₂), 25.8 (CH₃), 25.9 (CH₃), 26.7 (CH₂), 31.6 (CH₂), 34.1 (CH₂), 40.2 (CH₂), 47.7 (CH₂), 52.7 (CH), 53.9 (CH), 67.4 (CH), 72.1 (CH), 73.3 (CH), 125.7 (CH), 126.6 (CH), 128.27 (CH), 128.33 (CH), 129.2 (CH), 130.9 (CH), 135.9 (CH), 142.3 (C), 173.1 (C), 215.3 (C); HRMS (ESI): calculated for $[C_{38}H_{64}O_5Si_2+NH_4]^+$=674.4631, found 674.4611; FTIR (KBr, neat) 3465, 2950, 2859, 1736, 1630, 1462, 1376, 1252, 1103, 1020, 834 cm⁻¹.

Example 57

Synthesis of (Z)-isopropyl 7-((1R,2R,3R)-3-((tert-butyldimethylsilyl)oxy)-2-((E)-3-((tert-butyldimethylsilyl)oxy)-4-(3-(trifluoromethyl)phenoxy)but-1-en-1-yl)-5-oxocyclopentyl)hept-5-enoate (10.18)

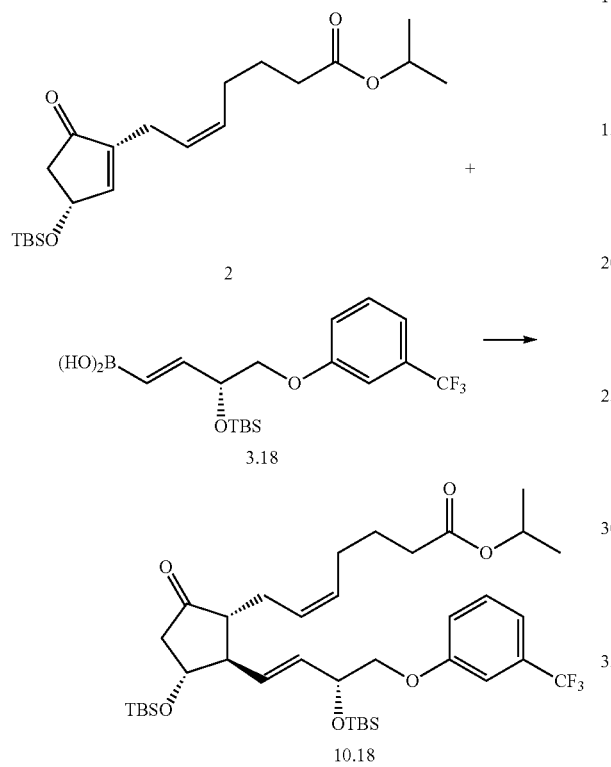

Following procedures described in Example 1 except using (R,E)-{3-[(tert-butyldimethylsilyl)oxy]-4-[3-(trifluoromethyl)phenoxy]but-1-en-1-yl}boronic acid (3.17, 88 mg, 0.225 mmol), the reaction crude mixture was purified by column chromatography (eluting with 1:80 (v/v) acetone-hexanes) affording the title compound 10.18 (71 mg, 65%).

$[\alpha]^{29}_D$ −35.6 (c 1.00, CHCl$_3$); $^1$H NMR (400 MHz): δ 0.04 (s, 3H), 0.05 (s, 3H), 0.100 (s, 3H), 0.104 (s, 3H), 0.87 (s, 9H), 0.91 (s, 9H), 1.21 (d, J=6.2 Hz, 6H), 1.58-1.72 (m, 3H), 1.92-2.11 (m, 2H), 2.12-2.45 (m, 4H), 2.52 (dt, J=7.6, 11.2 Hz, 1H), 2.55-2.70 (m, 1H), 3.80-3.92 (m, 2H), 4.07 (q, J=8.4 Hz, 1H), 4.50-4.62 (m, 1H), 4.98 (septet, J=6.4 Hz, 1H), 5.25-5.45 (m, 2H), 5.65-5.82 (m, 2H), 7.03 (dd, J=2.0, 8.0 Hz, 1H), 7.08 (s, 1H), 7.20 (d, J=7.6 Hz, 2H), 7.38 (dd, J=8.0, 8.0 Hz, 1H); $^{13}$C NMR (100 MHz): δ −4.5 (CH$_3$), −4.6 (CH$_3$), −4.7 (CH$_3$), 18.0 (C), 18.3 (C), 21.8 (CH$_3$), 24.8 (CH$_2$), 25.1 (CH$_2$), 25.7 (CH$_3$), 25.8 (CH$_2$), 26.7 (CH$_2$), 30.9 (CH$_3$), 34.1 (CH$_2$), 47.6 (CH$_2$), 53.1 (CH), 54.1 (CH), 67.4 (CH), 70.9 (CH), 72.6 (CH$_2$), 72.9 (CH), 111.0 (q, J=4.0 Hz, CH), 117.5 (q, J=4.0 Hz, CH), 123.9 (q, J=271.0 Hz, C), 126.5 (CH), 130.0 (CH), 130.9 (CH), 131.5 (CH), 131.9 (q, J=32.2 Hz, C), 132.3 (CH), 158.9 (C), 173.0 (C), 214.7 (C); HRMS (ESI): calculated for [C$_{38}$H$_{61}$F$_3$O$_6$Si$_2$+ NH$_4$]$^+$=744.4297, found 744.4291; FTIR (KBr, neat) 2945, 2862, 1737, 1602, 1457, 1330, 1249, 1167, 1123, 839 cm$^{-1}$.

Example 58

Synthesis of isopropyl (Z)-7-{(1R,2R,3R)-2-[(1E,5E)-3-(benzyloxy)-4,4-difluoroocta-1,5-dien-1-yl]-3-[(tert-butyldimethylsilyl)oxy]-5-oxocyclopentyl}hept-5-enoate (10.19)

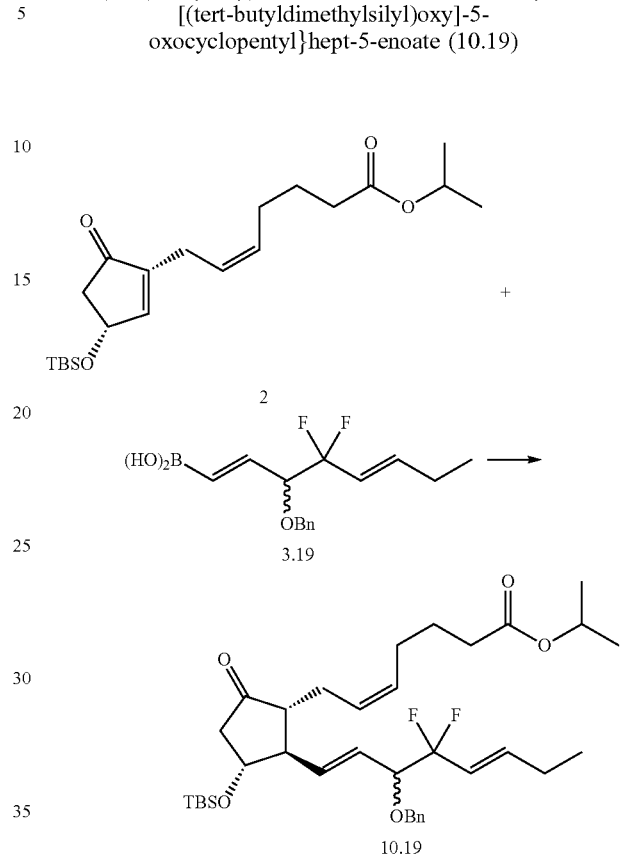

Following procedures described in Example 1 except using 2-((1E,5E)-3-(benzyloxy)-4,4-difluoroocta-1,5-dien-1-yl)-4,4,5,5-tetramethyl-1,3,2-dioxaborolane (2.19, 85 mg, 0.225 mmol), the reaction crude mixture was purified by column chromatography (eluting with 1:80 (v/v) acetone-hexanes) affording isopropyl (Z)-7-{(1R,2R,3R)-2-[(1E,5E)-3-(benzyloxy)-4,4-difluoroocta-1,5-dien-1-yl]-3-[(tert-butyldimethylsilyl)oxy]-5-oxocyclopentyl}hept-5-enoate (10.19, 27 mg, 28% as a pair of diastereomers).

$[\alpha]^{22}_D$ −51.8 (c 0.33, CHCl$_3$); $^1$H NMR (400 MHz): δ 0.035 (s, 1.5H), 0.044 (s, 1.5H), 0.052 (s, 1.5H), 0.065 (s, 1.5H), 0.88 (s, 9H), 1.03 (t, J=7.4 Hz, 3H), 1.21 (d, J=6.4 Hz, 6H), 1.62-1.70 (m, 1H), 2.01-2.16 (m, 6H), 2.16-2.30 (m, 2H), 2.28-2.43 (m, 2H), 2.53-2.60 (m, 1H), 2.62-2.69 (m, 1H), 3.93-4.15 (m, 2H), 4.51 (d, J=12.0 Hz, 0.5H), 4.53 (d, J=12.0 Hz, 0.5H), 4.67 (d, J=12.0 Hz, 0.5H), 4.68 (d, J=12.0 Hz, 0.5H), 4.98 (septet, J=6.4 Hz, 1H), 5.26-5.46 (m, 2H), 5.52-5.68 (m, 2H), 5.69-5.82 (m, 1H), 6.11-6.23 (m, 1H), 7.29-7.32 (m, 6H); $^{13}$C NMR (100 MHz): δ −4.87 (CH$_3$), −4.74 (CH$_3$), −4.67 (CH$_3$), −4.52 (CH$_3$), 12.7 (CH$_3$), 18.0 (C), 21.8 (CH$_3$), 24.79 (CH$_2$), 24.81 (CH$_2$), 25.0 (CH$_2$), 25.2 (CH$_2$), 25.72 (CH$_3$), 25.74 (CH$_3$), 26.63 (CH$_2$), 26.66 (CH$_2$), 34.05 (CH$_2$), 34.06 (CH$_2$), 47.7 (CH$_2$), 53.1 (CH), 53.2 (CH), 53.75 (CH), 53.82 (CH), 67.4 (CH), 71.3 (CH$_2$), 71.5 (CH$_2$), 72.8 (CH), 73.0 (CH), 81.0 (q, J=31.0 Hz, CH), 121.5 (q, J=25.3 Hz, CH), 126.2 (CH), 126.3 (CH), 126.4 (CH), 127.7 (CH), 127.80 (CH), 127.84 (CH), 128.37 (CH), 128.41 (CH), 131.2 (CH), 131.3 (CH), 136.8 (CH), 137.2 (CH), 137.5 (C), 137.6 (C), 138.9 (q, J=8.7 Hz, CH), 173.09

(C), 173.12 (C), 214.5 (C); HRMS (ESI-QTOF) calculated for $[C_{36}H_{54}F_2O_5Si+Na]^+$=655.3601, found 655.3620; FTIR (KBr, neat) 3460, 2938, 2867, 1738, 1630, 1461, 1377, 1253, 1214, 1109, 974, 873 cm$^{-1}$.

Example 59

Synthesis of (Z)-isopropyl 7-{(1R,2R,3R,5S)-3-[(tert-butyldimethylsilyl)oxy]-2-((E)-3,3-difluoro-4-phenoxybut-1-en-1-yl)-5-hydroxycyclopentyl}hept-5-enoate (11.7)

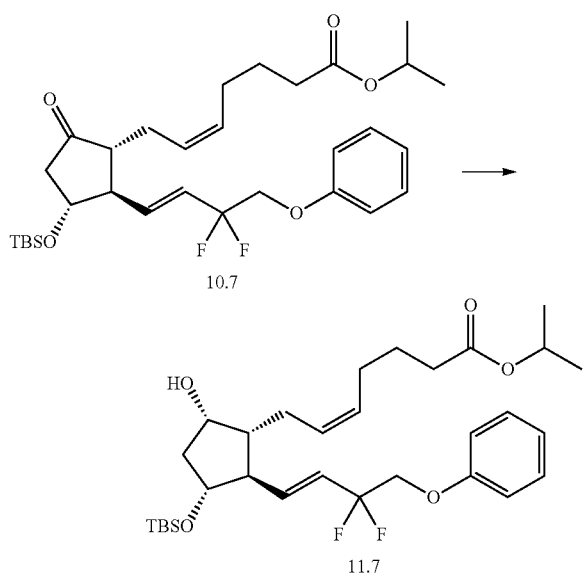

To a THF (15 mL) solution of compound 10.7 obtained in Example 8 (1.42 g, 2.51 mmol) was added a solution of L-Selectride® (3.45 mL, 1.0 M in THF, 3.45 mmol) at −78° C. The mixture was stirred at −78° C. for 40 min then sat. aq. NH$_4$Cl$_{(aq)}$ (5 mL) was added. The aqueous layer was separated and extracted with EtOAc (15 mL×3). The organic layers were combined, dried over anhydrous Na$_2$SO$_4$, filtered and evaporated to afford an oily crude product, which was purified by column chromatography (eluting with 1:8 (v/v) EtOAc-hexanes) to afford the title compound 11.7 (1.34 g, 94%)

$[\alpha]^{26}_D$ −9.4 (c 0.11, CHCl$_3$); $^1$H NMR (400 MHz): δ 0.027 (s, 3H), 0.034 (s, 3H), 0.86 (s, 9H), 1.22 (d, J=6.2 Hz, 6H), 1.52-1.61 (m, 1H), 1.65 (quintet, J=7.5 Hz, 2H), 1.73-1.82 (m, 1H), 2.03-2.18 (m, 4H), 2.20-2.46 (m, 5H), 4.02 (quintet, J=3.5 Hz, 1H), 4.06-4.32 (m, 3H), 4.99 (septet, J=6.2 Hz, 1H), 5.28-5.59 (m, 2H), 5.76 (dt, J=11.1, 15.6 Hz, 1H), 6.14 (ddt, J=2.4, 9.3, 15.7 Hz, 1H), 6.89-6.92 (m, 2H), 7.01 (t, J=7.4 Hz, 1H), 7.26-7.31 (m, 2H); $^{13}$C NMR (100 MHz): δ −4.9 (CH$_3$), −4.7 (CH$_3$), 17.9 (C), 21.8 (CH$_3$), 24.9 (CH$_2$), 25.7 (CH$_3$), 26.1 (CH$_2$), 26.6 (CH$_2$), 34.1 (CH$_2$), 43.4 (CH$_2$), 50.4 (CH), 55.7 (CH), 67.4 (CH), 69.5 (t, J=35.0 Hz, C), 73.5 (CH), 78.5 (CH), 114.7 (CH), 118.1 (t, J=239.0 Hz, C), 121.7 (CH), 123.6 (t, J=25.0 Hz, CH), 128.8 (CH), 129.5 (CH), 129.8 (CH), 138.6 (t, J=9.0 Hz, CH), 158.0 (C), 173.2 (C); HRMS (ESI-QTOF) calculated for $[C_{31}H_{48}F_2O_5Si+H]^+$=567.3312, found 567.3316; FTIR (KBr, neat) 3451, 2954, 2879, 1724, 1595, 1498, 1463, 1375, 1301, 1246, 1101 cm$^{-1}$.

Example 60

Synthesis of tafluprost ((Z)-isopropyl 7-[(1R,2R,3R,5S)-2-((E)-3,3-difluoro-4-phenoxybut-1-en-1-yl)-3,5-dihydroxycyclopentyl]hept-5-enoate; 12.7)

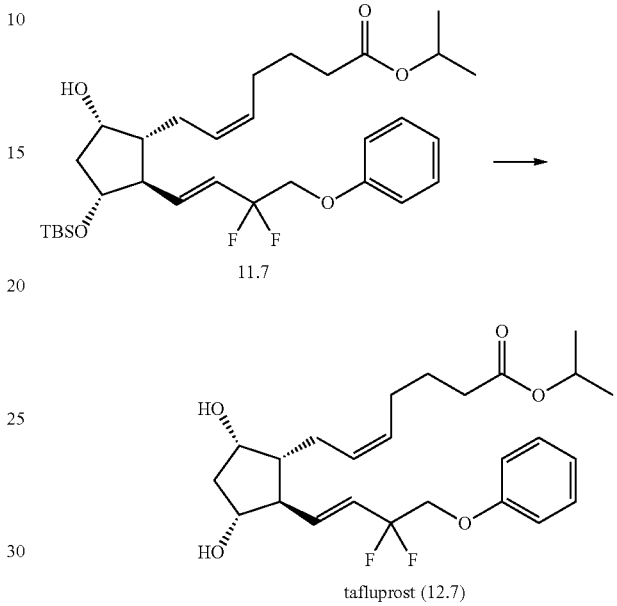

tafluprost (12.7)

To a THF (7 mL) solution of compound 11.7 obtained in Example 59 (2.11 g, 3.73 mmol) was added n-Bu$_4$NF (4.5 mL, 1.0 M in THF, 4.5 mmol) at 0° C. and the mixture was warmed to room temperature in 30 min and stirred for another 3 h. Sat. aq. NH$_4$Cl$_{(aq)}$ was added to quench the reaction and the layers were separated. The aqueous phase was extracted with EtOAc (20 mL×3) and the organic layers were combined, dried over anhydrous Na$_2$SO$_4$, filtered and evaporated to afford the crude product, which was purified by column chromatography (hexane/EtOAc=1:5) to afford the title compound tafluprost (12.7, 1.52 g, 90%).

$[\alpha]^{23}_D$ 21.6 (c 1.00, CHCl$_3$); $^1$H NMR (600 MHz): δ 1.22 (d, J=6.3 Hz, 6H), 1.58-1.69 (m, 3H), 1.85 (dt, J=1.2, 14.4 Hz, 1H), 2.03-2.14 (m, 6H), 2.26 (dt, J=3.0, 7.4 Hz, 2H), 2.28-2.38 (m, 1H), 2.47 (dt, J=4.2, 9.6 Hz, 1H), 4.00-4.04 (m, 1H), 4.15-4.25 (m, 3H), 5.00 (septet, J=6.3 Hz, 1H), 5.33-5.43 (m, 2H), 5.80 (dt, J=11.1, 15.7 Hz, 1H), 6.10 (ddt, J=2.3, 9.1, 15.7 Hz, 1H), 6.91-6.92 (m, 2H), 6.97-7.02 (m, 1H), 7.28-7.31 (m, 2H); $^{13}$C NMR (150 MHz): δ 21.80 (CH$_3$), 21.82 (CH$_3$), 24.8 (CH$_2$), 25.7 (CH$_2$), 26.6 (CH$_2$), 34.0 (CH$_2$), 43.0 (CH$_2$), 50.5 (CH), 55.8 (CH), 67.7 (CH), 69.3 (t, J=34.5 Hz, CH$_2$), 73.3 (CH), 78.0 (CH), 114.8 (CH), 118.2 (t, J=240.0 Hz, C), 121.8 (CH), 123.6 (t, J=24.8 Hz, CH), 128.6 (CH), 129.6 (CH), 130.1 (CH), 138.6 (t, J=8.3 Hz, CH), 158.0 (C), 173.4 (C); $^{19}$F NMR (564 MHz): δ −103.4 (d, J=255.2 Hz), −104.1 (d, J=255.5 Hz); HRMS (ESI-QTOF): calculated for $[C_{25}H_{34}F_2O_5+H]^+$=453.2447, found 453.2449; FTIR (KBr, neat) 3410, 2929, 1720, 1593, 1494, 1376, 1247, 1156, 1103, 1052 cm$^{-1}$.

Example 61

Synthesis of isopropyl (Z)-7-((1R,2R,3R)-2-{(E)-3-acetoxyoct-1-en-1-yl)-3-[(tert-butyldimethylsilyl)oxy]-5-oxocyclopentyl}hept-5-enoate (10.8b)

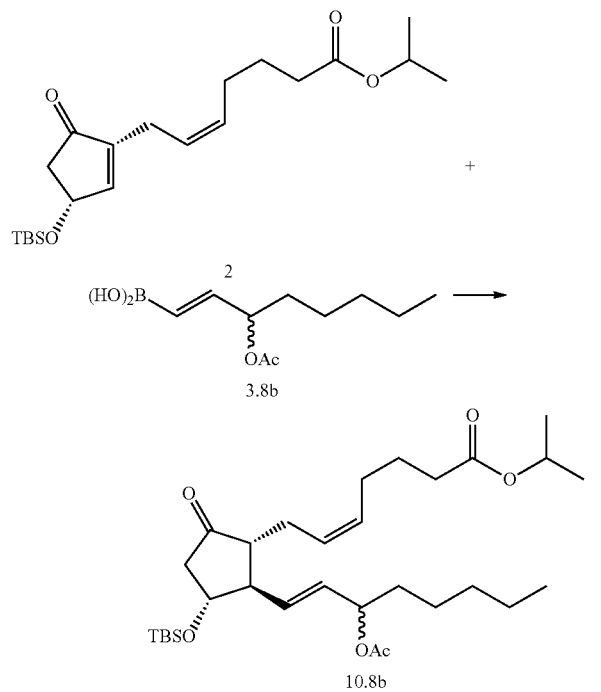

Following procedures described in Example 1 except using (E)-(3-acetoxyoct-1-en-1-yl)boronic acid (3.8b, 48 mg, 0.225 mmol), the reaction crude mixture was purified by column chromatography (eluting with 1:80 (v/v) acetone-hexanes) affording isopropyl (Z)-7-((1R,2R,3R)-2-{(E)-3-acetoxyoct-1-en-1-yl)-3-[(tert-butyldimethylsilyl)oxy]-5-oxocyclopentyl}hept-5-enoate (10.8b, 20 mg, 24% as a pair of diastereomers).

$[\alpha]^{24}_D$ −94.2 (c 0.23, CHCl$_3$); $^1$H NMR (400 MHz): δ 0.046 (s, 3H), 0.054 (s, 3H), 0.82-0.92 (m, 12H), 1.24 (d, J=6.2 Hz, 6H), 1.26-1.36 (m, 7H), 1.60-1.70 (m, 3H), 1.98-2.09 (m, 6H), 2.14 (qd, J=2.1, 9.1 Hz, 1H), 2.25 (t, J=7.6 Hz, 2H), 2.29-2.52 (m, 3H), 2.63 (dd, J=7.2, 18.3 Hz, 1H), 4.015 (q, J=8.4 Hz, 0.5H), 4.023 (q, J=8.4 Hz, 0.5H), 4.99 (septet, J=6.2 Hz, 1H), 5.21-5.34 (m, 2H), 5.35-5.45 (m, 1H), 5.47-5.65 (m, 2H); $^{13}$C NMR (100 MHz): δ −4.81 (CH$_3$), −4.80 (CH$_3$), −4.7 (CH$_3$), −4.6 (CH$_3$), 13.99 (CH$_3$), 18.0 (C), 21.3 (CH$_3$), 21.9 (CH$_3$), 22.50 (CH$_2$), 22.52 (CH$_2$), 24.8 (CH$_2$), 25.0 (CH$_2$), 25.1 (CH$_2$), 26.6 (CH$_2$), 26.7 (CH$_2$), 30.9 (CH$_2$), 31.5 (CH$_2$), 31.6 (CH$_2$), 34.06 (CH$_2$), 34.08 (CH$_2$), 34.5 (CH$_2$), 34.6 (CH$_2$), 47.6 (CH$_2$), 53.3 (CH), 53.3 (CH), 53.94 (CH), 53.3.96 (CH), 67.4 (CH), 72.72 (CH), 72.74 (CH), 74.2 (CH), 74.3 (CH), 126.47 (CH), 126.53 (CH), 130.9 (CH), 131.0 (CH), 131.77 (CH), 131.84 (CH), 133.17 (CH), 133.24 (CH), 170.15 (C), 170.19 (C), 173.1 (C), 214.6 (C); HRMS (ESI-QTOF) calculated for [C$_{31}$H$_{54}$O$_6$Si+NH$_4$]$^+$=568.4028, found 568.4047; FTIR (KBr, neat): 3442, 2932, 2861, 1737, 1641, 1378, 1237, 1107, 963, 838 cm$^{-1}$.

Example 62

Synthesis of isopropyl (Z)-7-((1R,2R,3R)-3-[(tert-butyldimethylsilyl)oxy]-5-oxo-2-{(E)-3-[(tetrahydro-2H-pyran-2-yl)oxy]oct-1-en-1-yl}cyclopentyl)hept-5-enoate (10.8e)

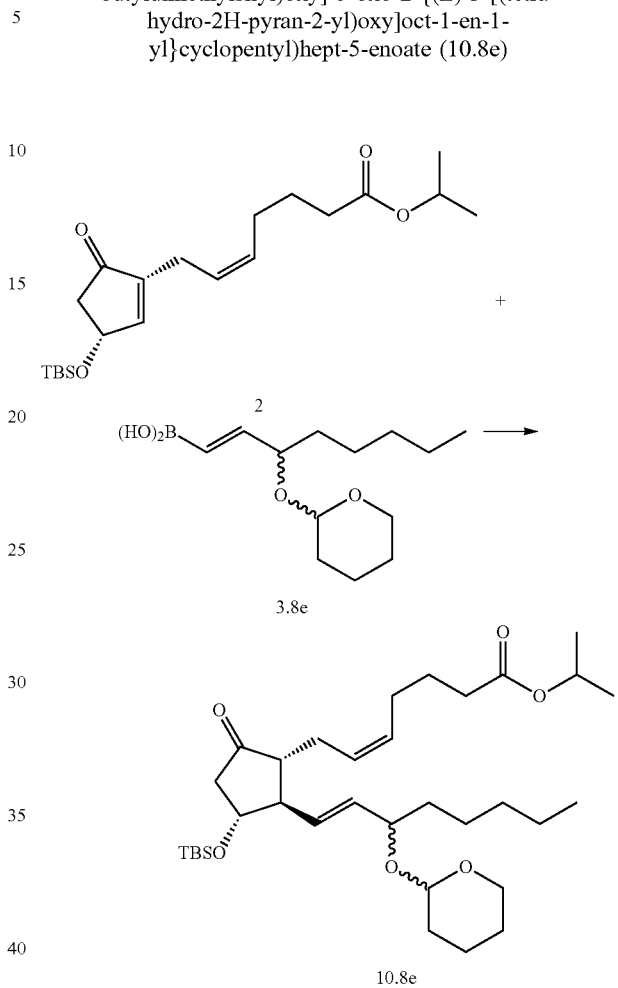

Following procedures described in Example 1 except using (E)-(3-((tetrahydro-2H-pyran-2-yl)oxy)oct-1-en-1-yl) boronic acid (3.8e, 58 mg, 0.225 mmol), the reaction crude mixture was purified by column chromatography (eluting with 1:80 (v/v) acetone-hexanes) affording isopropyl (Z)-7-((1R,2R,3R)-3-[(tert-butyldimethylsilyl)oxy]-5-oxo-2-{(E)-3-[(tetrahydro-2H-pyran-2-yl)oxy]oct-1-en-1-yl}cyclopentyl)hept-5-enoate (10.8e) (56 mg, 63% as a diastereomeric mixture).

$[\alpha]^{24}_D$ −62.9 (c 0.36, CHCl$_3$); $^1$H NMR (400 MHz): δ 0.03 (s, 1.5H), 0.04 (s, 1.5H), 0.05 (s, 1.5H), 0.06 (s, 1.5H), 0.79-0.94 (m, 12H), 1.21 (d, J=6.3 Hz, 6H), 1.28-1.34 (m, 5H), 1.36-1.72 (m, 10H), 1.73-1.83 (m, 1H), 2.03-2.19 (m, 4H), 2.21-2.40 (m, 4H), 2.45-2.71 (m, 2H), 3.33-3.53 (m, 1H), 3.78-3.82 (m, 1H), 3.92-4.12 (m, 2H), 4.68-4.72 (m, 1H), 4.99 (septet, J=6.3 Hz, 1H), 5.28-5.43 (m, 2H), 5.48-5.66 (m, 2H); $^{13}$C NMR (100 MHz): δ −4.8 (CH$_3$), −4.7 (CH$_3$), −4.6 (CH$_3$), −4.5 (CH$_3$), 14.1 (CH$_3$), 17.95 (C), 18.0 (C), 19.42 (CH$_2$), 19.49 (CH$_2$), 19.51 (CH$_2$), 21.9 (CH$_3$), 22.6 (CH$_2$), 24.7 (CH$_2$), 24.8 (CH$_2$), 24.9 (CH$_2$), 25.1 (CH$_2$), 25.2 (CH$_2$), 25.3 (CH$_2$), 25.4 (CH$_2$), 25.5 (CH$_2$), 25.6 (CH$_2$), 25.75 (CH$_3$), 25.77 (CH$_3$), 26.7 (CH$_2$), 30.79 (CH$_2$), 30.82 (CH$_2$), 31.8 (CH$_2$), 31.9 (CH$_2$), 34.09 (CH$_2$), 34.11 (CH$_2$), 34.6 (CH$_2$), 34.8 (CH$_2$), 36.1 (CH$_2$), 47.7

(CH$_2$), 52.7 (CH), 52.9 (CH), 53.1 (CH), 53.8 (CH), 53.9 (CH), 62.0 (CH$_2$), 62.3 (CH$_2$), 67.38 (CH), 67.41 (CH), 73.09 (CH), 73.13 (CH), 73.3 (CH), 75.7 (CH), 76.5 (CH), 77.1 (CH), 94.8 (CH), 97.0 (CH), 97.3 (CH), 126.56 (CH), 126.62 (CH), 126.7 (CH), 130.2 (CH), 130.3 (CH), 130.85 (CH), 130.91 (CH), 132.8 (CH), 133.8 (CH), 134.2 (CH), 134.8 (C), 173.0 (C), 173.09 (C), 173.12 (C), 214.8 (C), 215.3 (C), 215.4 (C); HRMS (ESI): calculated for [C$_{34}$H$_{60}$O$_6$Si+Na]$^+$=615.4051, found 615.4063; FTIR (KBr, neat) 3424, 2937, 2862, 1737, 1638, 1463, 1375, 1248, 1113, 1020 cm$^{-1}$.

Example 63

Synthesis of isopropyl (Z)-7-{(1R,2R,3R)-3-[(tert-butyldimethylsilyl)oxy]-2-((E)-3-benzyloxy-1-en-1-yl)-5-oxocyclopentyl}hept-5-enoate (10.8c)

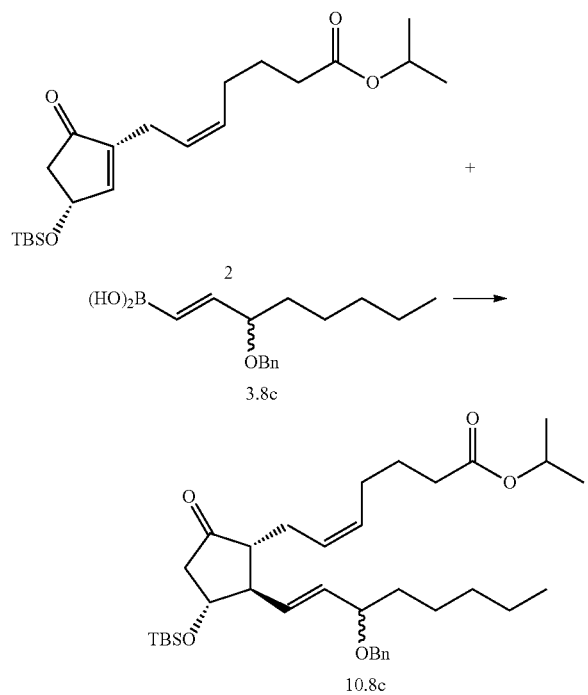

Following procedures described in Example 1 except using (E)-(3-(benzyloxy)oct-1-en-1-yl)boronic acid (3.8c, 59 mg, 0.225 mmol), the reaction crude mixture was purified by column chromatography (eluting with acetone-hexanes=1:80) affording isopropyl (Z)-7-((1R,2R,3R)-2-((E)-3-(benzyloxy)oct-1-en-1-yl)-3-((tert-butyldimethylsilyl)oxy)-5-oxocyclopentyl)hept-5-enoate (10.8c) (44mg, 50% as a pair of diastereomers).

Diastereomer 1: [α]$^{24}_D$-60.4 (c 0.63, CHCl$_3$); $^1$H NMR (400 MHz): δ 0.06 (s, 3H), 0.07 (s, 3H), 0.83-0.96 (m, 12H), 1.21 (d, J=6.2 Hz, 6H), 1.26-1.53 (m, 7H), 1.60-1.73 (m, 3H), 2.02-2.11 (m, 3H), 2.12-2.27 (m, 3H), 2.28-2.45 (m, 2H), 2.54 (dt, J=7.6, 11.4 Hz, 1H), 2.63 (dd, J=6.9, 18.2 Hz, 1H), 3.76 (q, J=6.5 Hz, 1H), 4.08 (q, J=8.3 Hz, 1H), 4.35 (d, J=11.9 Hz, 1H), 4.60 (d, J=11.9 Hz, 1H), 4.99 (septet, J=6.2 Hz, 1H), 5.29-5.48 (m, 2H), 5.49-5.64 (m, 2H), 7.27-7.37 (m, 5H); $^{13}$C NMR (100 MHz): δ -4.7 (CH$_3$), -4.5 (CH$_3$), 14.1 (CH$_3$), 18.0 (C), 21.9 (CH$_3$), 22.6 (CH$_2$), 24.8 (CH$_2$), 25.1 (CH$_2$), 25.3 (CH$_2$), 25.8 (CH$_3$), 26.7 (CH$_2$), 31.8 (CH$_2$), 34.1 (CH$_2$), 36.0 (CH$_2$), 47.7 (CH$_2$), 53.0 (CH), 53.9 (CH), 67.4 (CH), 70.3 (CH$_2$), 73.2 (CH), 79.9 (CH), 126.6 (CH), 127.4 (CH), 127.6 (CH), 128.3 (CH), 131.0 (CH), 132.3 (CH), 134.2 (CH), 138.9 (C), 173.0 (C), 214.9 (C); HRMS (ESI-QTOF) calculated for [C$_{36}$H$_{58}$O$_5$Si+Na]$^+$=621.3946, found 621.3961; FTIR (KBr, neat) 3448, 2932, 2862, 1736, 1461, 1370, 1246, 1105, 974, 837 cm$^{-1}$.

Diastereomer 2: [α]$^{24}_D$-37.2 (c 0.9, CHCl$_3$); $^1$H NMR (400 MHz): δ 0.04 (s, 3H), 0.05 (s, 3H), 0.81-0.91 (m, 12H), 1.21 (d, J=6.3 Hz, 6H), 1.24-1.58 (m, 7H), 1.62-1.72 (m, 3H), 2.04-2.26 (m, 6H), 2.32-2.60 (m, 3H), 2.65 (dd, J=7.0, 18.3 Hz, 1H), 3.69-3.80 (m, 1H), 4.08 (q, J=8.0 Hz, 1H), 4.35 (d, J=12.0 Hz, 1H), 4.59 (d, J=12.0 Hz, 1H), 4.98 (septet, J=6.3 Hz, 1H), 5.30-5.46 (m, 2H), 5.49-5.62 (m, 2H), 7.23-7.37 (m, 5H); $^{13}$C NMR (100 MHz): δ -4.7 (CH$_3$), -4.5 (CH$_3$), 14.1 (CH$_3$), 18.0 (C), 21.9 (CH$_3$), 22.6 (CH$_2$), 24.8 (CH$_2$), 25.1 (CH$_2$), 25.3 (CH$_2$), 25.8 (CH$_3$), 26.7 (CH$_2$), 31.8 (CH$_2$), 34.1 (CH$_2$), 35.9 (CH$_2$), 47.7 (CH$_2$), 53.2 (CH), 54.0 (CH), 67.4 (CH), 70.1 (CH$_2$), 73.0 (CH), 79.7 (CH), 126.5 (CH), 127.4 (CH), 127.6 (CH), 128.3 (CH), 131.1 (CH), 132.6 (CH), 134.2 (CH), 138.8 (C), 173.1 (C), 214.8 (C); FTIR (KBr, neat) 3443, 2931, 2853, 1736, 1459, 1373, 1246, 1106, 972, 836 cm$^{-1}$.

Example 64

Synthesis of isopropyl (Z)-7-{(1R,2R,3R)-3-[(tert-butyldimethylsilyl)oxy]-2-((E)-3-hydroxyoct-1-en-1-yl)-5-oxocyclopentyl}hept-5-enoate (10.8)

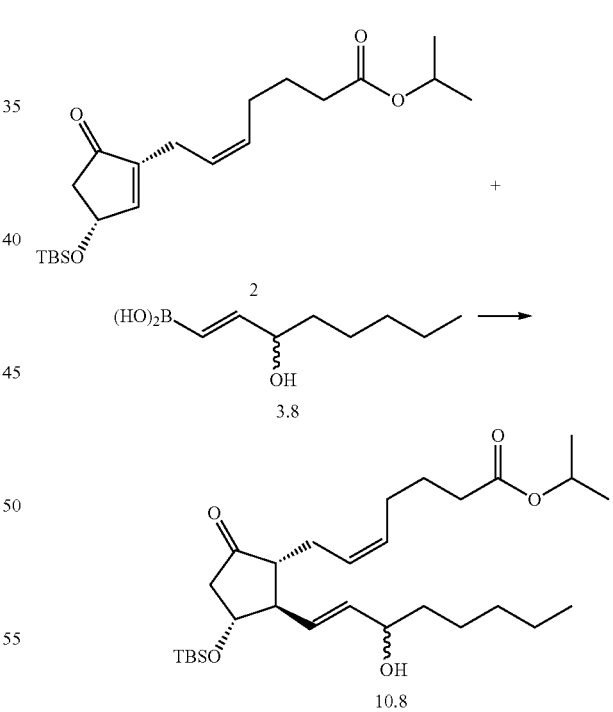

Following procedures described in Example 1 except using (E)-(3-hydroxyoct-1-en-1-yl)boronic acid (3.8, 39 mg, 0.225 mmol), the reaction crude mixture was purified by column chromatography (eluting with 1:80 (v/v) acetone-hexanes) affording isopropyl (Z)-7-{(1R,2R,3R)-3-[(tert-butyldimethylsilyl)oxy]-2-((E)-3-hydroxyoct-1-en-1-yl)-5-oxocyclopentyl}hept-5-enoate (10.8, 31 mg, 40% as a pair of diastereomers).

[α]$^{24}_D$ −60.7 (c 0.6, CHCl$_3$); $^1$H NMR (400 MHz): δ 0.03-0.05 (m, 6H), 0.83-0.91 (m, 12H), 1.22 (d, J=6.2 Hz, 6H), 1.25-1.34 (m, 4H), 1.34-1.58 (m, 3H), 1.58-1.72 (m, 3H), 1.98-2.20 (m, 5H), 2.22-2.52 (m, 5H), 2.58-2.68 (m, 1H), 4.02 (q, J=8.1 Hz, 1H), 4.05-4.17 (m, 1H), 4.99 (septet, J=6.2 Hz, 1H), 5.28-5.44 (m, 2H), 5.45-5.68 (m, 2H); $^{13}$C NMR (100 MHz): δ −4.72 (CH$_3$), −4.66 (CH$_3$), −4.58 (CH$_3$), 14.0 (CH$_3$), 18.0 (C), 18.1 (C), 21.8 (CH$_3$), 22.6 (CH$_2$), 24.8 (CH$_2$), 24.9 (CH$_2$), 25.0 (CH$_2$), 25.1 (CH$_2$), 25.3 (CH$_2$), 25.7 (CH$_3$), 26.7 (CH$_2$), 31.77 (CH$_2$), 31.82 (CH$_2$), 34.04 (CH$_2$), 34.09 (CH$_2$), 37.3 (CH$_2$), 37.4 (CH$_2$), 47.62 (CH$_2$), 47.64 (CH$_2$), 52.8 (CH), 53.1 (CH), 53.8 (CH), 54.1 (CH), 67.55 (CH), 67.60 (CH), 72.56 (CH), 72.62 (CH), 72.92 (CH), 73.13 (CH), 126.6 (CH), 126.7 (CH), 130.2 (CH), 130.4 (CH), 130.9 (CH), 136.3 (CH), 137.0 (CH), 173.3 (C), 173.4 (C), 214.9 (C); HRMS (ESI-QTOF) calculated for [C$_{29}$H$_{52}$O$_5$Si+NH$_4$]$^+$=526.3922, found 526.3924; FTIR (KBr, neat) 3446, 2934, 2861, 1736, 1461, 1374, 1250, 1110, 968, 838 cm$^{-1}$.

Example 65

Synthesis of isopropyl (Z)-7-((1R,2R,3R)-3-[(tert-butyldimethylsilyl)oxy]-2-{(S,E)-3-[tert-butyldimethylsilyl)]oxyoct-1-en-1-yl}-5-oxocyclopentyl)hept-5-enoate (10.9a)

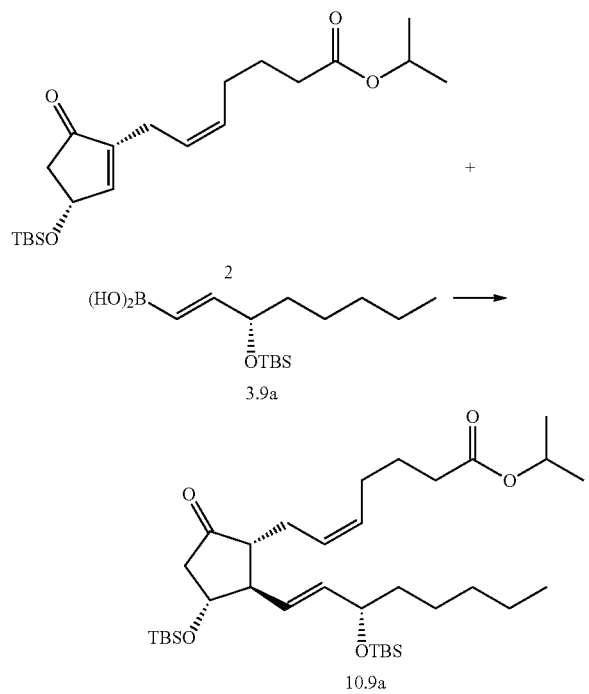

Following procedures described in Example 1 except on a larger scale using 2 (0.30 g, 0.79 mmol) and (S,E){3-[(tert-butyldimethylsilyl)oxy]oct-1-en-1-yl}boronic acid (3.9, 0.34 g, 1.19 mmol), the reaction crude mixture was purified by column chromatography (eluting with 1:80 (v/v) acetone-hexanes) affording the title compound (10.9a, 0.48 g, 98%).

[α]$^{26}_D$ −29.6 (c 1.00, CHCl$_3$); $^1$H NMR (400 MHz): δ 0.02 (s, 3H), 0.043 (s, 3H), 0.049 (s, 3H), 0.052 (s, 3H), 0.87 (s, 9H), 0.89 (s, 9H), 1.22 (d, J=6.4 Hz, 6H), 1.23-1.35 (m, 8H), 1.35-1.52 (m, 3H), 1.66 (quintet, J=7.5 Hz, 2H), 1.98-2.10 (m, 3H), 2.15 (dd, J=8.4, 18.2 Hz, 1H), 2.25 (t, J=7.6 Hz, 2H), 2.27-2.53 (m, 3H), 2.63 (ddd, J=1.1, 7.0, 18.2 Hz, 1H), 3.98-4.13 (m, 2H), 4.99 (septet, J=6.4 Hz, 1H), 5.27-5.44 (m, 2H), 5.45-5.63 (m, 2H); $^{13}$C NMR (100 MHz): δ −4.71 (CH$_3$), −4.65 (CH$_3$), −4.59 (CH$_3$), −4.3 (CH$_3$), 14.0 (CH$_3$), 18.0 (C), 18.2 (C), 21.8 (CH$_3$), 22.6 (CH$_2$), 24.8 (CH$_2$), 25.1 (CH$_2$), 25.2 (CH$_2$), 25.8 (CH$_3$), 25.9 (CH$_3$), 26.7 (CH$_2$), 31.9 (CH$_2$), 34.1 (CH$_2$), 38.6 (CH$_2$), 47.7 (CH$_2$), 52.7 (CH), 53.9 (CH), 67.4 (CH), 72.6 (CH), 73.3 (CH), 126.6 (CH), 128.6 (CH), 130.8 (CH), 136.5 (CH), 173.1 (C), 215.4 (C); HRMS (ESI-QTOF) calculated for [C$_{35}$H$_{66}$O$_5$Si$_2$+NH$_4$]$^+$=640.4787, found 640.4775; FTIR (KBr, neat) 2937, 2861, 1738, 1577, 1467, 1371, 1250, 1107, 835, 774 cm$^{-1}$.

Example 66

Synthesis of isopropyl (Z)-7-((1R,2R,3R,5S)-3-[(tert-butyldimethylsilyl)oxy]-2-{(S,E)-3-[(tert-butyldimethylsilyl)oxy]oct-1-en-1-yl1-5-hydroxycyclopentyl)hept-5-enoate (11.9a)

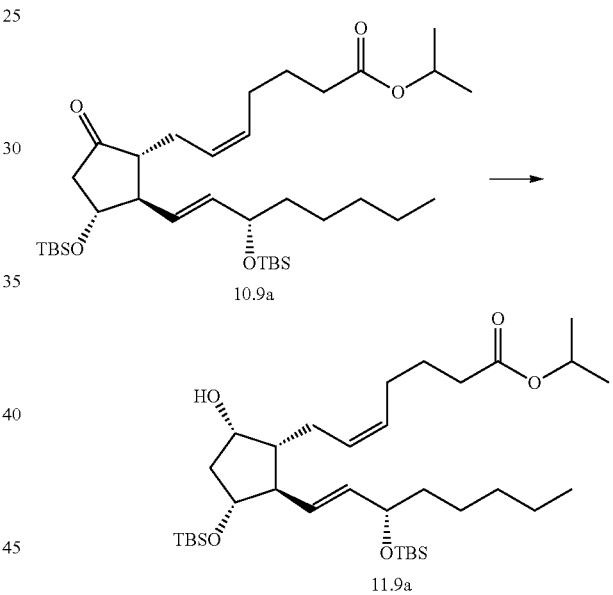

To a THF (6.4 mL) solution of 10.9a (80 mg, 0.13 mmol) was added a solution of L-Selectride® (0.15 mL, 1.0 M in THF, 0.15 mmol) at −78° C. The mixture was stirred at −78° C. for 20 min and directly concentrated at ambient temperature to give a residue which was purified by column chromatography (eluting with 1:8 (v/v) EtOAc-hexanes) to afford the title compound (11.9a, 61 mg, 76%).

[α]$^{23}_D$ −6.3 (c 1.00, CHCl$_3$); $^1$H NMR (400 MHz): δ 0.01 (s, 3H), 0.04 (s, 3H), 0.046 (s, 3H), 0.049 (s, 3H), 0.87 (s, 9H), 0.88 (s, 9H), 1.22 (d, J=6.2 Hz, 6H), 1.24-1.52 (m, 10H), 1.67 (quintet, J=7.5 Hz, 2H), 1.72-1.92 (m, 2H), 2.04-2.21 (m, 3H), 2.22-2.39 (m, 4H), 2.68 (d, J=9.2 Hz, 1H), 3.96-4.15 (m, 3H), 4.99 (septet, J=6.2 Hz, 1H), 5.26-5.52 (m, 4H); $^{13}$C NMR (100 MHz): δ −4.9 (CH$_3$), −4.8 (CH$_3$), −4.6 (CH$_3$), −4.3 (CH$_3$), 14.0 (CH$_3$), 17.8 (C), 18.2 (C), 21.8 (CH$_3$), 22.6 (CH$_2$), 25.0 (CH$_2$), 25.8 (CH$_3$), 25.9 (CH$_3$), 26.6 (CH$_2$), 26.7 (CH$_2$), 31.8 (CH$_2$), 34.1 (CH$_2$), 38.6 (CH$_2$), 42.9 (CH$_2$), 51.8 (CH), 56.4 (CH), 67.3 (CH), 73.2 (CH), 74.7 (CH), 80.0 (CH), 129.2 (CH), 129.5 (CH), 130.8 (CH), 134.4 (CH), 173.2 (C); LRMS (ESI): calculated for $[C_{35}H_{68}O_5Si_2]$=624.5, found 624.5; HRMS (ESI-QTOF) calculated for $[C_{35}H_{68}O_5Si_2+H]^+$=625.4678, found 625.4676; FTIR (KBr, neat) 3433, 2936, 1722, 1636, 1457, 1250, 1088, 832, 659, 503 cm$^{-1}$.

Example 67

Synthesis of (Z)-7-(1R,2R,3R,5S)-3-[(tert-butyldimethylsilyl)oxy]-2-{(S,E)-3-[(tert-butyldimethylsilyl)oxy]oct-1-en-1-yl}-5-hydroxycyclopentyl)hept-5-enoic acid (12.9a)

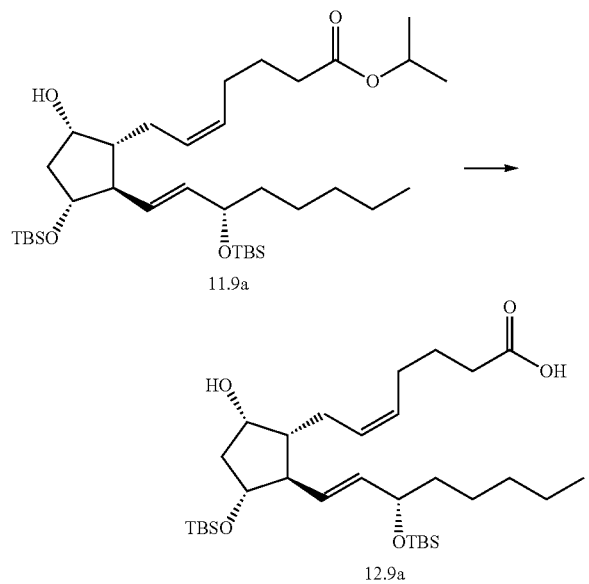

To a solution of the compound 11.9a (1.70 g, 2.7 mmol) in MeOH (20 mL) was added 25% NaOMe-MeOH (9.3 mL, 41 mmol) at room temperature and the mixture was stirred until full conversion was reached as indicated by TLC (1:4 EtOAc-n-heptane). 10% aq. NaOH (10 mL) was added and the mixture was heated at 50° C. for 2 hours. The solution was cooled to room temperature and added 10% aq. citric acid (60 mL). The layers were separated and the aqueous phase was extracted with EtOAc (60 mL×3). The organic layers were combined, washed with brine (150 mL), dried over MgSO$_4$ (4.0 g), filtered and concentrated under reduced pressure. The resulting residue was purified by column purification on silica gel (51 g silica gel; eluting with 1:2 (v/v) EtOAc-n-heptane (800 mL)) to give the title compound 12.9a (1.42 g, 2.44 mmol, 90% yield).

$[\alpha]^{20}_D$+12.09 (c 1.0, CH$_2$Cl$_2$); $^1$H NMR (400 MHz, CDCl$_3$): δ 5.52-5.44 (m, 2H), 5.40-5.32 (m, 2H), 4.14 (s, 1H, br), 4.06 (m, 2H), 2.37-2.28 (m, 4H), 2.27-2.19 (m, 3H) 1.93-1.83 (m, 2H), 1.73 (m, 2H), 1.50-1.10 (m, 3H), 1.27 (m, 7H), 0.89 (m, 21H), 0.07-0.03 (m, 12H); $^{13}$C NMR (100 MHz, CDCl$_3$): δ 179.1, 134.4, 130.7, 129.6, 129.0, 80.0, 74.7, 73.2, 56.4, 51.8, 42.8, 38.5, 33.4, 31.8, 26.6, 26.5, 25.9 (×3), 25.8 (×3), 25.0, 24.6, 22.6, 18.2, 17.8, 14.0, −4.3, −4.6, −4.8, −4.9; HRMS (ESI-QTOF) calculated for $[C_{32}H_{62}O_5Si_2+Na]^+$=605.4028, found 605.4018; FTIR (KBr, neat) 2955, 2928, 2856, 1710, 1472, 1463, 1361, 1251, 1082, 870, 835 cm$^{-1}$.

Example 68

Synthesis of dinoprost (PGF$_{2\alpha}$; 12.9)

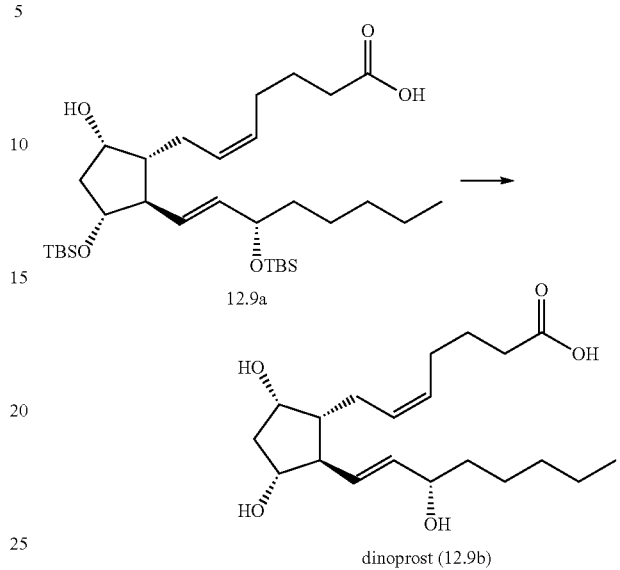

dinoprost (12.9b)

Aqueous HCl (3 N, 6.3 mL, 19 mmol) was added to a stirred solution of compound 12.9a (1.1 g, 1.9 mmol) in THF (19 mL) at room temperature. After 6 hours, the reaction solution was neutralized with sat. aq. NaHCO$_3$ (30 mL) and extracted with EtOAc (40 mL×2). The organic layers were combined, washed with sat. aq. NaCl (50 mL), dried over MgSO$_4$, filtered and concentrated under reduced pressure. The product was purified by column chromatography on silica gel (33 g silica gel; eluting with 1:20 (v/v) MeOH—CH$_2$Cl$_2$ (300 mL) then 1:5 (500 mL) to give dinoprost as colorless oil (12.9, 595 mg, 89%).

$[\alpha]^{20}_D$+23.7 (c 0.50, THF); $^1$H NMR (400 MHz, MeOD): δ 5.55-5.43 (m, 3H), 5.38-5.31 (m, 1H), 4.10 (td, J=5.6, 2.0 Hz, 1H), 4.01 (dd, J=12.8, 6.4 Hz, 1H), 3.83 (ddd, J=7.6, 5.6, 5.2 Hz, 1H), 2.36-2.26 (m, 1H), 2.26-2.20 (m, 3H), 2.18-2.15 (m, 1H), 2.14-2.07 (m, 3H), 1.69-1.58 (m, 4H), 1.57-1.53 (m, 2H), 1.51-1.29 (m, 6H), 0.91 (t, J=6.8 Hz, 3H); $^{13}$C NMR (100 MHz, MeOD): δ 178.5, 136.6, 134.3, 130.5, 130.4, 77.9, 74.1, 72.3, 56.2, 50.9, 44.4, 38.5, 35.0, 33.1, 27.8, 26.5, 26.3 (×2), 23.9, 14.6; HRMS (ESI-QTOF) calculated for $[C_{20}H_{34}O_5+Na]^+$=377.2298, found 377.2298; FTIR (KBr, neat) 3346, 3006, 2954, 2930, 2858, 1708, 1550, 1456, 1409, 1237, 1081, 1053, 1025, 969 cm$^{-1}$.

Example 69

Synthesis of isopropyl (Z)-7-{(1R,2S,3R)-3-[(tert-butyldimethylsilyl)oxy]-2-(cyclohex-1-en-1-yl)-5-oxocyclopentyl}hept-5-enoate (10.20)

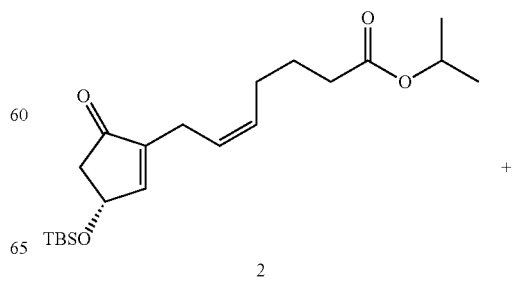

2

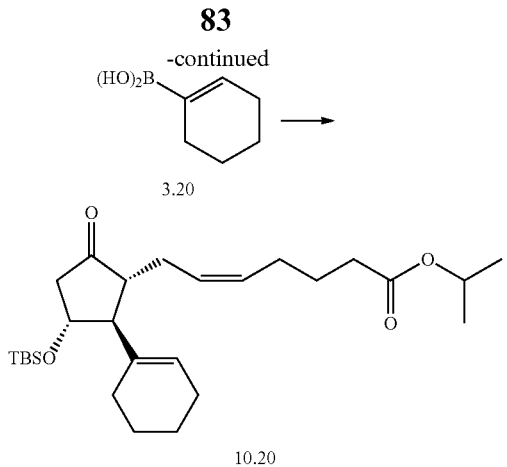

Following the procedure described in Example 1 the title compound was synthesized using cyclohex-1-en-1-ylboronic acid (28 mg, 0.225 mmol). The crude product mixture was then purified by column chromatography (eluting with 1:80 (v/v) acetone-hexanes) affording the title compound (10.20, 26 mg, 38%).

$^1$H NMR (400 MHz, CDCl$_3$): δ 0.02 (s, 3H), 0.03 (s, 3H), 0.87 (s, 9H), 1.22 (d, J=6.2 Hz, 6H), 1.58-1.70 (m, 6H), 1.85-1.95 (m, 2H), 1.98-2.08 (m, 4H), 2.09-2.31 (m, 6H), 2.38 (dd, J=8.5, 12.4 Hz, 1H), 2.64 (dd, J=7.2, 18.5 Hz, 1H), 4.11 (q, J=8.4 Hz, 1H), 5.00 (septet, J=6.2 Hz, 1H), 5.29-5.52 (m, 2H), 5.45-5.60 (m, 1H); HRMS (ESI-TOF) calculated for [C$_{27}$H$_{46}$O$_4$Si+H]$^+$=463.3238, found 463.3240.

Example 70

Synthesis of methyl (E)-7-{3-[(tert-butyldimethylsilyl)oxy]-5-oxo-2-styrylcyclopentyl}heptanoate (Iba)

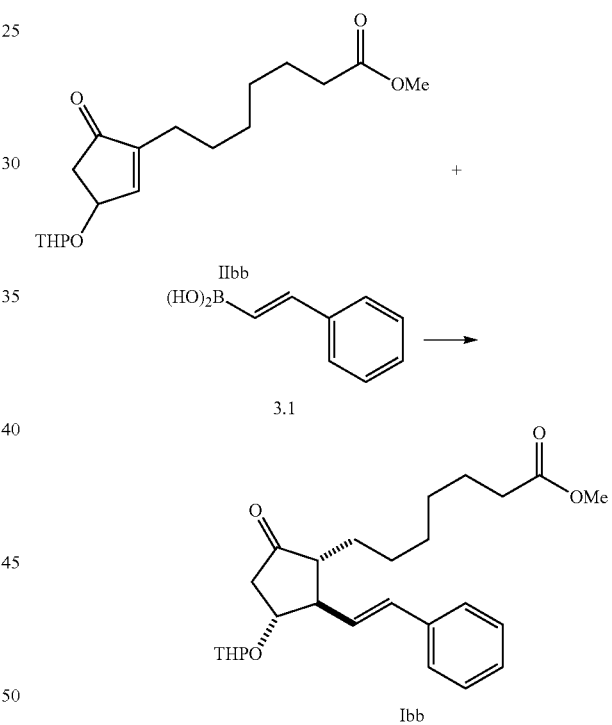

Following the procedure described in Example 1 the title compound was synthesized using methyl 7-{3-[(tert-butyldimethylsilyl)oxy]-5-oxocyclopent-1-en-1-yl}heptanoate (IIba, 53 mg, 0.15 mmol). The crude product mixture was then purified by column chromatography (eluting with 1:80 (v/v) acetone-hexanes) affording the title compound (Iba, 36 mg, 53%).

$^1$H NMR (400 MHz, CDCl$_3$): δ 0.01 (s, 3H), 0.02 (s, 3H), 0.86 (s, 9H), 1.22-1.33 (m, 6H), 1.35-1.48 (m, 1H), 1.50-1.70 (m, 3H), 2.02-2.12 (m, 1H), 2.19-2.30 (m, 3H), 2.54-2.73 (m, 2H), 3.64 (s, 3H), 4.11 (q, J=8.5 Hz, 1H), 6.05 (dd, J=8.6, 15.8 Hz, 1H), 6.52 (d, J=15.8 Hz, 1H), 7.22-7.26 (m, 1H), 7.30-7.38 (m, 4H); HRMS (ESI-TOF) calculated for [C$_{27}$H$_{42}$O$_4$Si+H]$^+$=459.2925, found 459.2930.

Example 71

Synthesis of methyl (E)-7-{5-oxo-2-styryl-3-[(tetrahydro-2H-pyran-2-yl)oxy]cyclopentyl}heptanoate (Ibb)

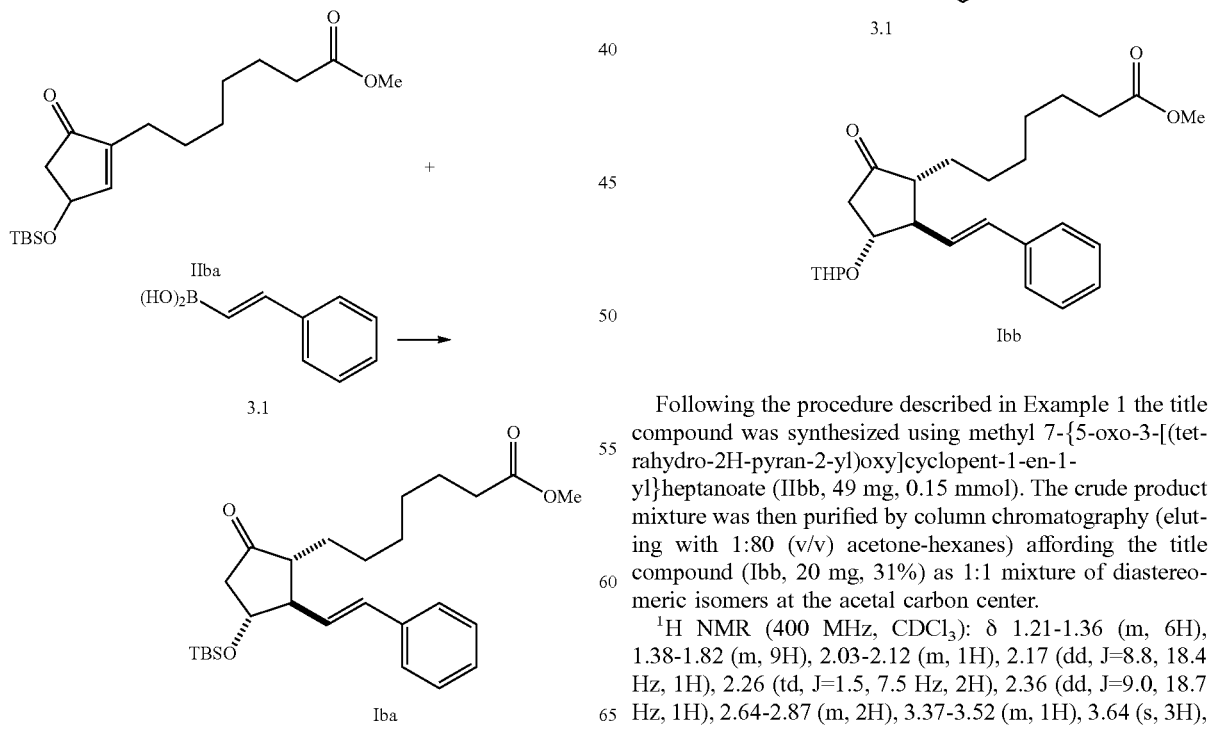

Following the procedure described in Example 1 the title compound was synthesized using methyl 7-{5-oxo-3-[(tetrahydro-2H-pyran-2-yl)oxy]cyclopent-1-en-1-yl}heptanoate (IIbb, 49 mg, 0.15 mmol). The crude product mixture was then purified by column chromatography (eluting with 1:80 (v/v) acetone-hexanes) affording the title compound (Ibb, 20 mg, 31%) as 1:1 mixture of diastereomeric isomers at the acetal carbon center.

$^1$H NMR (400 MHz, CDCl$_3$): δ 1.21-1.36 (m, 6H), 1.38-1.82 (m, 9H), 2.03-2.12 (m, 1H), 2.17 (dd, J=8.8, 18.4 Hz, 1H), 2.26 (td, J=1.5, 7.5 Hz, 2H), 2.36 (dd, J=9.0, 18.7 Hz, 1H), 2.64-2.87 (m, 2H), 3.37-3.52 (m, 1H), 3.64 (s, 3H), 3.77-3.88 (m, 1H), 4.11 (q, J=8.6 Hz, 0.5H), 4.27 (q, J=8.7 Hz, 0.5H), 4.68-4.77 (m, 1H), 6.09-6.23 (m, 1H), 6.50-6.63

(m, 1H), 7.20-7.25 (m, 1H), 7.29-7.42 (m, 4H); HRMS (ESI-TOF) calculated for $[C_{26}H_{36}O_5+Na]^+=451.2455$, found 451.2459.

Example 72

Synthesis of isopropyl (Z)-7-[(1R,2R,3R)-3-hydroxy-5-oxo-2-((E)-styryl)cyclopentyl]hept-5-enoate (Iaa)

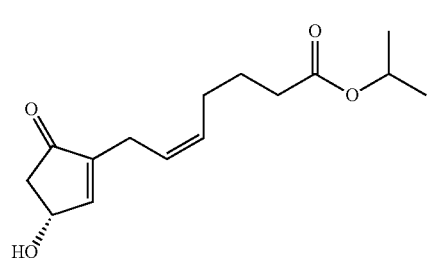

IIaa

+

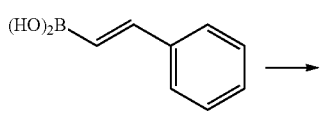

3.1

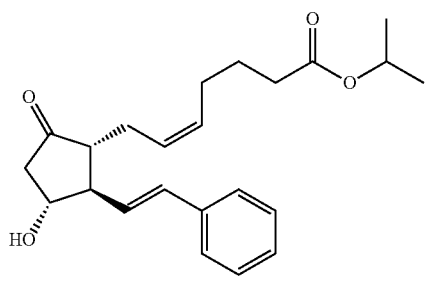

Iaa

A solution of isopropyl (R,Z)-7-(3-hydroxy-5-oxocyclopent-1-en-1-yl)hept-5-enoate (IIaa, 50 mg, 0.19 mmol), 3.1 (45 mg, 0.22 mmol), $[RhCl(1,5-cyclooctadiene)]_2$ (1.4 mg, 2.8 μmol) and aq. KOH (11.9 μL, 3.0 M aq. KOH, 36 μmmol) in MeOH (1.0 mL) was stirred under microwave irradiation (CEM, Discover S; or Milestone, Startsynth; the temperature was set at 30° C.). The residue was purified by column chromatography (eluting with 1:20 (v/v) acetone-hexanes) affording the title compound (Iaa, 27 mg, 39%).

$^1$H NMR (400 MHz, CDCl$_3$): δ 1.19 (d, J=6.2 Hz, 6H), 1.58-1.73 (m, 2H), 1.94 (br, 1H), 2.04 (q, J=7.2 Hz, 2H), 2.20 (t, J=7.6 Hz, 2H), 2.32-2.54 (m, 4H), 2.56-2.65 (m, 1H), 2.72-2.81 (m, 1H), 4.48 (t, J=4.2 Hz, 1H), 4.96 (septet, J=6.2 Hz, 1H), 5.25-5.45 (m, 2H), 6.34 (dd, J=7.9, 16.1 Hz, 1H), 6.57 (d, J=16.1 Hz, 1H), 7.23-7.28 (m, 1H), 7.31-7.41 (m, 4H); HRMS (EI) calculated for $[C_{23}H_{30}O_4]^+=370.2139$, found 370.2141.

Example 73

Synthesis of methyl (E)-7-[3-(allyloxy)-5-oxo-2-styrylcyclopentyl]heptanoate (Ibc)

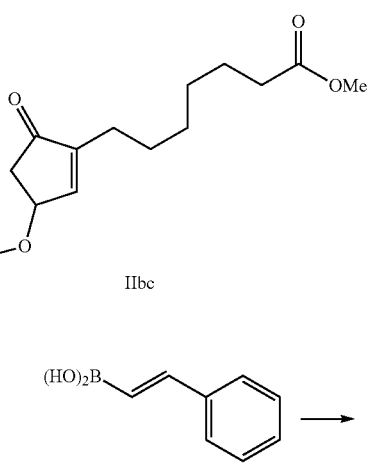

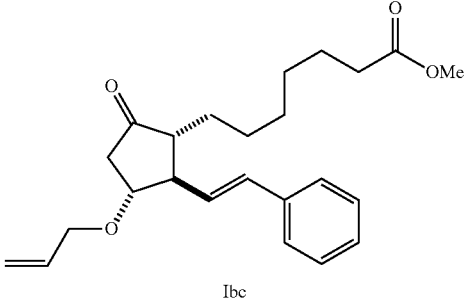

Following the procedure described in Example 1 the title compound was synthesized using methyl 7-[3-(allyloxy)-5-oxocyclopent-1-en-1-yl]heptanoate (IIbc, 42 mg, 0.15 mmol). The crude product mixture was filtered through a silica gel column and then analyzed by $^1$H NMR spectroscopy which showed 2% yield of the title compound Ibc.

HRMS (ESI-TOF) calculated for $[C_{24}H_{32}O_4+H]^+=385.2373$, found 385.2375.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A process for preparing a 2,3-disubstituted-4-oxy-cyclopentan-1-one compound of formula I

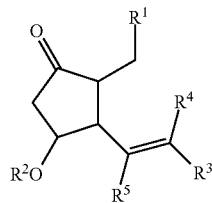

(I)

the process comprises contacting a 2-substituted-4-oxy-cyclopent-2-en-1-one compound of formula II

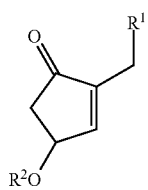

(II)

with a compound of formula III

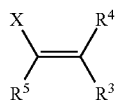

(III)

in a solvent with a metal additive, optionally in the presence of a basic additive, wherein the metal additive is used in substoichiometric amounts, to give the compound of formula I;

wherein $R^1$, $R^3$, $R^4$ and $R^5$ independently represent hydrogen, aryl, heteroaryl, alkyl, arylalkyl, aryloxyalkyl, alkenyl, or alkynyl; or $R^3$ and $R^5$ are taken together to form a 5- to 7- membered carbocyclic ring, optionally having one or two heteroatoms as ring vertices, wherein the heteroatoms are selected from the group consisting of O, N and S; or $R^3$ and $R^4$ are taken together to form a 5- to 7-membered carbocyclic ring, optionally having one or two heteroatoms as ring vertices, wherein the heteroatoms are selected from the group consisting of O, N and S, and wherein each of $R^1$, $R^3$, $R^4$ and $R^5$ are optionally substituted with from one to three members selected from the group consisting of halogen, hydroxy, $C_{1-4}$ alkyl, $C_{1-4}$ haloalkyl, $C_{1-4}$ alkoxy, silyloxy, aryloxy, acyloxy, a 5- to 7-membered heterocyclic ring, oxo, COOH, $CONH_2$, $CONHC_{1-4}$ alkyl, $C(O)OCH_2C_{6-10}$ aryl, $C(O)OC_{6-10}$ aryl and $C(O)OC_{1-4}$ alkyl;

$R^2$ represents hydrogen or a hydroxyl-protecting group;

X represents a boron-containing group.

2. The process of claim 1, wherein the compound of formula I is

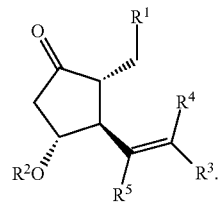

(I')

3. The process of claim 1, wherein $R^3$ is alkyl, aryl, arylalkyl or aryloxyalkyl, each of which is optionally substituted with from one to three members selected from the group consisting of $C_{1-4}$ alkyl, $C_{1-4}$ alkoxy, silyloxy, aryloxy, acyloxy, tetrahydropyranyl (THP), trifluoromethyl and fluoro.

4. The process of claim 1, wherein the solvent is selected from the group consisting of water, methanol, ethanol, isopropyl alcohol, isobutyl alcohol, 1,4-dioxane, toluene, tetrahydrofuran (THF), 2-methyl-tetrahydrofuran (2-Me-THF), diglyme, acetonitrile, N-methylpyrrolidone, N,N-dimethylformamide (DMF), N,N-dimethylacetamide (DMAC), ethylene glycol and combinations thereof.

5. The process of claim 4, wherein the solvent is methanol.

6. The process of claim 1, wherein the metal additive is selected from the group consisting of rhodium compounds, cobalt compounds, nickel compounds and combinations thereof.

7. The process of claim 6, wherein the rhodium compound is a rhodium(I) compound selected from the group consisting of $[RhCl(1,5\text{-cyclooctadiene})]_2$, $[RhCl(C_2H_4)_2]_2$, $[RhCl(C_2H_4)_2]_2$ with a diene ligand additive, $[RhCl(\text{norbornadiene})]_2$, $[RhOH(1,5\text{-cyclooctadiene})]_2$ and combinations thereof.

8. The process of claim 7, wherein the rhodium(I) compound is selected from the group consisting of $[RhCl(1,5\text{-cyclooctadiene})]_2$ and $[RhOH(1,5\text{-cyclooctadiene})]_2$.

9. The process of claim 1, wherein the basic additive is selected from the group consisting of $KHF_2$, t-BuOLi, t-BuONa, t-BuOK, $K_3PO_4$, $K_2CO_3$, $Cs_2CO_3$, LiOH, NaOH, KOH, CsOH, KF, CsF, $NaHCO_3$, $KH_2PO_4$, 1,3-diaminopropane, t-BuNH$_2$, i-Pr$_2$NH, piperidine, Et$_3$N, 2,6-lutidine and combinations thereof.

10. The process of claim 9, wherein the basic additive is potassium hydroxide.

11. The process of claim 1, wherein the hydroxyl-protecting group is selected from the group consisting of tetrahydropyranyl (THP), methoxymethyl (MOM), [2-(trimethylsilyl) ethoxy]methyl (SEM), trialkylsilyl, triarylsilyl, diarylalkylsilyl, benzyl, 4-methoxybenzyl (PMB), alkylcarbonyl, arylcarbonyl and allyl.

12. The process of claim 11, wherein the trialkylsilyl is tert-butyldimethylsilyl (TBS).

13. The process of claim 1, wherein the boron-containing group X is selected from the group consisting of $B(OH)_2$, $B(OR)_2$ where R is an alkyl group or an aryl group, $BR_2$ where R is an alkyl group, $BR_2$ where R is a vinyl group, $BR_2$ where R is a carboxylate group, BR where R is a bidentate carboxylate group, $BR_2$ where R is an aryloxy group, BR where R is a bidentate aryloxy group, a 9-borabicyclo(3.3.1)nonane (9-BBN) group, $BF_3M$ where M is a metal ion, $BF_3M$ where M is an ammonium or phosphonium ion, and $BR_3M$ where R is a vinyl group and where M is a metal ion or is an ammonium or phosphonium ion.

14. The process of claim 13, wherein the boron-containing group X is selected from the group consisting of B(OH)$_2$ and BF$_3$M where M is a metal ion.

15. The process of claim 1 is conducted at a temperature from 0 to 80° C.

16. The process of claim 1, wherein the basic additive is used in substoichiometric amounts.

17. The process of claim 1, further comprising converting the 2,3-disubstituted -4-oxy-cyclopentan-l-one compound of formula I to travoprost, bimatoprost, lubiprostone, dinoprost, dinoprostone, tafluprost, carboprost, alprostadil, latanoprost or unoprostone isopropyl.

18. The process of claim 1, wherein the 2,3-disubstituted-4-oxy-cyclopentan -1-one compound of formula I is the compound of formula 10.9a,

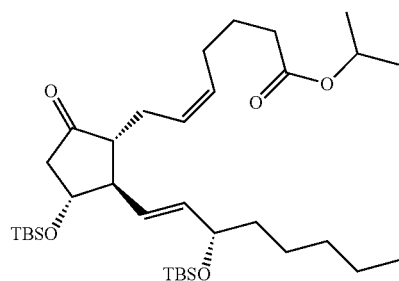

19. The process of claim 1, wherein the 2,3-disubstituted-4-oxy-cyclopentan -1-one compound of formula I is the compound of formula 10.17,

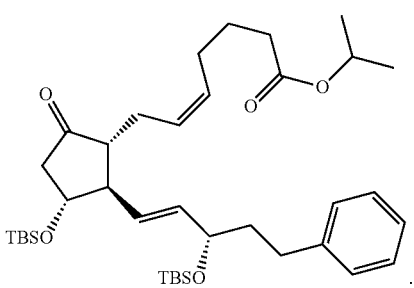 [SMILES: CC(C)OC(=O)CCC/C=C\C[C@H]1C(=O)C[C@@H](O[Si](C)(C)C(C)(C)C)[C@@H]1/C=C/[C@H](CCc1ccccc1)O[Si](C)(C)C(C)(C)C]

20. The process of claim 1, wherein the 2,3-disubstituted-4-oxy-cyclopentan -1-one compound of formula I is the compound of formula 10.18,

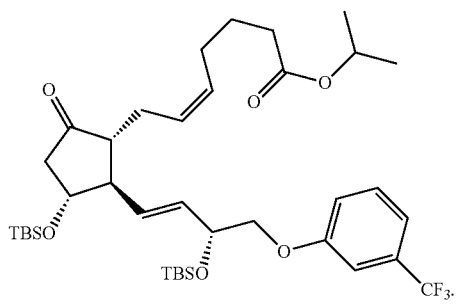 [SMILES: CC(C)OC(=O)CCC/C=C\C[C@H]1C(=O)C[C@@H](O[Si](C)(C)C(C)(C)C)[C@@H]1/C=C/[C@H](COc1cccc(C(F)(F)F)c1)O[Si](C)(C)C(C)(C)C]

21. The process of claim 1, wherein the 2,3-disubstituted-4-oxy-cyclopentan -1-one compound of formula I is the compound of formula 10.7,

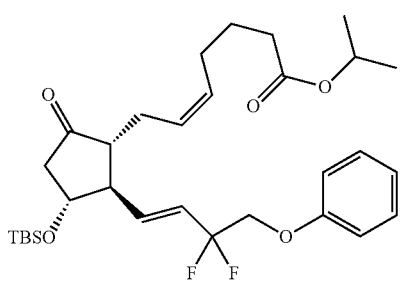

22. The process of claim 1, wherein the 2,3-disubstituted-4-oxy-cyclopentan -1-one compound of formula I is the compound of formula 10.19,

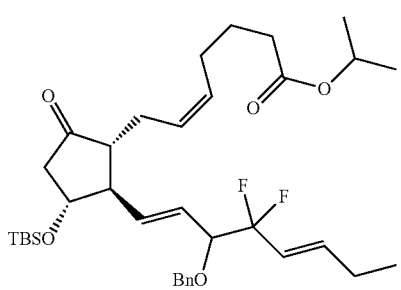

* * * * *